(12) United States Patent
Burai et al.

(10) Patent No.: US 9,809,597 B2
(45) Date of Patent: Nov. 7, 2017

(54) GANCICLOVIR DERIVATIVES FOR MODULATING INNATE AND ADAPTIVE IMMUNITY AND FOR USE IN IMMUNOTHERAPY

(71) Applicant: The Board of Trustees of the Leland Stanford Junior University, Stanford, CA (US)

(72) Inventors: Ritwik Burai, West Bengal (IN); Hilal Lashuel, Ecublens (CH); Vidhu Mathur, Mountain View, CA (US); Anton Wyss-Coray, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/241,821

(22) Filed: Aug. 19, 2016

(65) Prior Publication Data

US 2017/0050967 A1     Feb. 23, 2017

Related U.S. Application Data

(60) Provisional application No. 62/207,903, filed on Aug. 20, 2015.

(51) Int. Cl.
  *C07D 473/18*     (2006.01)
  *A61K 45/06*      (2006.01)
  *A61K 31/52*      (2006.01)

(52) U.S. Cl.
  CPC .......... *C07D 473/18* (2013.01); *A61K 31/52* (2013.01); *A61K 45/06* (2013.01)

(58) Field of Classification Search
  CPC ....... C07D 473/18; A61K 45/06; A61K 31/52
  USPC ................................................. 514/263.21
  See application file for complete search history.

(56) References Cited

U.S. PATENT DOCUMENTS

| 6,051,576 A * | 4/2000 | Ashton | A61K 31/495 |
| | | | 514/176 |
| 2013/0039933 A1 | 2/2013 | Barber | |
| 2014/0329889 A1 | 11/2014 | Vance et al. | |

OTHER PUBLICATIONS

Cai et al. Zhongguo Kangshengsu Zazhi (J. of Chinese Antibiotic Research) (2007), 32(1), p. 63, S1.*
Li et al. Progress in Polymer Sciences (2013) 38, p. 421-444.*
Faulds et al. (1990) Ganciclovir. A review of its antiviral activity, pharmacokinetic properties and therapeutic efficacy in cytomegalovirus infections. Drugs 39:597-638.
Ding et al. (2014) Antiviral drug ganciclovir is a potent inhibitor of microglial proliferation and neuroinflammation. J Exp Med 211:189-198.
Borden et al. (2007) Interferons at age 50: past, current and future impact on biomedicine. Nat Rev Drug Discov 6:975-990.
Littler et al. (1992) Human cytomegalovirus UL97 open reading frame encodes a protein that phosphorylates the antiviral nucleoside analogue ganciclovir. Nature 358: 160-162.
Hornung et al. (2014) OAS proteins and cGAS: unifying concepts in sensing and responding to cytosolic nucleic acids. Nat Rev Immunol 14:521-528.
Ishikawa et al. (2009) STING regulates intracellular DNA-mediated, type I interferon-dependent innate immunity. Nature 461: 788-792.
Barber et al. (2011) STING-dependent signaling. Nat Immunol 12: 929-930.
Gao et al. (2013) Structure-function analysis of STING activation by c[G(2',5')pA(3',5')p] and targeting by antiviral DMXAA. Cell 154:748-762.
Prantner et al. (2012) 5,6-Dimethylxanthenone-4-acetic acid (DMXAA) activates stimulator of interferon gene (STING)-dependent innate immune pathways and is regulated by mitochondrial membrane potential. J Biol Chem 287:39776-39788.
Cavlar et al. (2013) Species-specific detection of the antiviral small-molecule compound CMA by STING. Embo J 32:1440-1450.
Conlon et al. (2013) Mouse, but not human STING, binds and signals in response to the vascular disrupting agent 5,6-dimethylxanthenone-4-acetic acid. J Immunol 190:5216-5225.
Sauer et al. (2011)The N-ethyl-N-nitrosourea-induced Goldenticket mouse mutant reveals an essential function of Sting in the in vivo interferon response to Listeria monocytogenes and cyclic dinucleotides. Infect Immun 79:688-694.
Frank et al. (1999) Fludarabine-induced immunosuppression is associated with inhibition of STAT1 signaling. Nat Med 5:444-447.
Zhou et al. (2014) Specificity and mechanism-of-action of the JAK2 tyrosine kinase inhibitors ruxolitinib and SAR302503 (TG101348). Leukemia 28:404-407.
Burdette et al. (2011) STING is a direct innate immune sensor of cyclic di-GMP. Nature 478:515-518.
Lemos et al. (2014) Activation of the STING adaptor attenuates experimental autoimmune encephalitis. J Immunol 192:5571-5578.
Elion et al. (1977) Selectivity of action of an antiherpetic agent, 9-(2-hydroxyethoxymethyl) guanine. Proc Natl Acad Sci USA 74:5716-5720.
He et al. (2015) Potential therapeutic targets in the process of nucleic acid recognition: opportunities and challenges. Trends Pharmacol Sci 36:51-64.
Liu et al. (2014) Activated STING in a vascular and pulmonary syndrome. N Engl J Med 371:507-518.
Sharma et al. (2015) Suppression of systemic autoimmunity by the innate immune adaptor STING. Proc Natl Acad Sci USA 112:E710-717.
Jeremiah et al. (2014) Inherited STING-activating mutation underlies a familial inflammatory syndrome with lupus-like manifestations. J Clin Invest 124:5516-5520.

(Continued)

*Primary Examiner* — Yong Chu
(74) *Attorney, Agent, or Firm* — Jenny Buchbinder

(57) ABSTRACT

Compositions and methods for modulating innate and adaptive immunity and for use in immunotherapy are disclosed. In particular, the invention relates to novel ganciclovir derivatives and methods of using them for the treatment of immune-related disorders, including inflammation, autoimmunity, and infections, and neurological disorders, and cancer.

25 Claims, 54 Drawing Sheets

(56) References Cited

OTHER PUBLICATIONS

Heppner et al. (2005) Experimental autoimmune encephalomyelitis repressed by microglial paralysis. Nat Med 11(2):146-152.

* cited by examiner

Scheme 1. Synthesis of ganciclovir-thiol derivative

Scheme 2. Labeling with Biotin $^{13}$C NMR spectra of Ganciclovir-Thiol in methanol-$d_4$

GANCICLOVIR DERIVATIVES FOR MODULATING INNATE AND ADAPTIVE IMMUNITY AND FOR USE IN IMMUNOTHERAPY

CROSS-REFERENCE TO RELATED APPLICATION

This application claims benefit under 35 U.S.C. §119(e) of provisional application 62/207,903, filed Aug. 20, 2015, which is hereby incorporated by reference in its entirety.

TECHNICAL FIELD

The present invention pertains generally to compositions for modulating innate and adaptive immunity and for use in immunotherapy. In particular, the invention relates to novel ganciclovir derivatives and methods of using them for the treatment of immune-related disorders, including inflammation, autoimmunity, and infections, and neurological disorders and cancer.

BACKGROUND

Neuroinflammation and changes in immunity are key features of brain aging and neurodegeneration. Modulation of neuroinflammation is thought to be an attractive therapeutic target for Alzheimer's disease and related neurodegenerative and neuroimmune diseases, but very few treatments exist.

Ganciclovir (GCV) and other nucleoside analogs of 2'-deoxyguanosine have been used previously as anti-viral drugs for treatment of herpes viral infections (Faulds et al. (1990) Drugs 39:597-638). Recently, GCV been shown to ameliorate the disease course and pathology of experimental autoimmune encephalomyelitis (EAE) in a mouse model of multiple sclerosis (Ding et al. (2014) J Exp Med 211:189-198).

There remains a need for better methods of treating inflammation, particularly neuroinflammation associated with neurodegenerative conditions.

SUMMARY

The invention relates to novel ganciclovir derivatives and methods of using them for modulating innate and adaptive immunity and in immunotherapy.

GCV derivatives that can be used in the practice of the invention include various analogues of GCV, having the chemical formula:

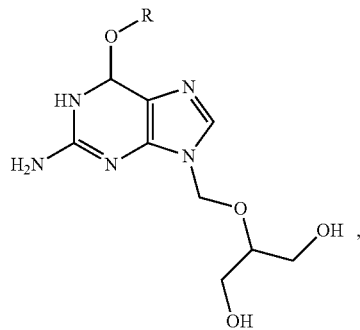

or a pharmaceutically acceptable salt thereof, wherein R is a polyethylene glycol, a propanethiol, 2-[(2-Amino-6-{2-[2-(2-ethoxyethoxy)ethoxy]ethoxy}-6,9-dihydro-1H-purin-9-yl)methoxy]-1,3-propanediol, or 2-({2-Amino-6-[3-(propyldithio)propoxy]-6,9-dihydro-1H-purin-9-yl}methoxy)-1,3-propanediol.

In one embodiment, the GCV derivative comprises a GCV-polyethylene glycol (PEG) monomer (monoGCV) having the formula:

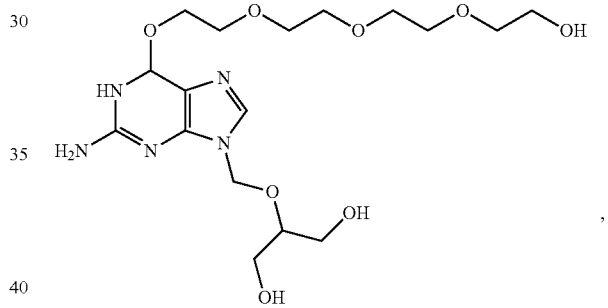

or a pharmaceutically acceptable salt thereof.

In another embodiment, the GCV derivative comprises a GCV-PEG dimer (diGCV) having the formula:

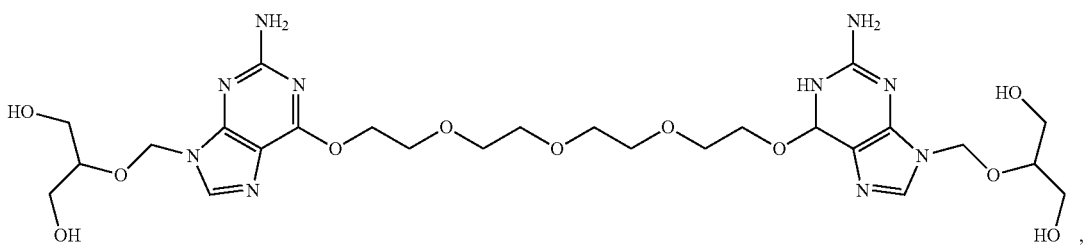 [SMILES: NC1=Nc2c(ncn2COC(CO)CO)C(OCCOCCOCCOCCOc2nc(N)nc3c2ncn3COC(CO)CO)N1]

or a pharmaceutically acceptable salt thereof.

In another embodiment, the GCV derivative comprises a thiol-GCV dimer having the formula:

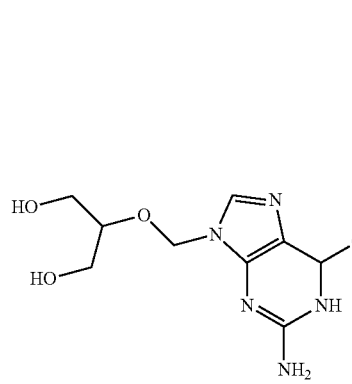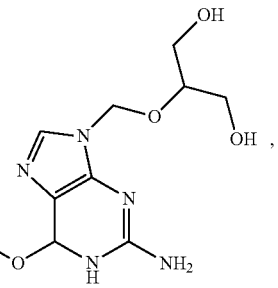

or a pharmaceutically acceptable salt thereof.

In certain embodiments, the invention includes a composition comprising at least one GCV derivative and a pharmaceutically acceptable excipient. In one embodiment, the composition further comprises one or more other drugs for treating a disease or condition. For example, the composition may further comprise one or more anti-inflammatory agents, analgesic agents, or immunosuppressive agents.

In one embodiment, the invention includes a method of treating a subject for inflammation, autoimmunity, an infection, a neurological disorder, or cancer, the method comprising administering to the subject a therapeutically effective amount of a GCV derivative. In certain embodiments, the ganciclovir derivative is selected from the group consisting of monoGCV, diGCV, and thiol-GCV dimer.

By "therapeutically effective dose or amount" of a GCV derivative is intended an amount that, when administered as described herein, brings about a positive therapeutic response such as improved recovery from an immune-related disorder, such as inflammation, autoimmunity, or an infection, or a neurological disorder, or cancer. Improved recovery may include a reduction in inflammation, pain, or autoimmune-induced tissue damage, or prolonged survival. Additionally, a GCV derivative may activate the stimulator of interferon genes (STING) pathway, decrease the microglial inflammatory response, decrease microglial nitric oxide production, reduce microglial proliferation, inhibit inflammatory factors (e.g., iNOS and CCL2), and/or activate a type I interferon response (e.g., induce IFN-β and CXCL10 in microglia and monocytes). In the case of an inflammatory disorder, a therapeutically effective dose or amount may decrease neuroinflammation and/or systemic inflammation.

A GCV derivative may be administered by any suitable mode of administration. In certain embodiments, a GCV derivative is administered orally, intravenously, intra-arterially, subcutaneously, or intralesionally to a subject. In one embodiment, the GCV derivative is administered locally at a site of inflammation.

Multiple cycles of treatment may be administered to a subject. In certain embodiments, the GCV derivative is administered according to a daily dosing regimen or intermittently.

In another aspect, the invention includes a method of decreasing neuroinflammation in a subject, the method comprising contacting microglia with a composition comprising a GCV derivative.

In another aspect, the invention includes a method of modulating an immune response in a subject, the method comprising administering an effective amount of a GCV derivative to the subject.

In another aspect, the invention includes a method of activating stimulator of interferon genes (STING) in a subject, the method comprising administering an effective amount of a GCV derivative to the subject.

In another aspect, the invention includes a method of activating a type I interferon response in a subject, the method comprising administering an effective amount of a GCV derivative to the subject.

These and other embodiments of the subject invention will readily occur to those of skill in the art in view of the disclosure herein.

BRIEF DESCRIPTION OF THE FIGURES

FIG. 1A shows the structure of Ganciclovir (GCV). FIG. 1B shows the indicated transcripts analyzed by RT-PCR in cells stimulated with IFNγ/LPS with or without 200 μM GCV for 24 hours. FIG. 1C shows the nitrite assay using culture supernatants from 24 hours of IFNγ/LPS and GCV treated cells. FIG. 1D shows the dose response graphs for the indicated proteins secreted by BV-2 microglia upon 24 hours GCV stimulation. FIG. 1E shows RT-PCR for CXCL10 and IFNβ transcripts in primary microglia treated with 200 μM GCV for 6 hours. FIG. 1F shows time curves for CXCL10 and IFNβ transcripts in BV2 cells. FIGS. 1G-1H shows the dose response of GCV in BV-2 microglia showing the CXCL10 transcript (FIG. 1G) and cell viability (FIG. 1H). FIG. 1I shows RT-PCR for CXCL10 and IFNβ transcripts in primary microglia from wildtype and thymidine kinase 1 knockout (tk KO) mice with 6 hours of 200 μM GCV treatment. Fold change is based on control treatment for each genotype. Statistical tests: one-way ANOVA followed by Dunnett's multiple comparison test (FIGS. 1C, 1D, 1F, 1H), unpaired Student's t-test (FIGS. 1B, 1E, 1I).

FIGS. 2A-2B show RT-PCR for CXCL10 transcript in BV-2 cells treated with 200 μM of the indicated compounds for 24 hours. FIG. 2C shows a time curve for RT-PCR for CXCL10 and IFNβ in BV-2 cells treated with 200 μM monoGCV and diGCV. FIGS. 2D and 2E show BV-2 microglia stimulated with IFNγ/LPS and 200 μM monoGCV or diGCV for 24 hours. The indicated transcripts were analyzed by RT-PCR (FIG. 2D) and nitrite assay performed on the cell culture supernatants (FIG. 2E). FIG. 2F shows RT-PCR for CXCL10 transcripts in primary microglia from wildtype and thymidine kinase 1 knockout (tk KO) mice treated with 200 μM drugs for 6 hours. Fold change is based on control treatment for each genotype. Statistical tests: one-way ANOVA followed by Dunnett's multiple comparison test (FIGS. 2A-2E), unpaired Student's t-test (FIG. 2F).

FIG. 3A presents a schematic showing that STING induces IFNβ via Tbk1 and IRF3 and further activation of the Jak/Stat pathway activates an antiviral interferon response. FIGS. 3B-3D show RT-PCR for the indicated transcripts in BV-2 (FIGS. 3B, 3C) and THP-1 (FIG. 3D) cells treated with 200 µM of the indicated drugs for 8-24 hours. FIG. 3E shows that STING was knocked down in BV-2 microglia using an siRNA for 24 hours and then stimulated with 200 µM GCV, monoGCV or diGCV for an additional 24 hours. The RT-PCR analysis shows CXCL10 and STING in control and STING knock down. FIG. 3F shows qRT-PCR analysis of primary microglia from wildtype or STING$^{gt/gt}$ mice treated with 200 µM cGAMP, GCV, monoGCV and diGCV for 6 hours. FIG. 3G shows primary microglia from wildtype or STING$^{gt/gt}$ mice treated with IFNγ/LPS with or without 200 µM GCV for 24 hours. RT-PCR shows indicated transcripts. FIG. 3H shows the RT-PCR for CXCL10 in BV-2 cells treated for 24 hours with 200 µM GCV or diGCV along with 1 µM of the Tbk1 inhibitor Amlexanox (AmX). FIG. 3I shows that IRF3 was knocked down in BV-2 microglia using the siRNA for 24 hours and then stimulated with 200 µM GCV or diGCV for additional 24 hours. The RT-PCR analyses for CXCL10 and IRF3 are shown. Statistical tests: one-way ANOVA followed by Dunnett's multiple comparison test (FIGS. 3C-3D) or unpaired Student's t-test (FIGS. 3E-3I).

FIG. 4A presents a schematic showing the experimental design. The average EAE score (FIG. 4B), percent incidence (FIG. 4D) and percent death (FIG. 4E) are shown for the indicated groups. FIG. 4C shows the average EAE score at 18 days post immunization. FIG. 4F shows representative images from immunohistological analysis of the cerebella. The arrows show Iba1$^+$BrDU$^+$ cells. Quantification of the average number of BrDU$^+$ proliferating cells (FIG. 4G) and Iba1$^+$ microglia (FIG. 4H), percent Iba1$^+$BrDU$^+$ proliferating microglia (FIG. 4I) and CD3$^+$BrDU$^+$ proliferating T-cells (FIG. 4J) are shown. Statistical tests: Two-way ANOVA followed by Sidak's multiple comparisons test between indicated groups.

FIG. 8A shows the RT-PCR for CXCL10 in BV-2 cells treated for 24 hours with 200 µM GCV, diGCV or cGAMP along with 10 µM Fludarabine (Stat1 inhibitor). FIG. 8B shows the RT-PCR for CXCL10 (left) in BV-2 cells transfected with control or Stat1 siRNA for 24 hours and then stimulated with GCV for another 24 hours. Right shows efficiency of knockdown. FIG. 8C shows the RT-PCR for CXCL10 (left) and IFNβ (right) in wild type (wildtype) or Stat1 knockout (Stat1 KO) primary microglia treated with 200 µM GCV, monoGCV, diGCV or cGAMP for 6 hours. FIG. 8D shows the primary microglia from Stat1 knockout mice were treated with IFNγ and LPS with or without 200 µM GCV for 24 hours. RT-PCR shows indicated transcripts. Statistical tests: one-way ANOVA followed by Dunnett's multiple comparison test (FIGS. 8A, 8B) or unpaired Student's t-test (FIG. 8B right, FIGS. 8C, 8D).

FIG. 9A shows RT-PCR for CXCL10 in BV-2 cells treated for 24 hours with 200 µM GCV, diGCV or cGAMP along with 1 µM Jak inhibitors-Ruxolitinib (Rux) and TG101348 (TG). FIG. 9B shows RT-PCR for CXCL10 (left) in BV-2 cells transfected with Jak2 siRNA for 24 hours and then stimulated with GCV, diGCV or cGAMP for another 24 hours. Right shows efficiency of Jak2 knockdown. Statistical tests: one-way ANOVA followed by Dunnett's multiple comparison test or unpaired Student's t-test (FIG. 9B, right).

FIG. 11A shows the synthesis of the GCV-thiol derivative (Scheme 1). FIG. 11B shows labeling of the thiol group with biotin (Scheme 2). The product was characterized by $^1$H NMR (FIG. 11C), $^{13}$C NMR (FIG. 11D) and LCMS (FIG. 11E).

DETAILED DESCRIPTION

Figure 1A:
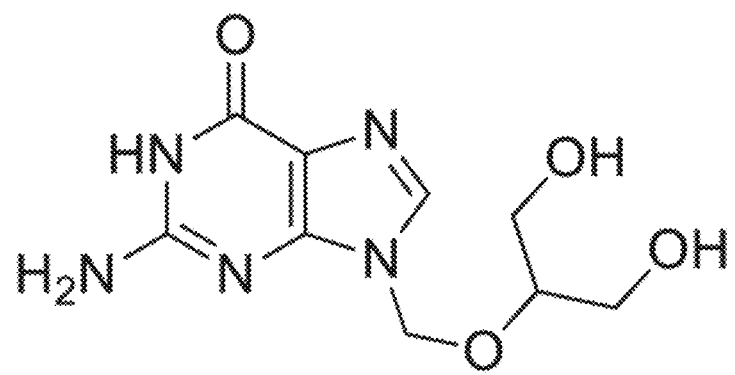
FIGS. 1A-1I show that Ganciclovir reduces inflammation and induces an interferon response in microglia.

The practice of the present invention will employ, unless otherwise indicated, conventional methods of medicine, pharmacology, chemistry, and biochemistry, within the skill of the art. Such techniques are explained fully in the literature. See, e.g., *Handbook of Neurochemistry and Molecular Neurobiology: Neuroimmunology* (Springer Reference, A. Lajtha, A. Galoyan, and H. Besedovsky eds., Springer, 3$^{rd}$ edition, 2007); *Clinical Neuroimmunology: Multiple Sclerosis and Related Disorders* (Current Clinical Neurology, S. A. Rizvi and P. K. Coyle eds., Humana Press, 2012); *Microglia in Health and Disease* (M. Tremblay, A. Sierra eds., Springer, 2014); *Microglia: Physiology, Regulation and Health Implications* (Neuroscience Research Progress, Nova Science Pub Inc., 2015); A. L. Lehninger, *Biochemistry* (Worth Publishers, Inc., current addition); Sambrook, et al., *Molecular Cloning: A Laboratory Manual* (3$^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. Definitions

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a derivative" includes a mixture of two or more derivatives, and the like.

The term "about," particularly in reference to a given quantity, is meant to encompass deviations of plus or minus five percent.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Inflammatory disorders" include diseases and conditions causing inflammation, such as autoimmune diseases, allergic responses, neurological disorders, such as neurodegenerative and neuroimmune diseases, cardiovascular diseases, cancer, infections, damaged tissue, or wounds. Inflammatory disorders include, but are not limited to, multiple sclerosis (MS), rheumatoid arthritis (RA), reactive arthritis, psoriasis, pemphigus vulgaris, Sjogren's disease, autoimmune thyroid disease (AITD), Hashimoto's thyroiditis, myasthenia gravis, diabetes mellitus type 1, stomatitis, lupus erythematosus, acute disseminated encephalomyelitis (ADEM), Addison's disease, agammaglobulinemia, alopecia areata, amyotrophic lateral sclerosis, ankylosing spondylitis, antiphospholipid syndrome, antisynthetase syndrome, atopic dermatitis, autoimmune aplastic anemia, autoimmune enteropathy, autoimmune hemolytic anemia, autoimmune hemolytic anemia, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behcet's disease, Berger's disease, Bickerstaffs encephalitis, Blau syndrome, Bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's Syndrome, cutaneous leukocytoclastic angiitis, Dego's disease, Dercum's disease, dermatitis herpetiformis, dermatomyositis, diffuse cutaneous systemic sclerosis, Dressler's syndrome, eczema, endometriosis, enthesitis-related arthritis, eosinophilic fasciitis, eosinophilic gastroenteritis, eosinophilic pneumonia, epidermolysis bullosa acquisita, erythema nodosum, erythroblastosis fetalis, essential mixed cryoglobulinemia, Evan's syndrome, fibrodysplasia ossificans progressiva, fibrosing alveolitis (or idiopathic pulmonary fibrosis), gastritis, gastrointestinal pemphigoid, glomerulonephritis, Goodpasture's syndrome, Graves' disease, Guillain-Barré syndrome (GBS), Hashimoto's encephalopathy, Henoch-Schonlein purpura, gestational pemphigoid, hidradenitis suppurativa, Hughes-Stovin syndrome, hypogammaglobulinemia, idiopathic inflammatory demyelinating diseases, idiopathic pulmonary fibrosis, IgA nephropathy, inclusion body myositis, chronic inflammatory demyelinating polyneuropathy, interstitial cystitis, juvenile idiopathic arthritis, Kawasaki's disease, Lambert-Eaton myasthenic syndrome, leukocytoclastic vasculitis, lichen planus, lichen sclerosus, linear IgA disease (LAD), lupoid hepatitis, Majeed syndrome, Ménière's disease, microscopic polyangiitis, Miller-Fisher syndrome, mixed connective tissue disease, morphea, Mucha-Habermann disease, microscopic colitis, myositis, narcolepsy, neuromyelitis optica, neuromyotonia, occular cicatricial pemphigoid, opsoclonus myoclonus syndrome, Ord's thyroiditis, palindromic rheumatism, PANDAS, paraneoplastic cerebellar degeneration, paroxysmal nocturnal hemoglobinuria (PNH), Parry Romberg syndrome, Parsonage-Turner syndrome, Pars planitis, pemphigus vulgaris, pernicious anaemia, perivenous encephalomyelitis, POEMS syndrome, polyarteritis *nodosa*, polymyalgia rheumatica, polymyositis, primary biliary cirrhosis, primary sclerosing cholangitis, progressive inflammatory neuropathy, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatic fever, sarcoidosis, Schmidt syndrome, Schnitzler syndrome, scleritis, scleroderma, serum sickness, Sjögren's syndrome, spondyloarthropathy, Still's disease, Stiff person syndrome, Subacute bacterial endocarditis (SBE), Susac's syndrome, Sweet's syndrome, Sydenham chorea, sympathetic ophthalmia, Takayasu's arteritis, temporal arteritis, thrombocytopenia, Tolosa-Hunt syndrome, transverse myelitis, undifferentiated connective tissue disease, undifferentiated spondyloarthropathy, urticarial vasculitis, vasculitis, vitiligo, Wegener's granulomatosis, autoimmune cardiomyopathy, ischemic heart disease, atherosclerosis, cancer, fibrosis, inflammatory bowel disease, inflammatory myopathy, giant cell arteritis (GCA), asthma, allergy, Parkinson's disease, schizophrenia, Alzheimer's disease, infections, sepsis and other conditions causing systemic inflammation.

In particular, inflammatory disorders include neurodegenerative and neuroimmune diseases, such as Alzheimer's disease, Huntington's disease, multiple sclerosis, acute disseminated encephalomyelitis, and meningitis, and other central nervous system diseases.

The terms "tumor," "cancer" and "neoplasia" are used interchangeably and refer to a cell or population of cells whose growth, proliferation or survival is greater than growth, proliferation or survival of a normal counterpart cell, e.g. a cell proliferative, hyperproliferative or differentiative disorder. Typically, the growth is uncontrolled. The term "malignancy" refers to invasion of nearby tissue. The term "metastasis" or a secondary, recurring or recurrent tumor, cancer or neoplasia refers to spread or dissemination of a tumor, cancer or neoplasia to other sites, locations or regions within the subject, in which the sites, locations or regions are distinct from the primary tumor or cancer. Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission. In particular, the terms "tumor," "cancer" and "neoplasia" include carcinomas, such as squamous cell carcinoma, adenocarcinoma, adenosquamous carcinoma, anaplastic carcinoma, large cell carcinoma, and small cell carcinoma. These terms include, but are not limited to, breast cancer, prostate cancer, lung cancer, ovarian cancer, testicular cancer, colon cancer, pancreatic cancer, gastric cancer, hepatic cancer, leukemia, lymphoma, adrenal cancer, thyroid cancer, pituitary cancer, renal cancer, brain cancer, skin cancer, head cancer, neck cancer, oral cavity cancer, tongue cancer, and throat cancer.

The terms "neurological disorder" and "neurological disease" include, but are not limited to, acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Alzheimer's disease; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; Dandy-Walker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Kearns-Sayre syndrome; Kennedy disease Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease—neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocal leukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina *bifida*; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome.

An "effective amount" of a GCV derivative (e.g., GCV-PEG monomer, GCV-PEG dimer, or thiol-GCV dimer) is an amount sufficient to effect beneficial or desired results, such as an amount that activates STING, decreases inflammation, decreases microglial nitric oxide production, decreases the microglial inflammatory response, or induces a type I interferon response. An effective amount can be administered in one or more administrations, applications, or dosages.

By "therapeutically effective dose or amount" of a GCV derivative (e.g., GCV-PEG monomer, GCV-PEG dimer, or thiol-GCV dimer) is intended an amount that, when administered as described herein, brings about a positive therapeutic response with respect to treatment of an individual for an immune-related disorder, such as inflammation, autoimmunity, or an infection, or a neurological disorder, or cancer. By "positive therapeutic response" is intended that the individual undergoing treatment exhibits an improvement in one or more symptoms of the immune-related disorder, neurological disorder, or cancer for which the individual is undergoing therapy, such as a reduction in inflammation, pain, autoimmune-induced tissue damage, or prolonged survival. A therapeutically effective dose or amount may also decrease neuroinflammation and/or systemic inflammation. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) increasing survival time; (b) decreasing the risk of death due to the disease; (c) preventing the disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease.

"Substantially purified" generally refers to isolation of a substance (e.g., compound, molecule, agent) such that the substance comprises the majority percent of the sample in which it resides. Typically in a sample, a substantially purified component comprises 50%, preferably 80%-85%, more preferably 90-95% of the sample.

The terms "subject," "individual," and "patient," are used interchangeably herein and refer to any mammalian subject for whom diagnosis, prognosis, treatment, or therapy is desired, particularly humans. Other subjects may include cattle, dogs, cats, guinea pigs, rabbits, rats, mice, horses, and so on. In some cases, the methods of the invention find use in experimental animals, in veterinary application, and in the development of animal models for disease, including, but not limited to, rodents including mice, rats, and hamsters; primates, and transgenic animals.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery that GCV derivatives are useful in treating inflammation, including neuroinflammation and systemic inflammation. In particular, GCV derivatives, including a GCV-PEG monomer, GCV-PEG dimer, and thiol-GCV dimer were shown to have anti-inflammatory activity in microglia and induce an antiviral interferon response (see Example 1).

In order to further an understanding of the invention, a more detailed discussion is provided below regarding GCV derivatives and their use in modulating innate and adaptive immunity in a subject and treating immune-related disorders, including inflammation, autoimmunity, and infections, and neurological disorders, and cancer.

A. GCV Derivatives

GCV derivatives that can be used in the practice of the invention include various analogues of GCV, having the chemical formula:

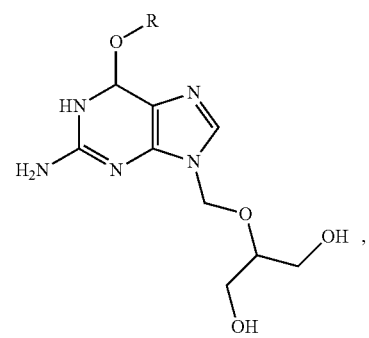

or a pharmaceutically acceptable salt thereof, wherein R is a polyethylene glycol, a propanethiol, 2-[(2-Amino-6-{2-[2-(2-ethoxyethoxy)ethoxy]ethoxy}-6,9-dihydro-1H-purin-9-yl)methoxy]-1,3-propanediol, or 2-({2-Amino-6-[3-(propyldithio)propoxy]-6,9-dihydro-1H-purin-9-yl}methoxy)-1,3-propanediol.

In one embodiment, the GCV derivative comprises a GCV-PEG monomer (2-{[2-Amino-6-(2-{2-[2-(2-hydroxyethoxy)ethoxy]ethoxy}ethoxy)-6,9-dihydro-1H-purin-9-yl]methoxy}-1,3-propanediol) having the formula:

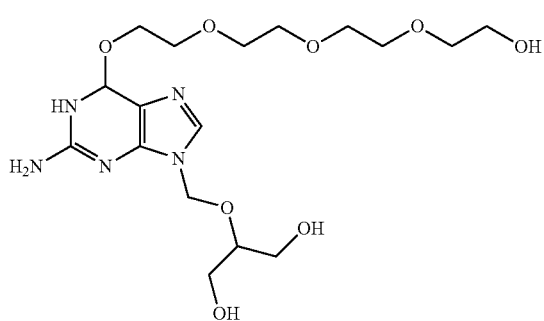

or a pharmaceutically acceptable salt thereof.

In another embodiment, the GCV derivative comprises a GCV-PEG dimer (2-({2-Amino-6-[2-(2-{2-[2-(2-amino-9-{[2-hydroxy-1-(hydroxymethyl)ethoxy]methyl}-9H-purin-6-yloxy)ethoxy]ethoxy}ethoxy)ethoxy]-6,9-dihydro-1H-purin-9-yl}methoxy)-1,3-propanediol) having the formula:

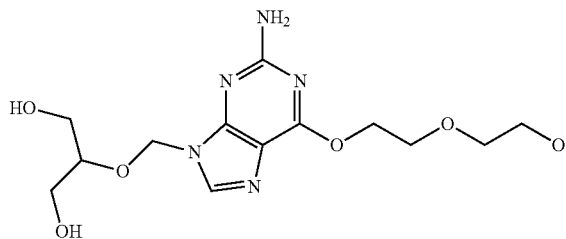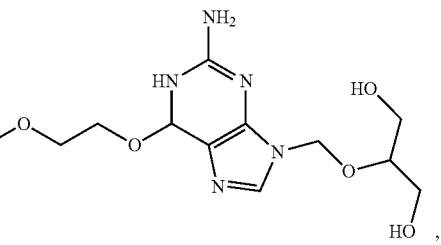

or a pharmaceutically acceptable salt thereof.

In another embodiment, the GCV derivative comprises a thiol-GCV dimer (2-[(2-Amino-6-{3-[3-(2-amino-9-{[2-hydroxy-1-(hydroxymethyl)ethoxy]methyl}-6,9-dihydro-1H-purin-6-yloxy)propyldithio]propoxy}-6,9-dihydro-1H-purin-9-yl)methoxy]-1,3-propanediol) having the formula:

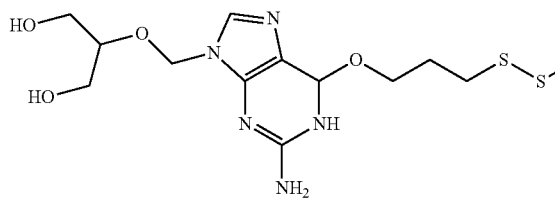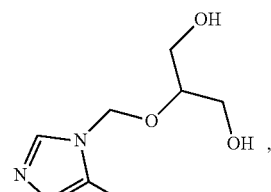

or a pharmaceutically acceptable salt thereof.

Such GCV derivatives decrease inflammation, including neuroinflammation and systemic inflammation. In particular, GCV derivatives have the ability to activate STING, induce a type I interferon response, and decrease a microglial inflammatory response, including reducing microglial proliferation, nitric oxide production, and neuroinflammation.

B. Pharmaceutical Compositions

GCV derivatives (e.g., GCV-PEG monomer, GCV-PEG dimer, and thiol-GCV dimer) can be formulated into pharmaceutical compositions optionally comprising one or more pharmaceutically acceptable excipients. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient.

Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition of the invention can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the GCV derivative, or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the GCV derivative (e.g., when contained in a drug delivery system) in the composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for oral, ocular, or localized delivery.

The pharmaceutical preparations herein can also be housed in a syringe, an implantation device, or the like, depending upon the intended mode of delivery and use. Preferably, the compositions comprising one or more GCV derivatives (e.g., GCV-PEG monomer, GCV-PEG dimer, and thiol-GCV dimer) described herein are in unit dosage form, meaning an amount of a conjugate or composition of the invention appropriate for a single dose, in a premeasured or pre-packaged form.

The compositions herein may optionally include one or more additional agents, such as other drugs for treating an inflammatory disorder, a neurodegenerative disease, a neuroimmune disease, an autoimmune disease, cancer, an infection, or systemic inflammation, such as, but not limited to, anti-inflammatory/analgesic agents, including, but not limited to, non-steroidal anti-inflammatory drugs (NSAIDs), such as aspirin, ibuprofen, and naproxen, paracetamol, acetaminophen, COX-2 inhibitors, such as rofecoxib, celecoxib, and etoricoxib; opioids, such as morphine, codeine, oxycodone, hydrocodone, dihydromorphine, pethidine; and immune selective anti-inflammatory derivatives (ImSAIDs); immunosuppressive agents, such as steroidal agents (e.g., prednisone) or non-steroidal agents (e.g., sirolimus (Rapamune, Wyeth-Ayerst Canada), tacrolimus (Prograf, Fujisawa Canada), anti-IL2R daclizumab (Zenapax, Roche Canada), 15-deoxyspergualin, cyclosporin, methotrexate, rapamycin, Rapamune (sirolimus/rapamycin), FK506, and Lisofylline (LSF); and or other medications used to treat a subject for a condition or disease. Alternatively, such agents can be contained in a separate composition from the composition comprising a GCV derivative (e.g., GCV-PEG monomer, GCV-PEG dimer, and thiol-GCV dimer) and co-administered concurrently, before, or after the composition comprising a GCV derivative.

C. Administration

At least one therapeutically effective cycle of treatment with a GCV derivative (e.g., GCV-PEG monomer, GCV-PEG dimer, and thiol-GCV dimer) will be administered to a subject for treatment of an immune-related disorder, such as inflammation, autoimmunity, or an infection, or a neurological disorder, or cancer. GCV derivatives can be used for decreasing inflammation such as caused by an autoimmune disease, an allergic response, a neurological disease, such as a neurodegenerative disease or neuroimmune disease, a cardiovascular disease, cancer, an infection, damaged tissue, or a wound. Inflammatory disorders that can be treated by the methods of the invention include, but are not limited to, multiple sclerosis (MS), rheumatoid arthritis (RA), reactive arthritis, psoriasis, pemphigus vulgaris, Sjogren's disease, autoimmune thyroid disease (AITD), Hashimoto's thyroiditis, myasthenia gravis, diabetes mellitus type 1, stomatitis, lupus erythematosus, acute disseminated encephalomyelitis (ADEM), Addison's disease, agammaglobulinemia, alopecia areata, amyotrophic lateral sclerosis, ankylosing spondylitis, antiphospholipid syndrome, antisynthetase syndrome, atopic dermatitis, autoimmune aplastic anemia, autoimmune enteropathy, autoimmune hemolytic anemia, autoimmune hemolytic anemia, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behcet's disease, Berger's disease, Bickerstaff's encephalitis, Blau syndrome, Bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's Syndrome, cutaneous leukocytoclastic angiitis, Dego's disease, Dercum's disease, dermatitis herpetiformis, dermatomyositis, diffuse cutaneous systemic sclerosis, Dressler's syndrome, eczema, endometriosis, enthesitis-related arthritis, eosinophilic fasciitis, eosinophilic gastroenteritis, eosinophilic pneumonia, epidermolysis bullosa acquisita, erythema nodosum, erythroblastosis fetalis, essential mixed cryoglobulinemia, Evan's syndrome, fibrodysplasia ossificans progressiva, fibrosing alveolitis (or idiopathic pulmonary fibrosis), gastritis, gastrointestinal pemphigoid, glomerulonephritis, Goodpasture's syndrome, Graves' disease, Guillain-Barré syndrome (GBS), Hashimoto's encephalopathy, Henoch-Schonlein purpura, gestational pemphigoid, hidradenitis suppurativa, Hughes-Stovin syndrome, hypogammaglobulinemia, idiopathic inflammatory demyelinating diseases, idiopathic pulmonary fibrosis, IgA nephropathy, inclusion body myositis, chronic inflammatory demyelinating polyneuropathy, interstitial cystitis, juvenile idiopathic arthritis, Kawasaki's disease, Lambert-Eaton myasthenic syndrome, leukocytoclastic vasculitis, lichen planus, lichen sclerosus, linear IgA disease (LAD), lupoid hepatitis, Majeed syndrome, Ménière's disease, microscopic polyangiitis, Miller-Fisher syndrome, mixed connective tissue disease, morphea, Mucha-Habermann disease, microscopic colitis, myositis, narcolepsy, neuromyelitis optica, neuromyotonia, occular cicatricial pemphigoid, opsoclonus myoclonus syndrome, Ord's thyroiditis, palindromic rheumatism, PANDAS, paraneoplastic cerebellar degeneration, paroxysmal nocturnal hemoglobinuria (PNH), Parry Romberg syndrome, Parsonage-Turner syndrome, Pars planitis, pemphigus vulgaris, pernicious anaemia, perivenous encephalomyelitis, POEMS syndrome, polyarteritis *nodosa*, polymyalgia rheumatica, polymyositis, primary biliary cirrhosis, primary sclerosing cholangitis, progressive inflammatory neuropathy, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatic fever, sarcoidosis, Schmidt syndrome, Schnitzler syndrome, scleritis, scleroderma, serum sickness, Sjögren's syndrome, spondyloarthropathy, Still's disease, Stiff person syndrome, Subacute bacterial endocarditis (SBE), Susac's syndrome, Sweet's syndrome, Sydenham chorea, sympathetic ophthalmia, Takayasu's arteritis, temporal arteritis, thrombocytopenia, Tolosa-Hunt syndrome, transverse myelitis, undifferentiated connective tissue disease, undifferentiated spondyloarthropathy, urticarial vasculitis, vasculitis, vitiligo, Wegener's granulomatosis, autoimmune cardiomyopathy, ischemic heart disease, atherosclerosis, cancer, fibrosis, inflammatory bowel disease, inflammatory myopathy, giant cell arteritis (GCA), asthma, allergy, Parkinson's disease, schizophrenia, Alzheimer's disease, an infection, and sepsis and other conditions causing systemic inflammation.

In particular, inflammatory disorders include neurodegenerative and neuroimmune diseases, such as Alzheimer's disease, Huntington's disease, multiple sclerosis, acute disseminated encephalomyelitis, and meningitis, and other central nervous system diseases.

By "therapeutically effective dose or amount" of a GCV derivative is intended an amount that, when administered as described herein, brings about a positive therapeutic response such as improved recovery from an immune-related disorder, such as inflammation, autoimmunity, or an infection, or a neurological disorder, or cancer. Improved recovery may include a reduction in inflammation, pain, or autoimmune-induced tissue damage, or prolonged survival. Additionally, a GCV derivative may activate the STING pathway, decrease the microglial inflammatory response, decrease microglial nitric oxide production, reduce microglial proliferation, inhibit inflammatory factors (e.g., iNOS and CCL2), and/or activate a type I interferon response (e.g., induce IFN-β and CXCL10 in microglia and monocytes). In the case of an inflammatory disorder, a therapeutically effective dose or amount may decrease neuroinflammation and/or systemic inflammation.

In certain embodiments, multiple therapeutically effective doses of compositions comprising one or more GCV derivatives (e.g., GCV-PEG monomer, GCV-PEG dimer, and thiol-GCV dimer), and/or one or more other therapeutic agents, such as other drugs for treating an inflammatory disorder, a neurodegenerative disease, a neuroimmune disease, an autoimmune disease, cancer, an infection, or systemic inflammation, such as, but not limited to, anti-inflammatory/analgesic agents, including, but not limited to, non-steroidal anti-inflammatory drugs (NSAIDs), such as aspirin, ibuprofen, and naproxen, paracetamol, acetaminophen, COX-2 inhibitors, such as rofecoxib, celecoxib, and etoricoxib; opioids, such as morphine, codeine, oxycodone, hydrocodone, dihydromorphine, pethidine; and immune selective anti-inflammatory derivatives (ImSAIDs); immunosuppressive agents, such as steroidal agents (e.g., prednisone) or non-steroidal agents (e.g., sirolimus (Rapamune, Wyeth-Ayerst Canada), tacrolimus (Prograf, Fujisawa Canada), anti-IL2R daclizumab (Zenapax, Roche Canada), 15-deoxyspergualin, cyclosporin, methotrexate, rapamycin, Rapamune (sirolimus/rapamycin), FK506, and Lisofylline (LSF); or other medications will be administered. Compositions may be administered in accordance with any medically acceptable method known in the art. The compositions are typically, although not necessarily, administered orally, via injection (subcutaneously, intravenously, or intramuscularly), by infusion, or locally. Additional modes of administration are also contemplated, such as intralesion, intraparenchymatous, pulmonary, rectal, transdermal, transmucosal, intrathecal, pericardial, intra-arterial, intraocular, intraperitoneal, and so forth.

The preparations according to the invention are also suitable for local treatment. In a particular embodiment, a composition of the invention is used for localized delivery of a GCV derivative, for example, for the treatment of an inflammatory disorder. For example, compositions may be administered locally to treat inflamed tissues. The particular preparation and appropriate method of administration can be chosen to target the GCV derivative to microglia in the central nervous system.

The pharmaceutical preparation can be in the form of a liquid solution or suspension immediately prior to administration, but may also take another form such as a syrup, cream, ointment, tablet, capsule, powder, gel, matrix, suppository, or the like. The pharmaceutical compositions comprising one or more GCV derivatives and other agents may be administered using the same or different routes of administration in accordance with any medically acceptable method known in the art.

In another embodiment of the invention, the pharmaceutical compositions comprising one or more GCV derivatives and/or other agents are in a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

The invention also provides a method for administering a conjugate comprising a GCV derivative as provided herein to a patient suffering from a condition that is responsive to treatment with a GCV derivative contained in the conjugate or composition. The method comprises administering, via any of the herein described modes, a therapeutically effective amount of the conjugate or drug delivery system, preferably provided as part of a pharmaceutical composition. The method of administering may be used to treat any condition that is responsive to treatment with a GCV derivative. More specifically, the compositions herein are effective in treating inflammatory disorders.

Those of ordinary skill in the art will appreciate which conditions a specific GCV derivative can effectively treat. The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case.

A purified GCV derivative (again, preferably provided as part of a pharmaceutical preparation) can be administered alone or in combination with one or more other therapeutic agents, such as other drugs for treating an inflammatory disorder, a neurodegenerative disease, a neuroimmune disease, an autoimmune disease, cancer, an infection, or systemic inflammation, or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. In certain embodiments, multiple therapeutically effective doses of the GCV derivative and/or other therapeutic agents will be administered according to a daily dosing regimen or intermittently. For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, and so forth. For example, in some embodiments, the GCV derivative will be administered twice-weekly or thrice-weekly for an extended period of time, such as for 1, 2, 3, 4, 5, 6, 7, 8 . . . 10 . . . 15 . . . 24 weeks, and so forth. By "twice-weekly" or "two times per week" is intended that two therapeutically effective doses of the agent in question is administered to the subject within a 7 day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7 day period, allowing for a minimum of 48 hours between doses and a maximum of 72 hours between doses. For purposes of the present invention, this type of dosing is referred to as "intermittent" therapy. In accordance with the methods of the present invention, a subject can receive intermittent therapy (i.e., twice-weekly or thrice-weekly administration of a therapeutically effective dose) for one or more weekly cycles until the desired therapeutic response is achieved. Preferred compositions are those requiring dosing no more than once a day.

A GCV derivative can be administered prior to, concurrent with, or subsequent to other agents. If provided at the same time as other agents, one or more GCV derivatives can be provided in the same or in a different composition. Thus, one or more GCV derivatives and other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising a GCV derivative and a dose of a pharmaceutical composition comprising at least one other agent, such as another GCV derivative or drug for treating an inflammatory disorder, which in combination comprise a therapeutically effective dose, according to a particular dosing regimen. Similarly, one or more GCV derivatives and one or more other therapeutic agents can be administered in at least one therapeutic dose. Administration of the separate pharmaceutical compositions can be performed simultaneously or at different times (i.e., sequentially, in either order, on the same day, or on different days), as long as the therapeutic effect of the combination of these substances is caused in the subject undergoing therapy.

C. Kits

The invention also provides kits comprising one or more containers holding compositions comprising at least one GCV derivative (e.g., GCV-PEG monomer, GCV-PEG dimer, and thiol-GCV dimer) and optionally one or more other agents for treating an inflammatory disorder, a neurodegenerative disease, a neuroimmune disease, an autoimmune disease, cancer, an infection, or systemic inflammation. Compositions can be in liquid form or can be lyophilized. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery devices. The delivery device may be pre-filled with the compositions.

The kit can also comprise a package insert containing written instructions for methods of using the compositions comprising GCV derivatives for treating a subject for an inflammatory disorder, a neurodegenerative disease, a neuroimmune disease, an autoimmune disease, cancer, an infection, or systemic inflammation. The package insert can be an unapproved draft package insert or can be a package insert approved by the Food and Drug Administration (FDA) or other regulatory body.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Figure 1B:
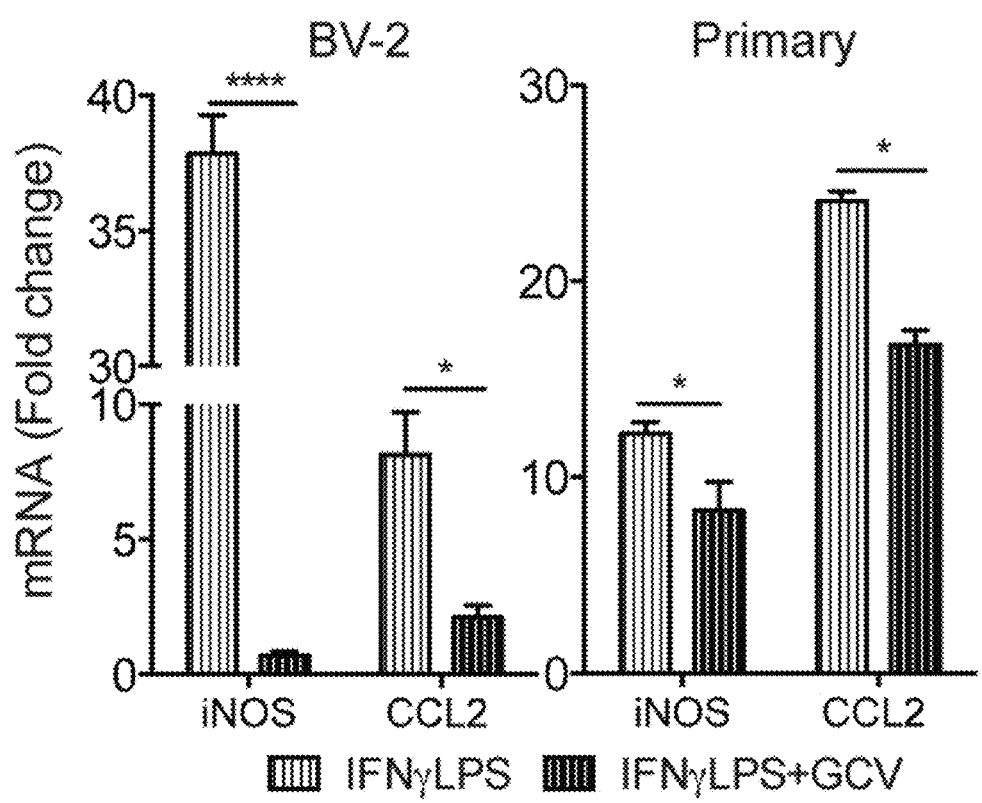
Figure 1C:
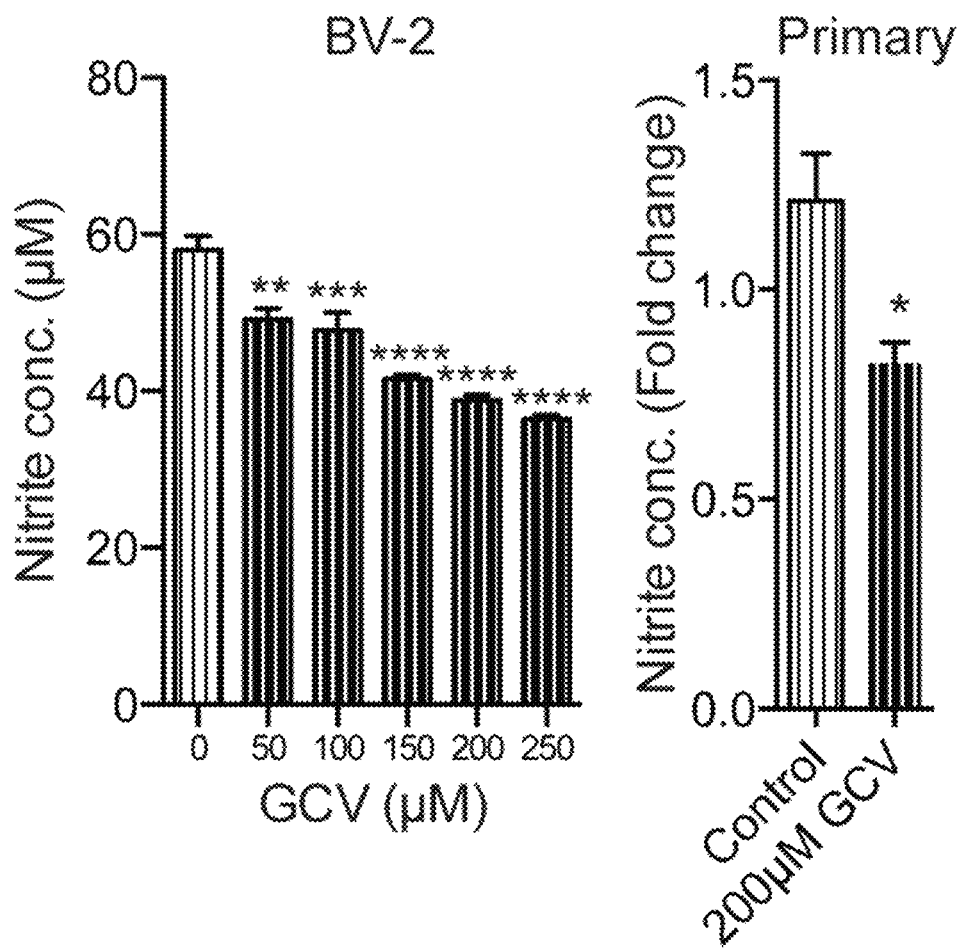
Figure 1D:
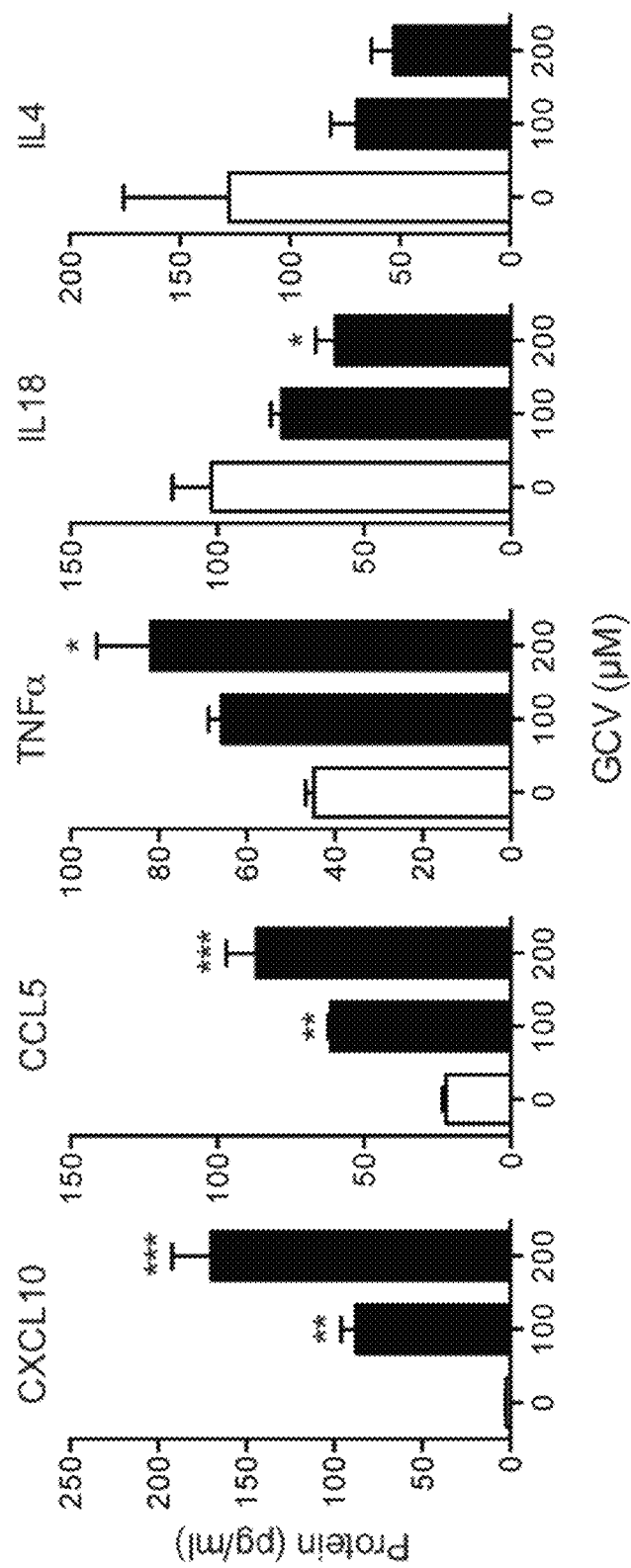
Figure 1E:
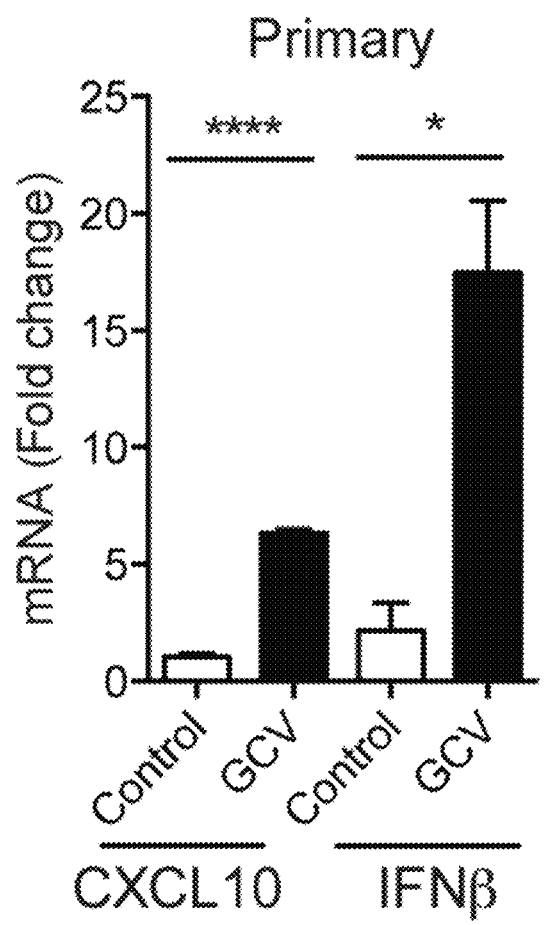
Figure 1F:
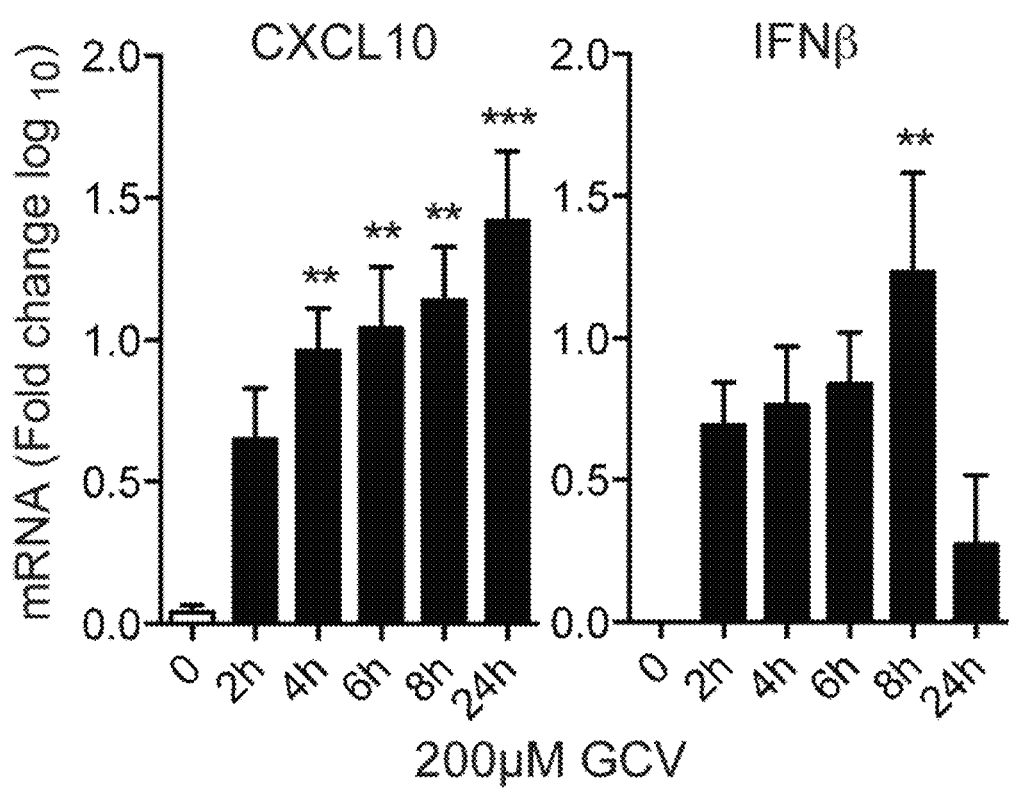
Figure 1G:
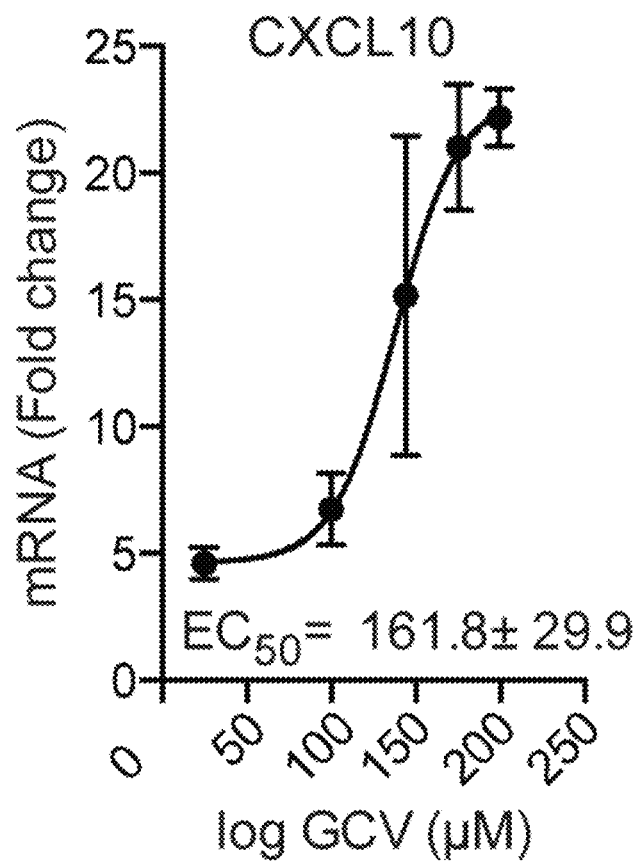
Figure 1H:
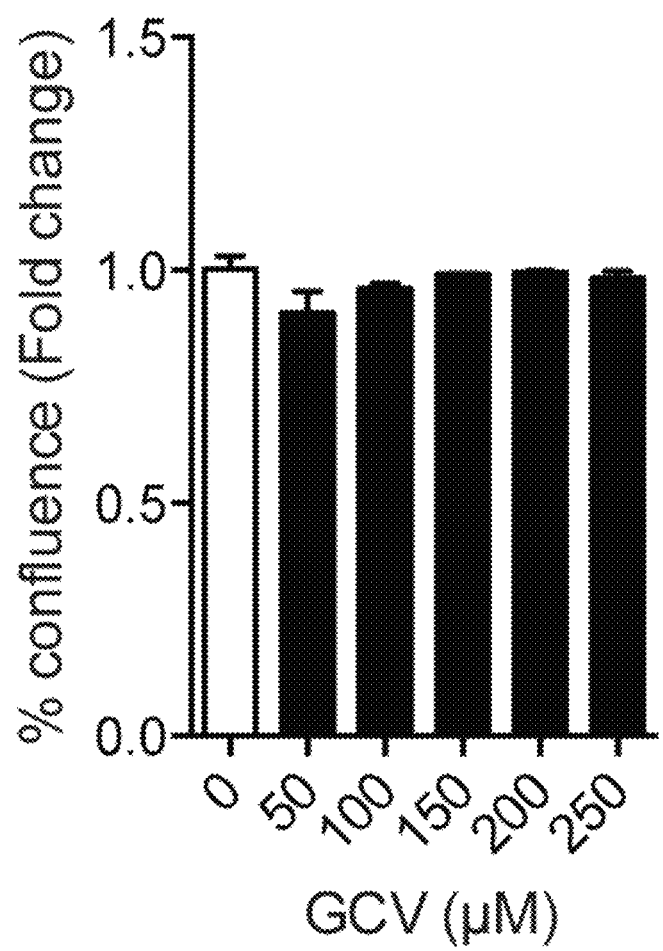

Ganciclovir Suppresses Brain Inflammation by Activating a Type I Interferon Response Via STING Introduction Ganciclovir (GCV; FIG. 1A) and other nucleoside analogs of 2'-deoxyguanosine are anti-viral drugs used as effective treatments for herpes virus infections (Faulds et al. (1990) Drugs 39:597-638). We recently reported that GCV, at therapeutic doses equivalent to those in humans, ameliorates the disease course and pathology in a mouse model for multiple sclerosis, called experimental autoimmune encephalomyelitis (EAE) (Ding et al. (2014) J Exp Med 211:189-198). GCV exerted these effects, in part, by reducing inflammation and inhibiting the proliferation of microglia, the immune cells of the CNS (Ding et al., supra). To understand the molecular basis of this activity, we stimulated the murine microglial cell line BV-2 and primary microglia with IFNγ and LPS and treated them with GCV at doses achieved in patients (see Methods). Remarkably, this led to an almost complete transcriptional inhibition of the inflammatory factors, iNOS and CCL2 (FIG. 1B) and reduction in neurotoxic microglial nitric oxide production (FIG. 1C). In the absence of exogenous stimulation, GCV prominently changed the expression of several secreted signaling proteins, measured with an unbiased antibody-based multiplex assay, significantly increasing interferon gamma-induced protein 10 (or CXCL10), CCL5, TNFα, and IL-22, while decreasing IL-18 in BV-2 culture supernatants (FIG. 1D and Table 1). The most prominently increased protein, CXCL10, was also increased at the transcriptional level by GCV in a dose and time-dependent manner without causing any toxicity with $EC_{50}$~160 µM (FIGS. 1F-1H), hence we conclude that these immune modulatory effects of GCV are unlikely due to growth inhibition or cell death. This signature, we noticed, resembled the interferon response of virus-infected cells (Borden et al. (2007) Nat Rev Drug Discov 6:975-990). Thus, we confirmed that GCV induced IFNβ as well (FIGS. 1E-1F).

Figure 1I:
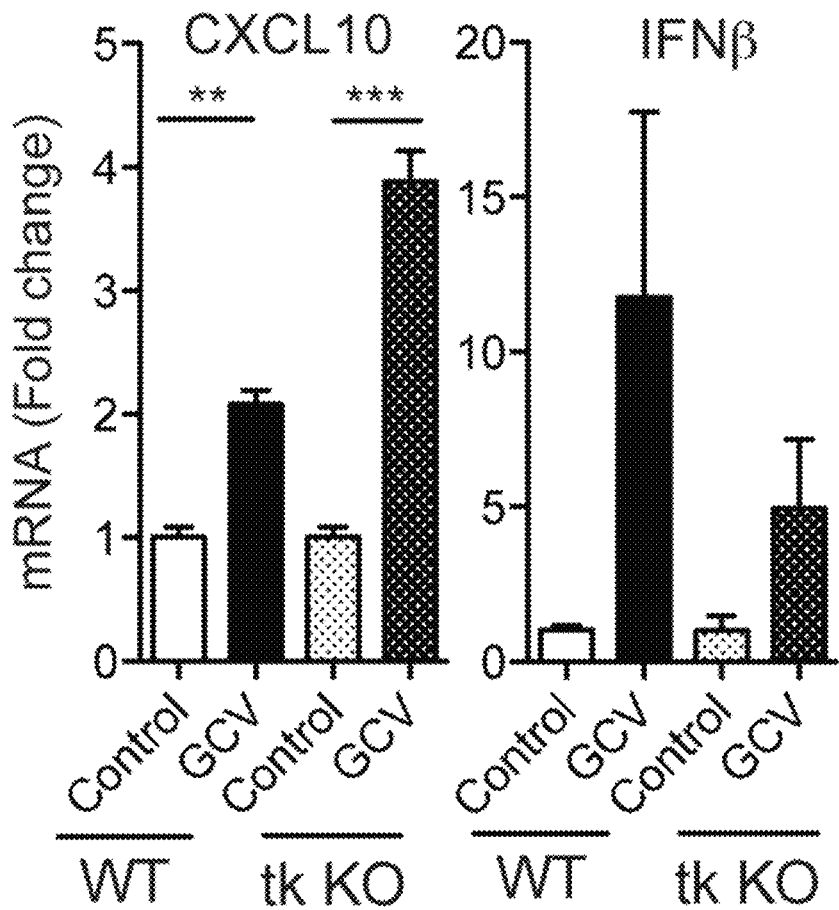
Figure 5:
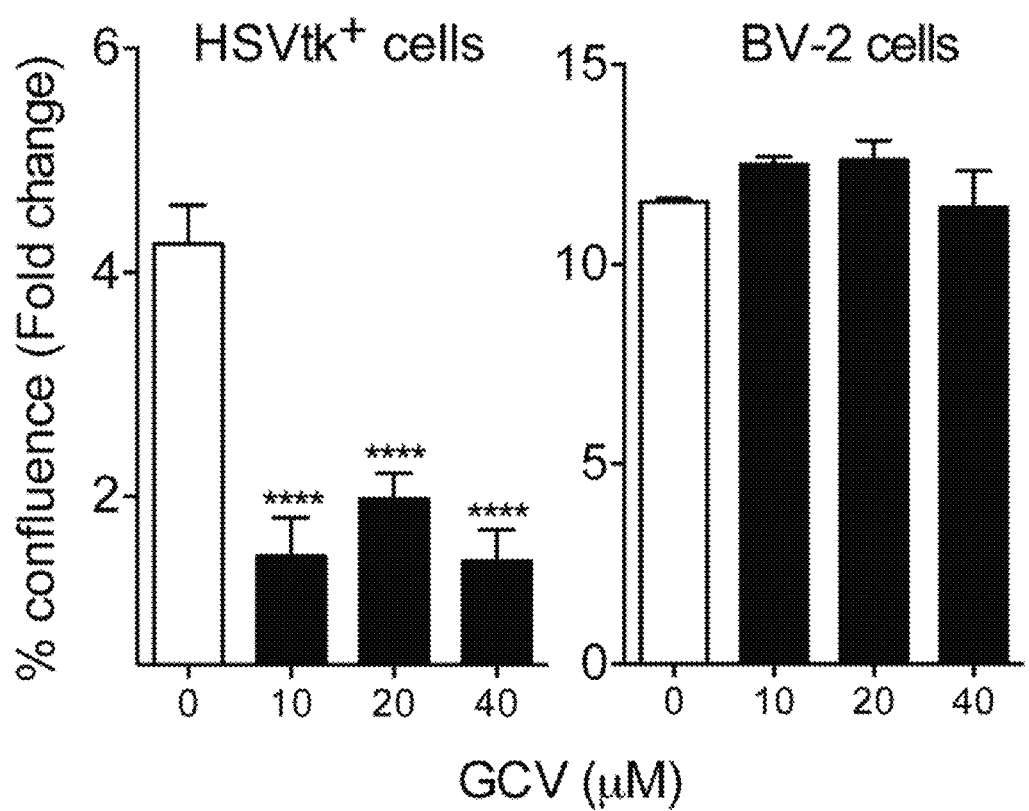
FIG. 5 shows that BV-2 cells are HSVtk$^-$. Cells stably expressing HSVtk and BV-2 cells used in this study were treated with indicated concentrations of GCV for 48 hours. Percent confluence measured using automated cell counting. Fold change is based on confluence at 0 hours. Statistical test: one-way ANOVA followed by Dunnett's multiple comparison test.

In its canonical mechanism of action, GCV is phosphorylated by viral thymidine kinases (e.g. Herpes Simplex Virus type 1 thymidine kinase, HSVtk) and incorporated into cellular DNA thereby inhibiting replication (Littler et al. (1992) Nature 358:160-162; Matthews et al. (1988) Rev Infect Dis 10 Suppl 3:S490-494). In contrast, the production of CXCL10 and IFNβ by GCV does not require HSVtk or endogenous tk. Cells used in this study did not express viral tk confirmed by cell death assay (FIG. 5). Additionally, microglia isolated from adult tk1 knockout mice treated with GCV produced CXCL10 and IFNβ mRNA at levels seen in treated wild type microglia (FIG. 1I).

Figure 2A:
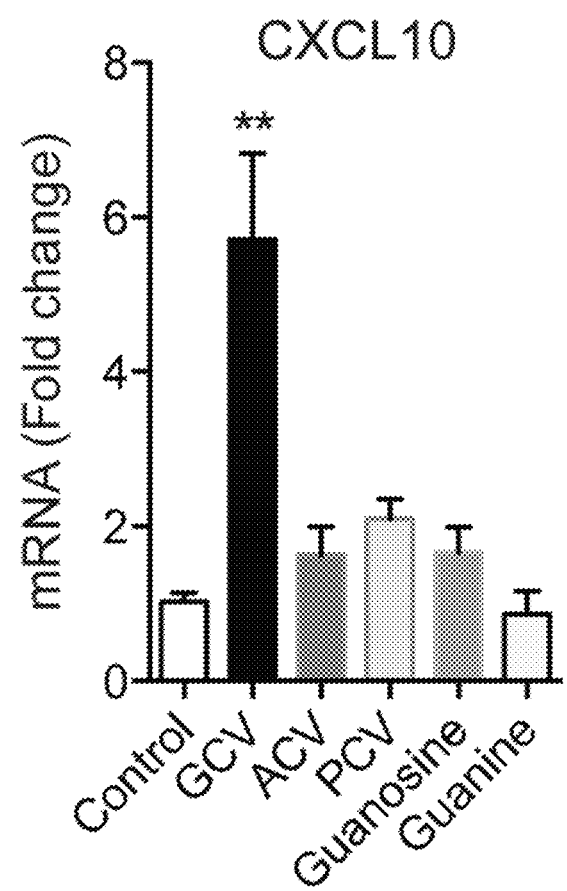
FIGS. 2A-2F show that novel GCV derivatives are potent inducers of an interferon response.
Figure 2B:
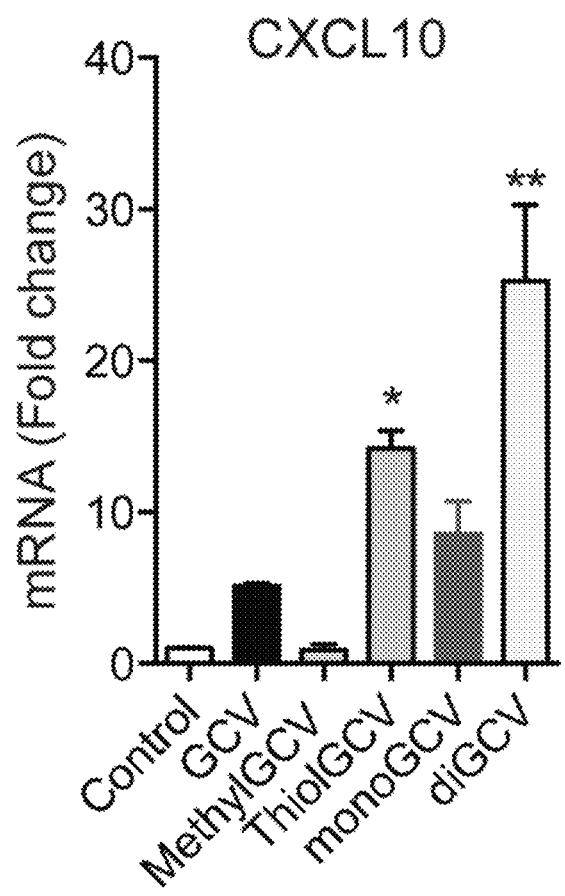
Figure 2C:
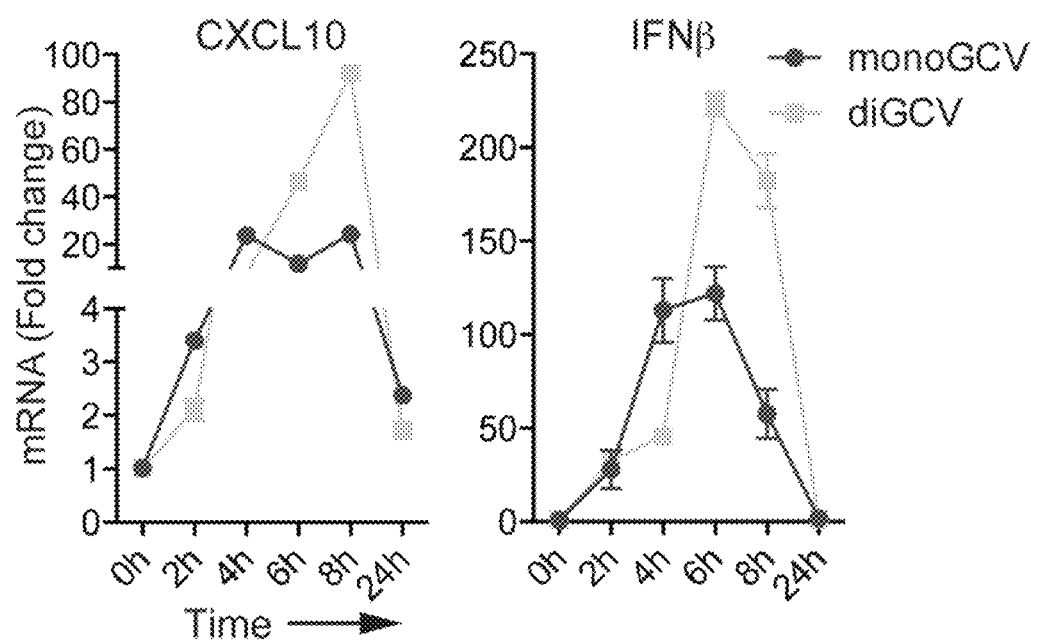
Figure 2D:
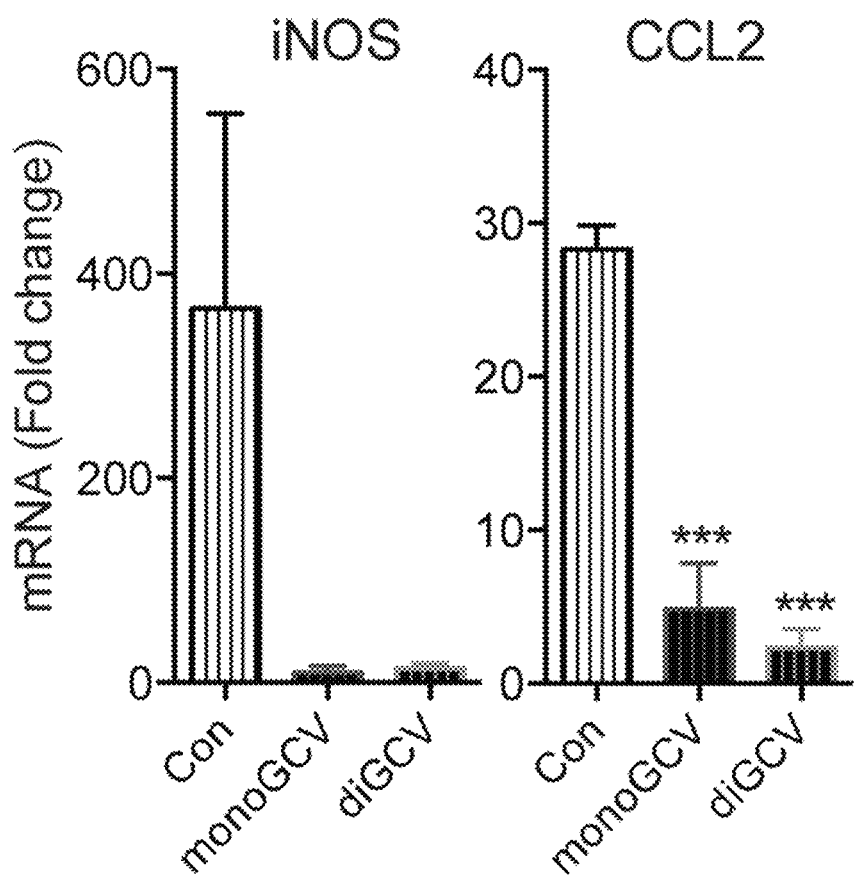
Figure 2E:
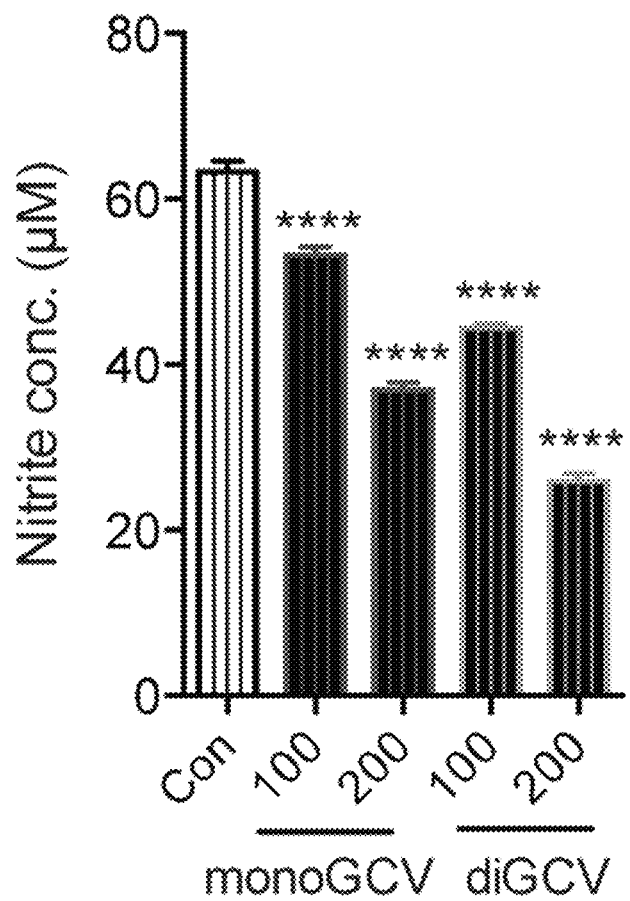
Figure 2F:
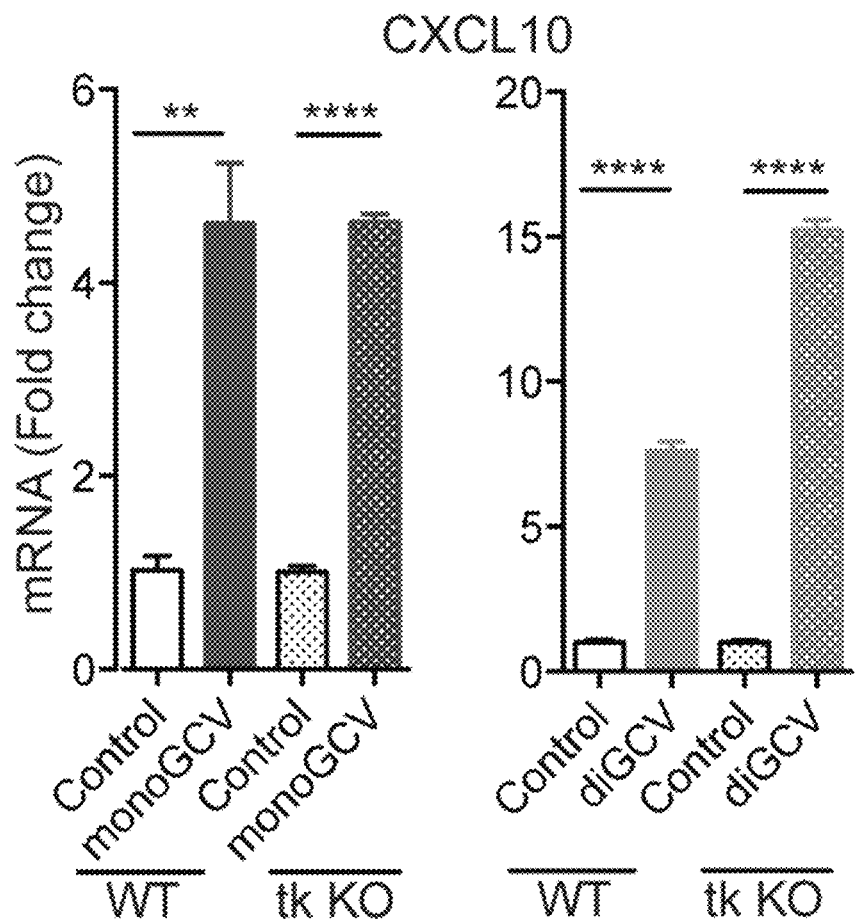
Figure 6A:
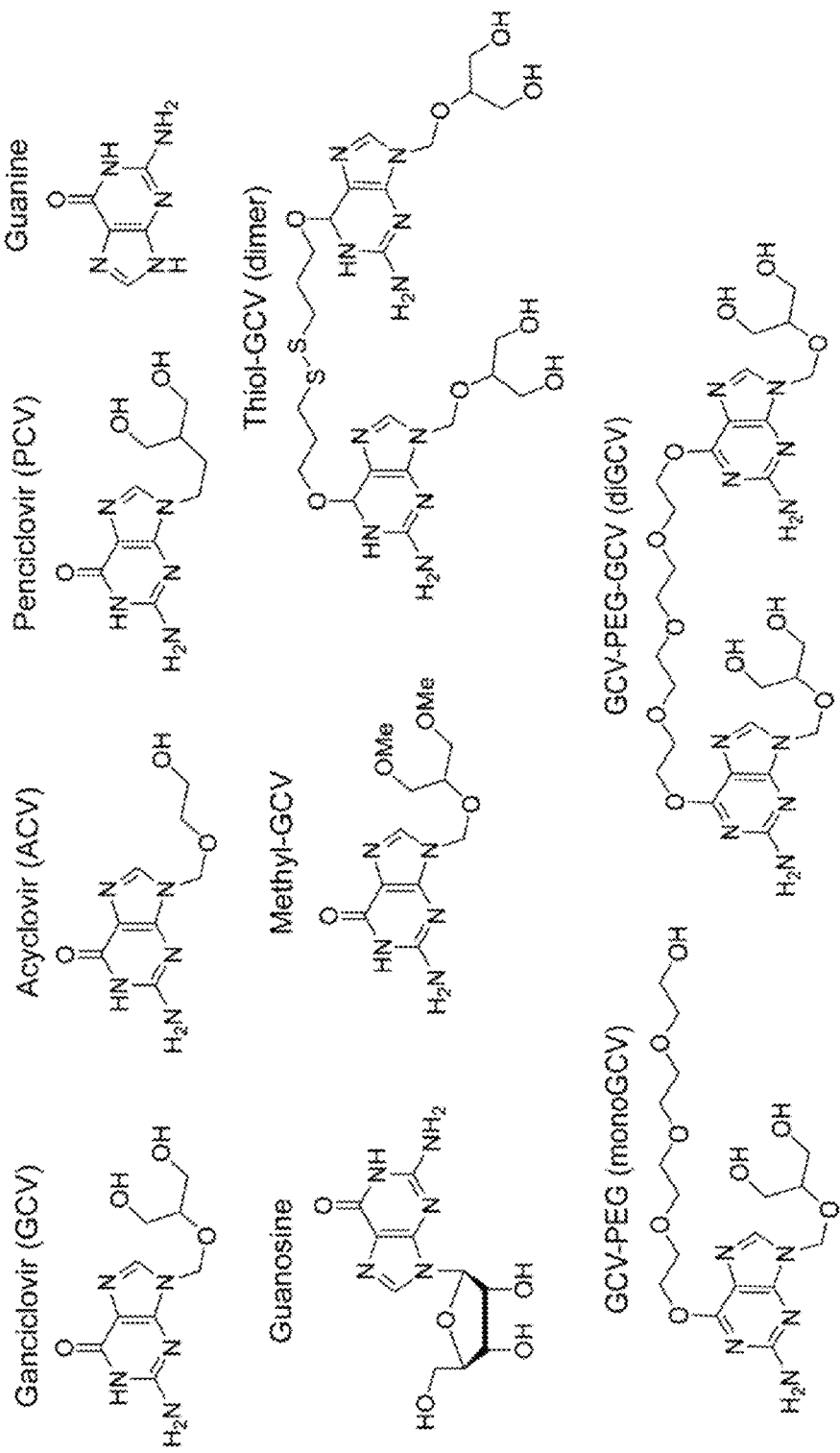
FIGS. 6A and 6B show structures of the compounds used in this study.
Figure 6B:
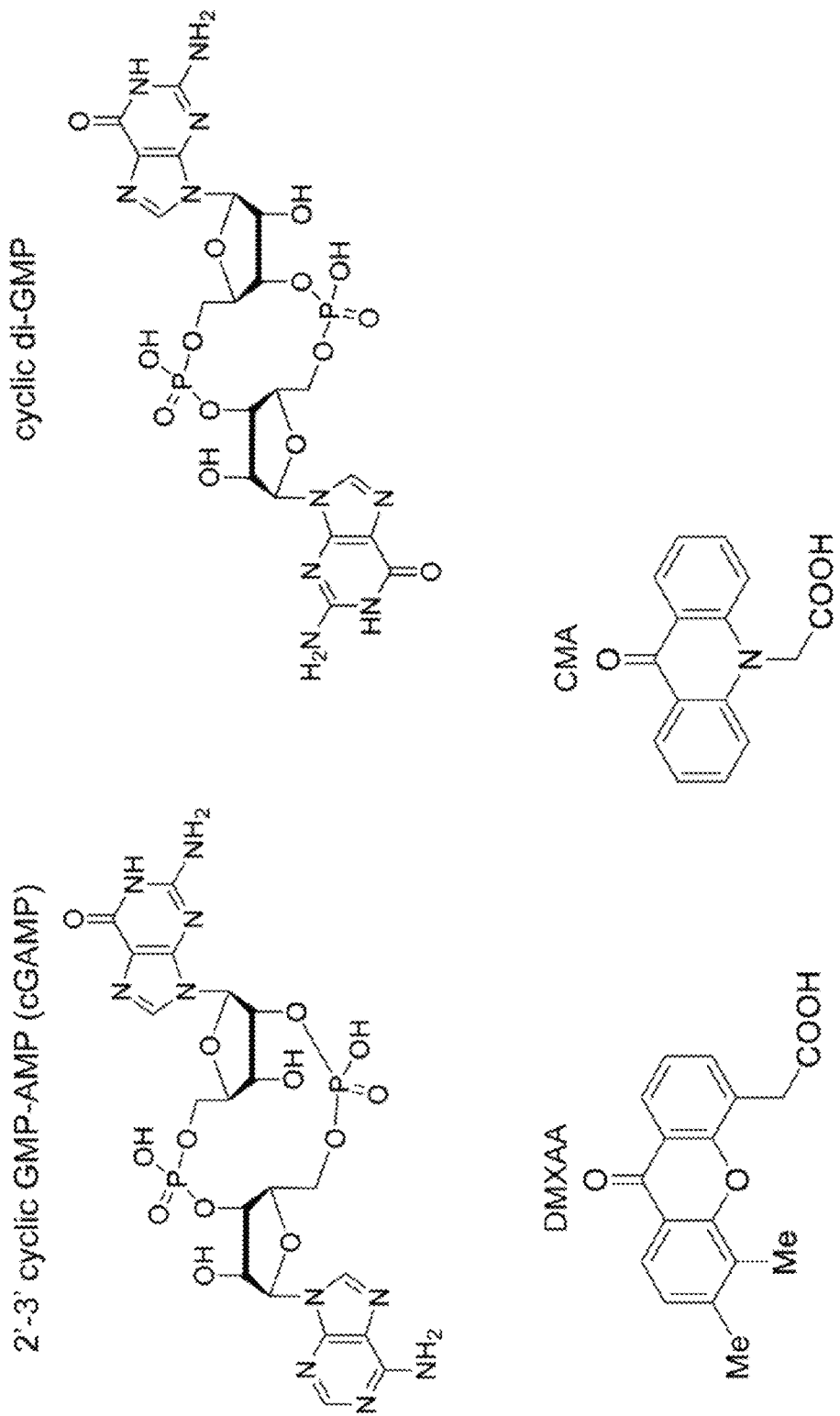
Figure 7A:
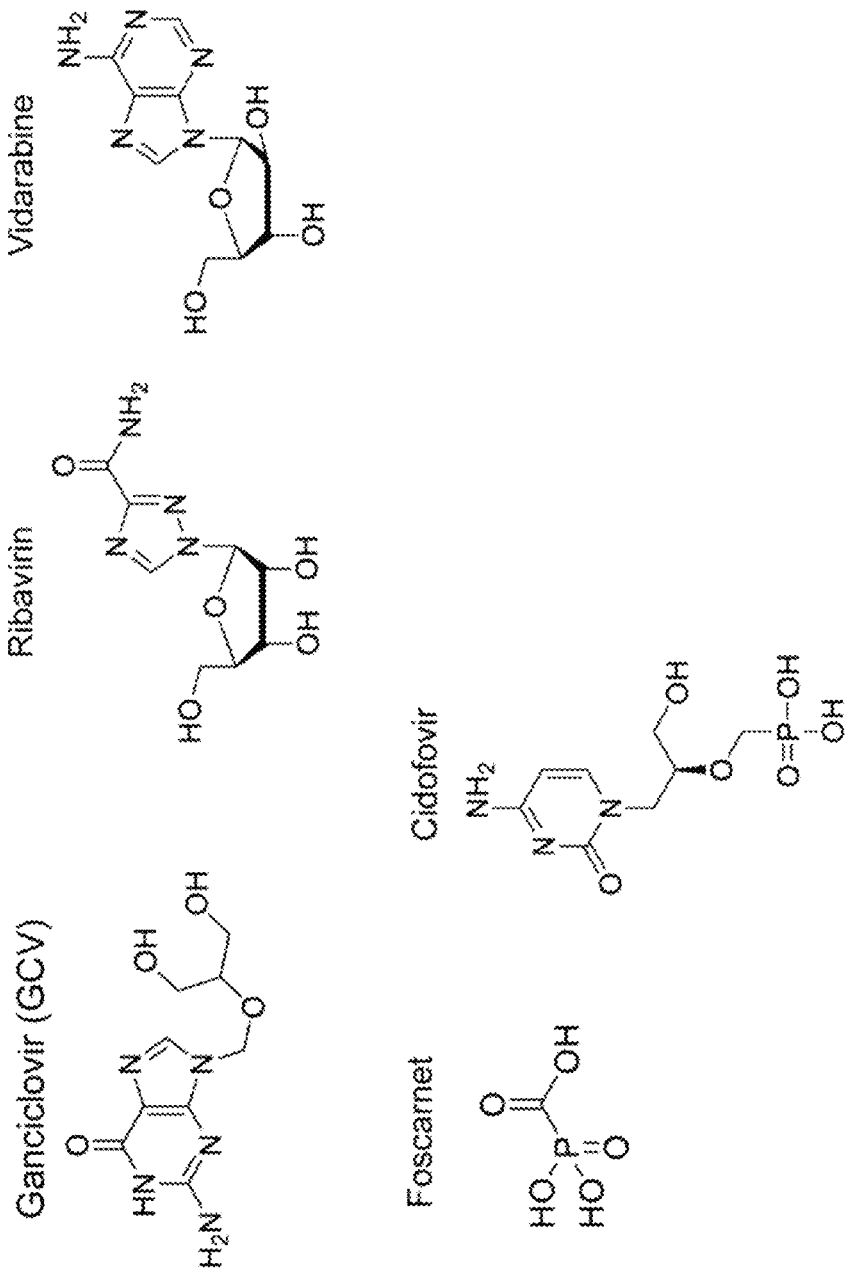
FIG. 7A shows structures of anti-viral compounds.
Figure 7B:
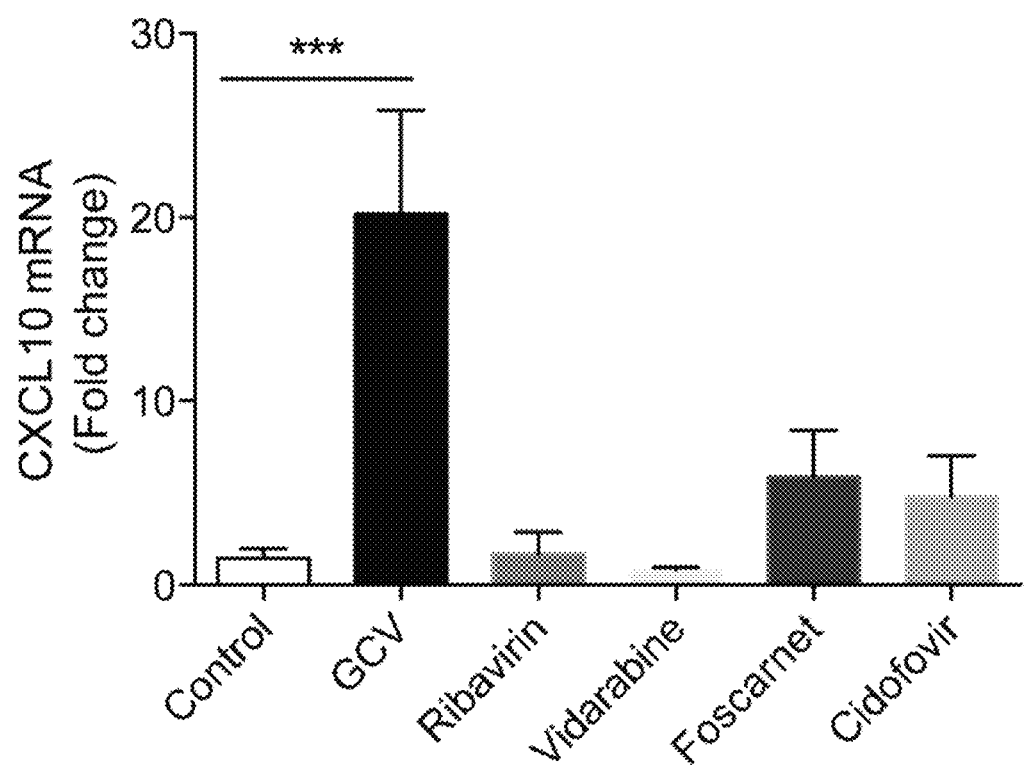
FIG. 7B shows screening for anti-viral compounds (200 µM), which included testing for increases in the CXCL10 transcript by RT-PCR in BV-2 cells treated with the indicated drugs for 24 hours. Statistical test: one-way ANOVA followed by Dunnett's multiple comparison test.

Structurally related, FDA approved GCV analogs, Acyclovir and Penciclovir or endogenous molecules, guanine and guanosine failed to induce CXCL10 mRNA (FIGS. 2A, 6), suggesting the 1,3-dihydroxy-2-propoxymethyl group at N9 of guanine is necessary for activity. In support of this notion, methylating the 1, 3 dihydroxyl groups in GCV abrogated CXCL10 inducing activity, while providing 4 hydroxyl groups in GCV dimers synthesized using reducible disulfide linker (thiol-GCV) or non-reducible PEG linkers (diGCV) at C6 of guanine increased potency to induce CXCL10 (FIGS. 2B-2C, 6). Additionally, diGCV, as well as the PEGylated GCV monomer (monoGCV, FIG. 6), potently reduced inflammatory markers (FIG. 2D) and nitric oxide production (FIG. 2E) in IFNγ/LPS stimulated microglia, and they triggered CXCL10 independent of endogenous tk1 (FIG. 2F). In contrast, the structurally unrelated anti-viral drugs Ribavirin, Vidarabine, Foscarnet, or Cidofovir failed to induce CXCL10 transcription in BV-2 cells (FIG. 7), supporting a structure-activity relationship in the observed effects.

Figure 3A:
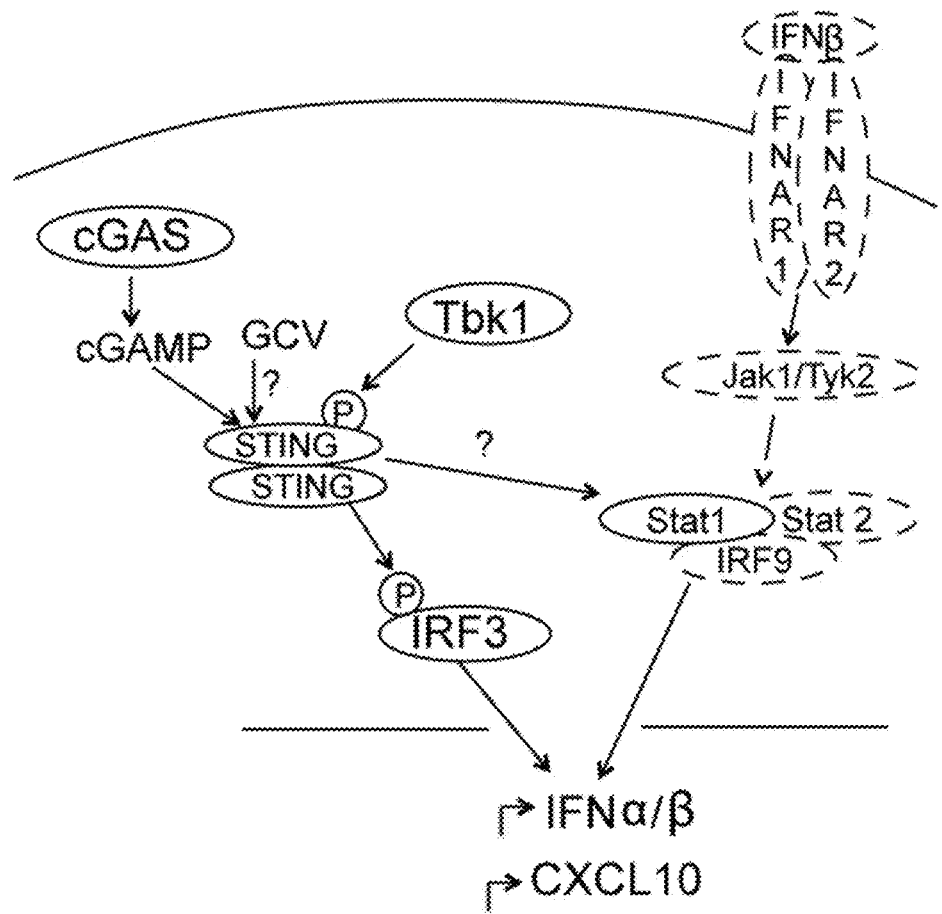
FIGS. 3A-3I show that the STING pathway is required for GCV activity in microglia.
Figure 3B:
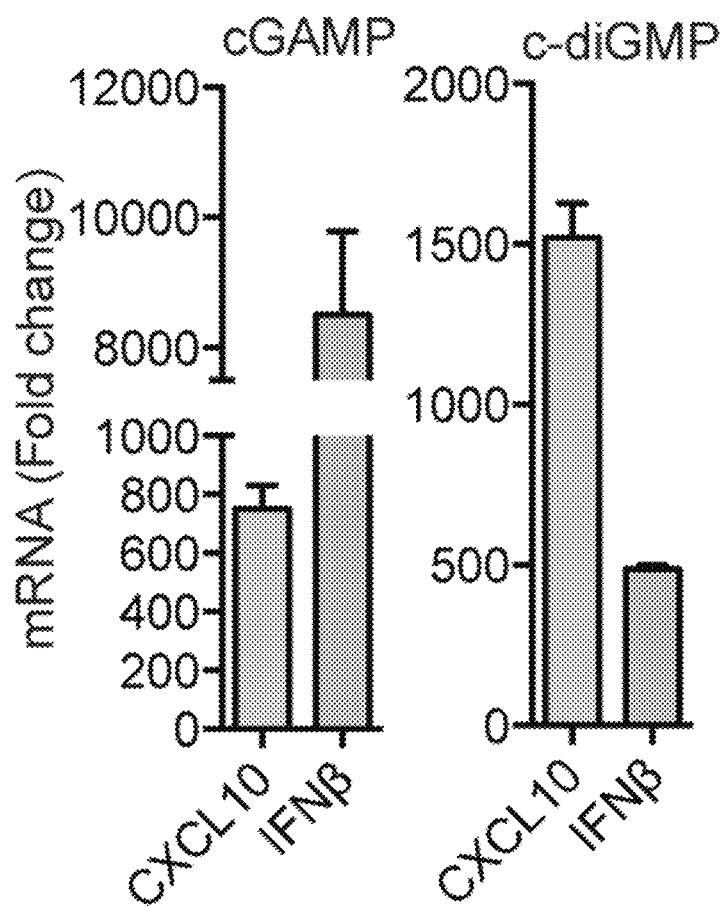
Figure 3C:
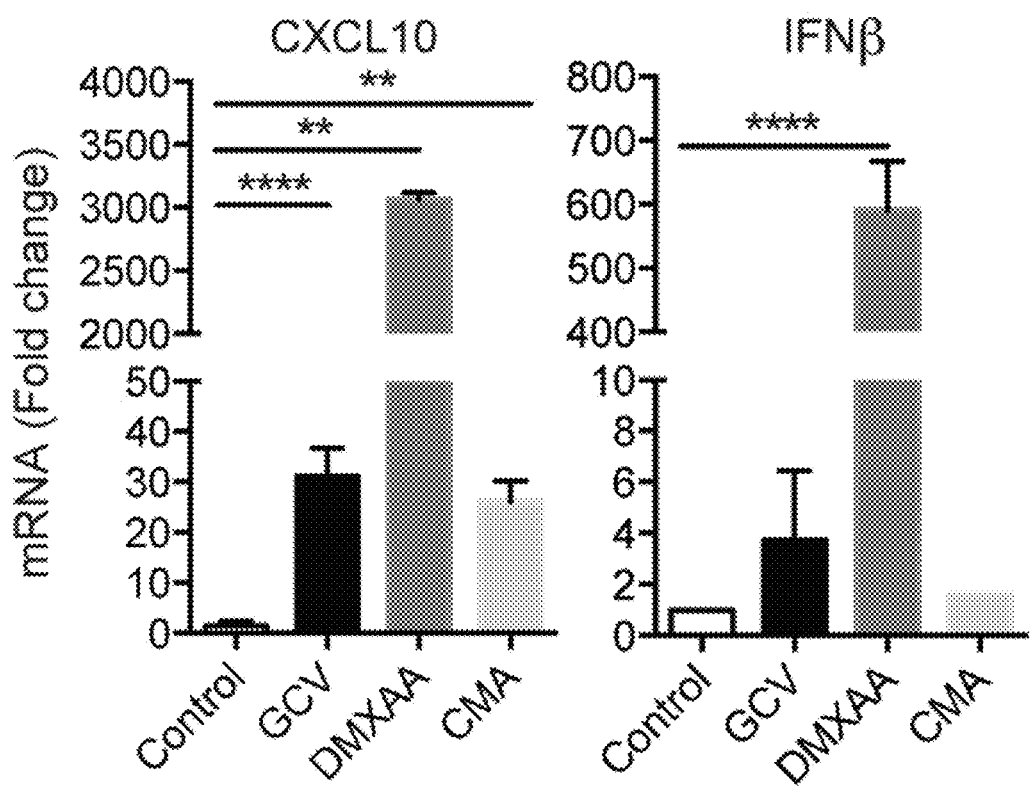
Figure 3D:
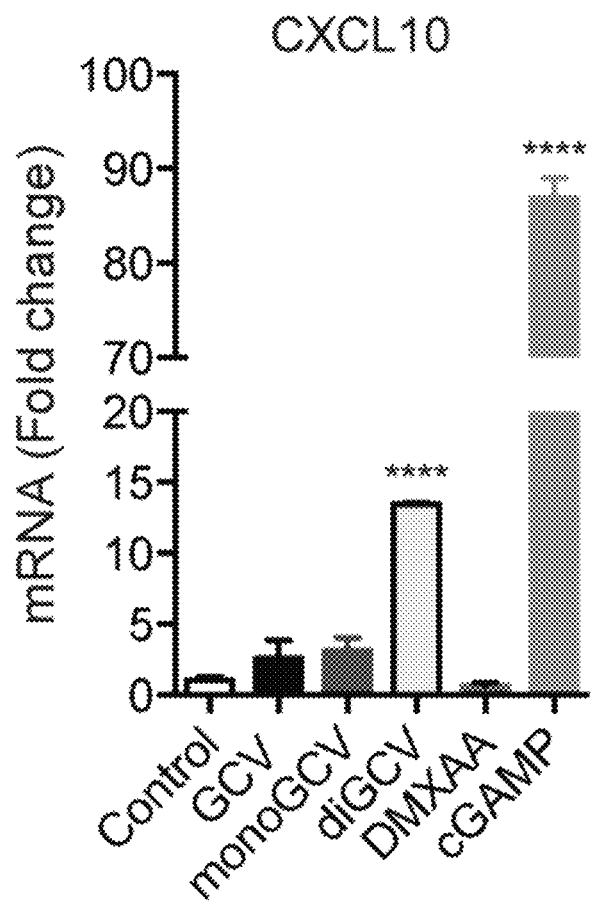

Recent studies have shown that upon sensing viral DNA in the host cytoplasm, the enzyme cyclic GMP-AMP synthetase (cGAS) catalyzes formation of cyclic-GAMP (cGAMP, FIG. 6), which subsequently induces a potent interferon response (Hornung et al. (2014) Nat Rev Immunol 14:521-528; Ishikawa et al. (2009) Nature 461:788-792). Bacterial cyclic dinucleoside monophosphates (e.g. c-diGMP, FIG. 6) can induce a similar response (Chin et al. (2013) Acta Crystallogr D Biol Crystallogr 69:352-366). These dinucleotides activate the ER membrane adapter protein STING through TANK binding kinase 1 (Tbk1), leading to the activation of IRF3 (Barber et al. (2011) Nat Immunol 12:929-930); Ishikawa et al. (2008) Nature 455:674-678) and downstream effector genes including IFNβ and CXCL10 (FIG. 3A). Accordingly, and in line with previous studies (Gao et al. (2013) Cell 154:748-762), cGAMP and c-diGMP strongly induced CXCL10 and IFNβ in microglia (FIG. 3B), as did the reported STING agonists, DMXAA and CMA (Gao et al., supra; Prantner et al. (2012) J Biol Chem 287:39776-39788; Cavlar et al. (2013) Embo J 32:1440-1450) (FIG. 3C). GCV also induced CXCL10 mRNA in a human monocyte cell line, while DMXAA, which is specific for mouse STING (J. Conlon et al. (2013) J Immunol 190:5216-5225), did not (FIG. 3D).

Figure 3E:
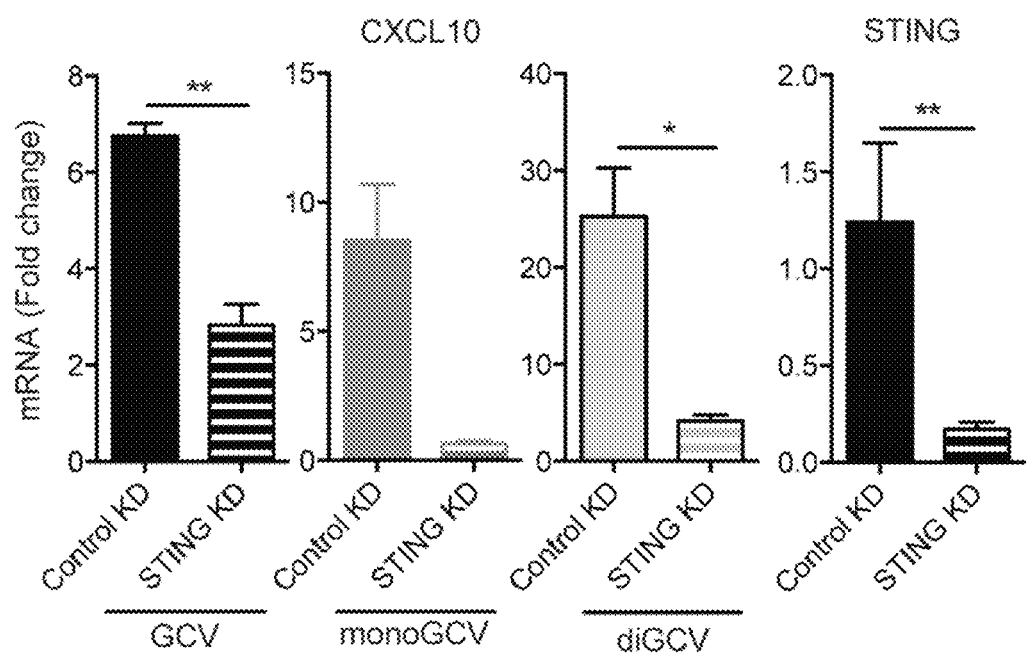
Figure 3F:
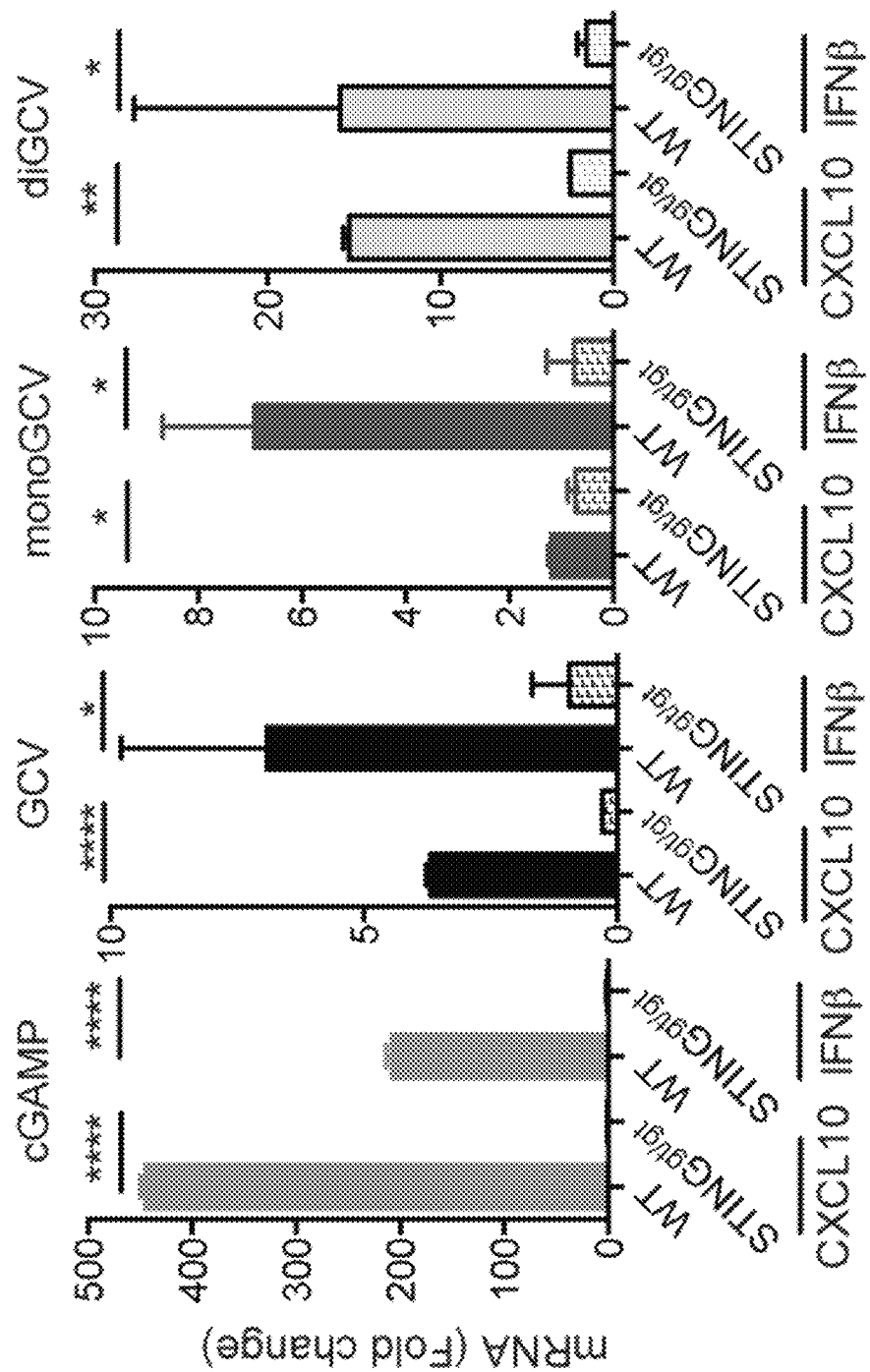
Figure 3G:
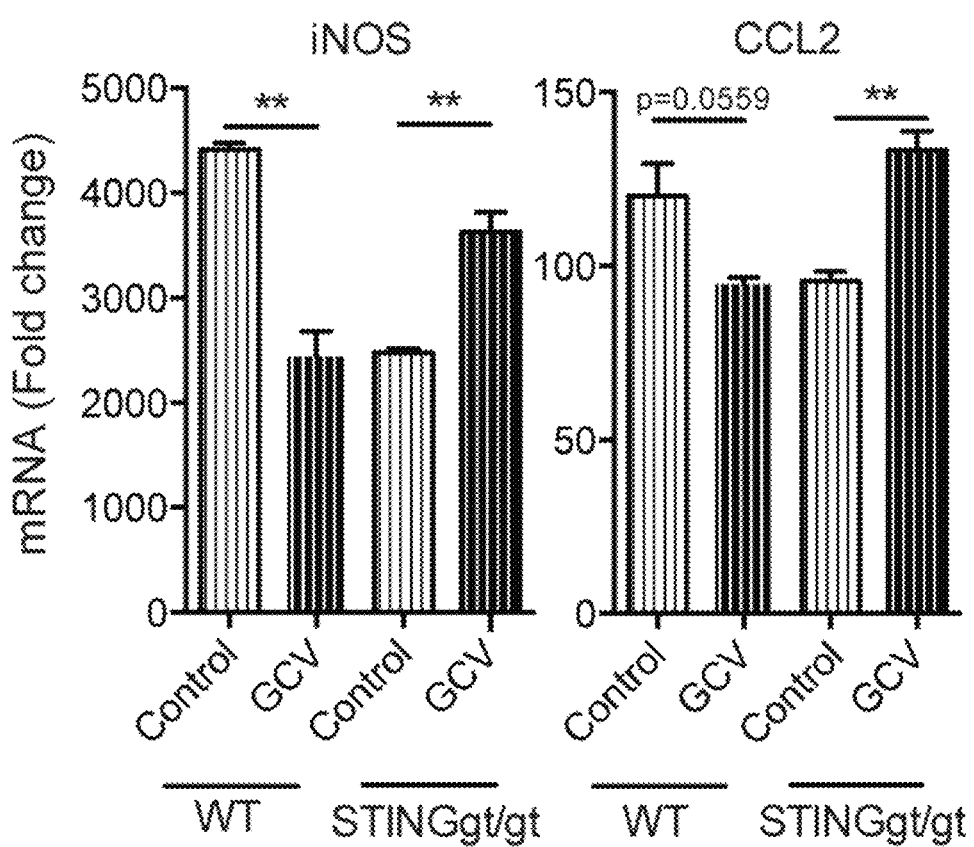
Figure 3H:
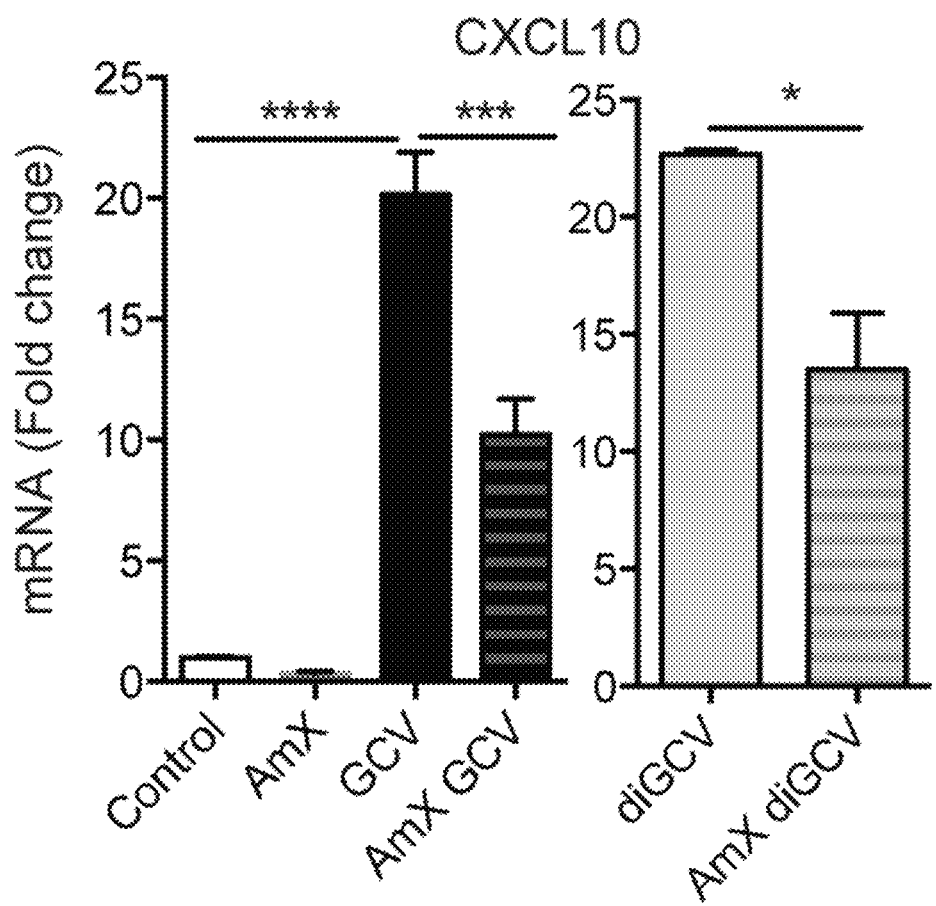
Figure 3I:
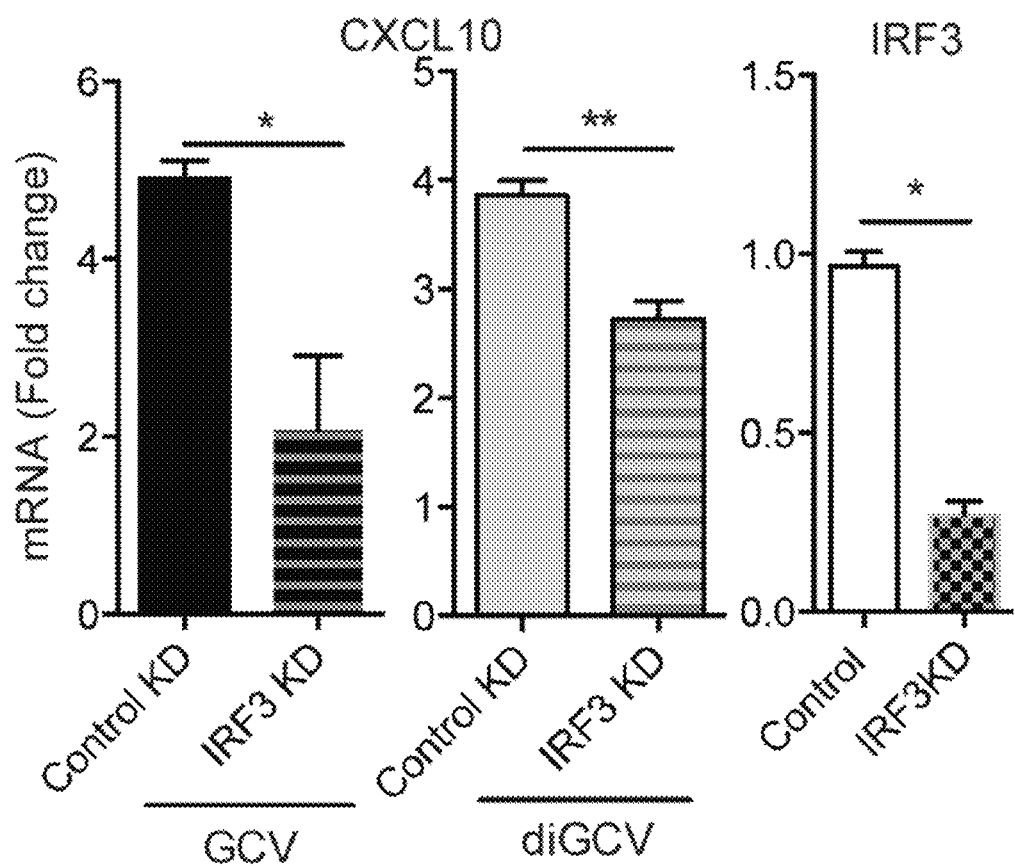

Due to its apparent structural similarity (FIG. 6), we hypothesized that diGCV, and possibly GCV cellular metabolites, may mimic cyclic dinucleotides and activate the STING pathway. Excitingly, siRNA mediated knock down of STING in BV-2 microglia largely abrogated the capacity of diGCV and, to a lesser extent, monomeric GCV to induce CXCL10 (FIG. 3E). Moreover, primary microglia from STING$^{gt/gt}$ mice that lack functional STING protein (Sauer et al. (2011) Infect Immun 79:688-694) and do not respond to cGAMP, failed to induce CXCL10 and IFNβ mRNA in response to GCV, monoGCV, and diGCV (FIG. 3F). GCV also reduced inflammatory markers in IFNγ/LPS-stimulated wildtype primary microglia, but it was unable to do so in primary microglia from STING$^{gt/gt}$ mice (FIG. 3G). Interestingly, iNOS and CCL2 transcripts were higher in GCV treated STING$^{gt/gt}$ microglia, possibly due to inherent differences in basal immune activation in STING$^{gt/gt}$ mice which are unable to induce a type I interferon response. Consistent with GCV targeting the STING pathway, pharmacological inhibition of Tbk1 activity using the antagonist Amlexanox and siRNA-mediated knockdown of IRF3 inhibited the potential of monomeric and dimeric GCV to induce CXCL10 mRNA (FIGS. 3H-3I).

Figure 8A:
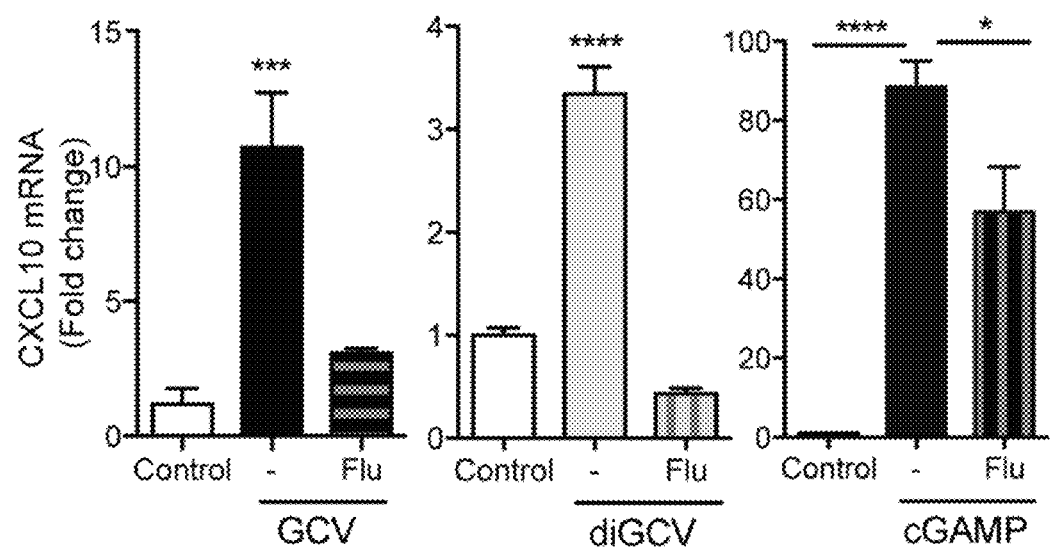
FIGS. 8A-8D show that Stat1 is required for GCV activity in microglia.
Figure 8B:
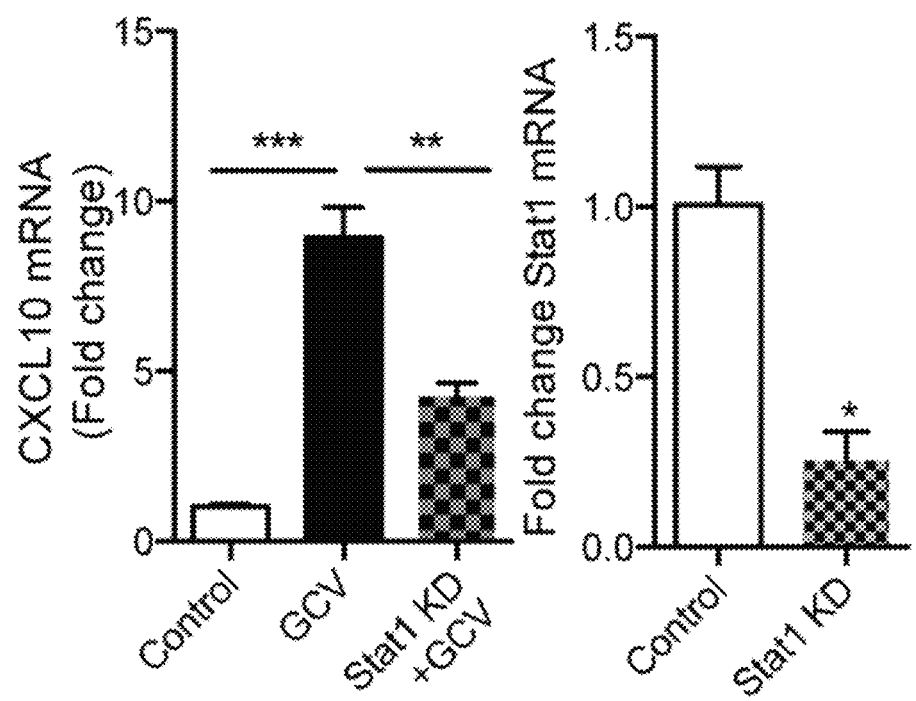
Figure 8C:
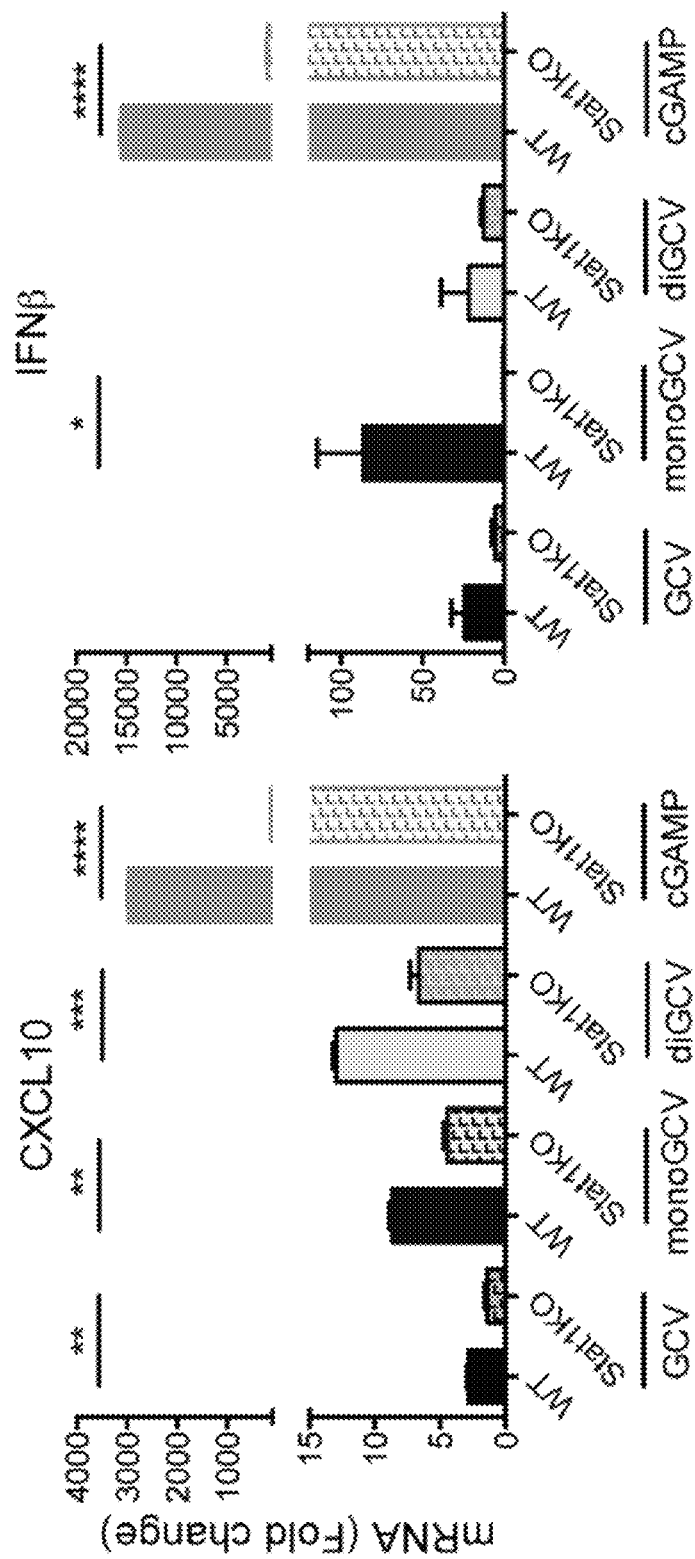
Figure 8D:
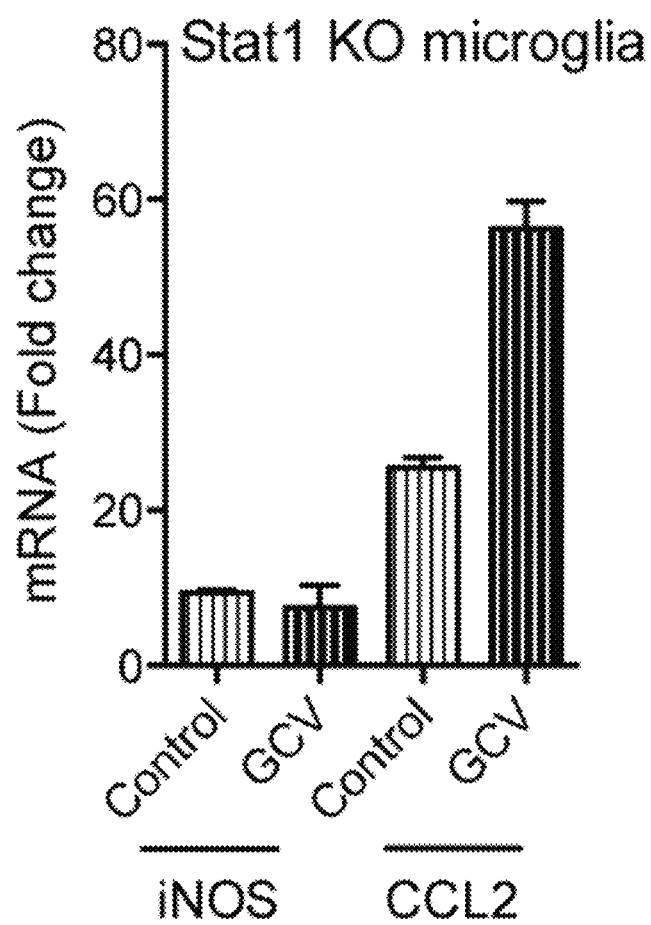
Figure 9A:
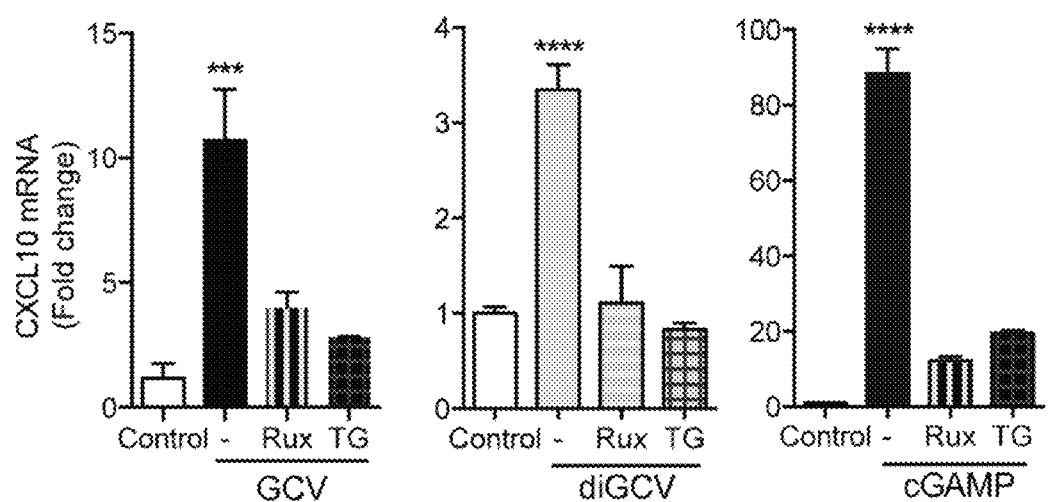
FIGS. 9A and 9B show that Jak kinases are required for CXCL10 production by GCV and its derivatives.
Figure 9B:
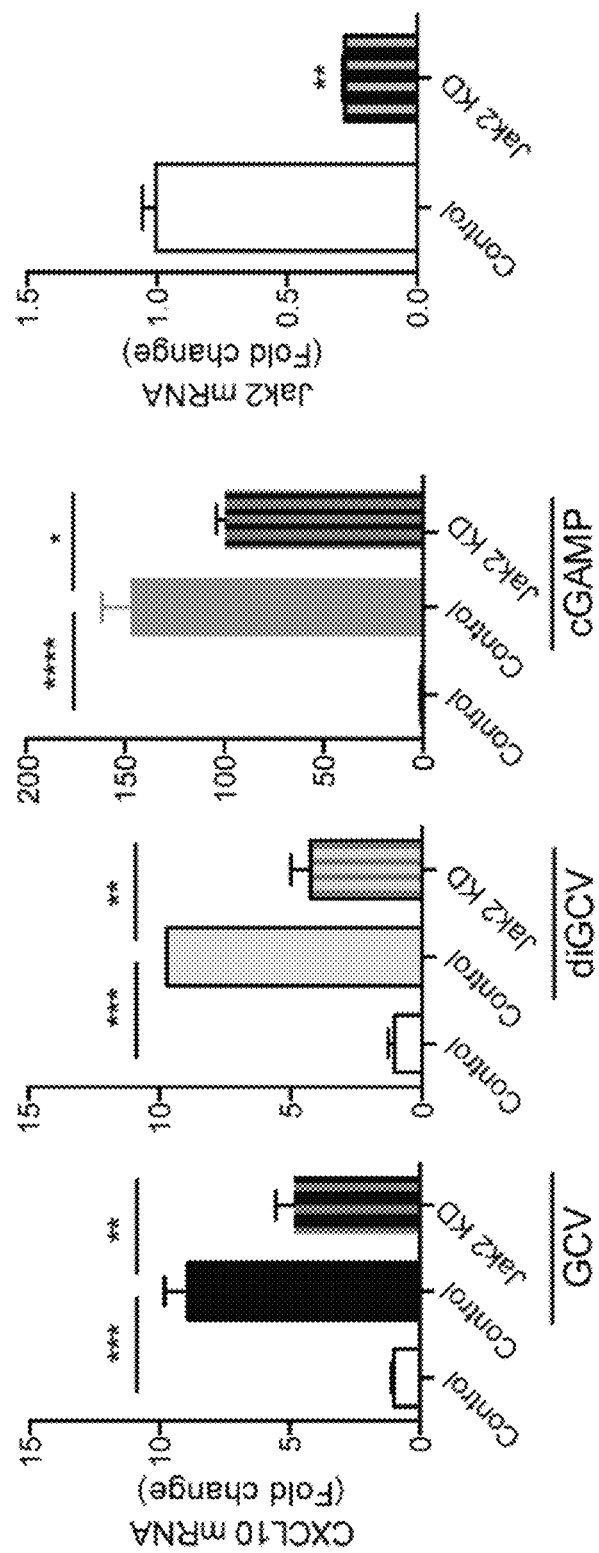
Figure 10:
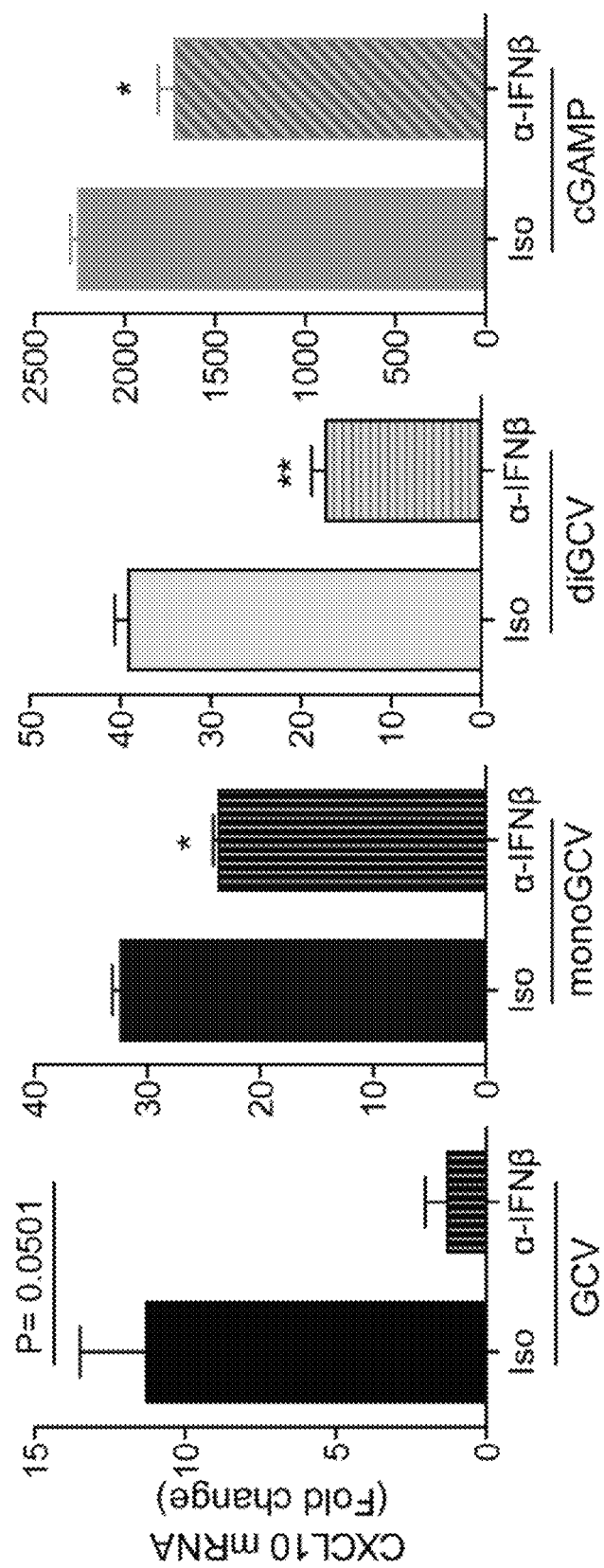
FIG. 10 shows that IFNβ secretion is important for CXCL10 production. BV-2 microglia were treated with 200 µM GCV, monoGCV, diGCV or cGAMP along with anti-IFNβ antibody (α-IFNβ) or isotype (Iso) control for 4 hours and CXCL10 transcript analyzed by RT-PCR. Statistical analysis by Student's unpaired t-test.

Interferons activate the Jak/Stat signaling pathway to induce CXCL10 (Liu et al. (2011) Oncol Lett 2:583-589), and we observed that GCV and diGCV similarly depend on it (FIGS. 8, 9). Specifically, the Stat1 inhibitor Fludarabine (Frank et al. (1999) Nat Med 5:444-447) or the Jak kinase inhibitors Ruxolitinib and TG101348 (Zhou et al. (2014) Leukemia 28:404-407) strongly inhibited CXCL10 production in BV-2 cells in response to GCV and diGCV, and somewhat less pronounced with cGAMP (FIGS. 8A and 9A). Likewise, siRNA knockdown of Stat1 and Jak2 in BV-2 cells (FIGS. 8B and 9B) or lack of Stat1 in primary microglia (FIG. 8C) also significantly reduced CXCL10 or IFNβ mRNA expression by GCV, monoGCV, diGCV and cGAMP. These compounds could activate the Jak/Stat1 pathway either directly or through the production and autocrine signaling of IFNβ. Indeed, neutralization of IFNβ with an antibody partly reduced induction of CXCL10 mRNA by GCV, monoGCV, diGCV or cGAMP in BV-2 cells (FIG. 10). These data, in aggregate, show that, like the reported STING agonists (Gao et al., supra; Cavlar et al., supra; Burdette et al. (2011) Nature 478:515-518), the ability of GCV and its derivatives to induce a type I interferon response in microglia requires a functional STING pathway and involves Jak/Stat signaling.

Figure 4A:
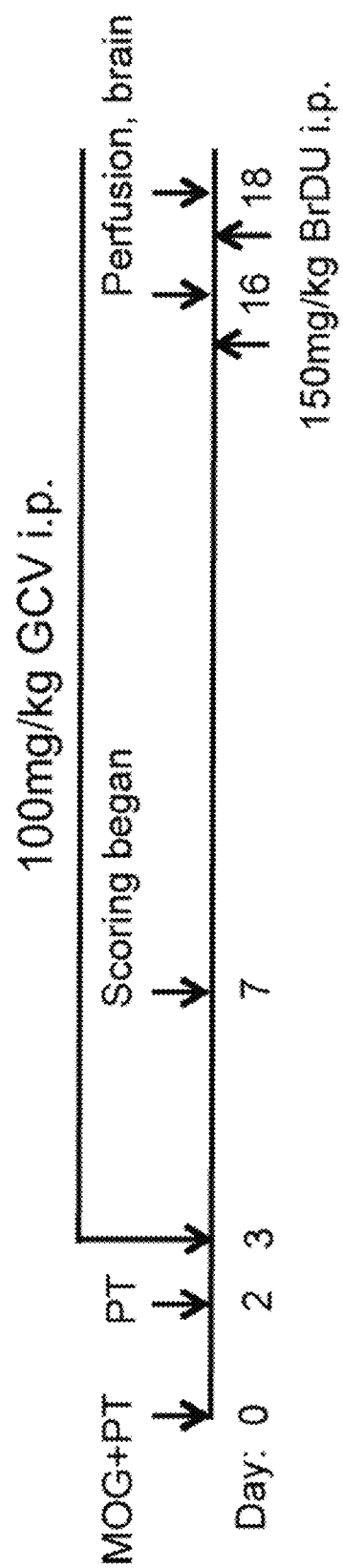
FIGS. 4A-4J show that STING is required for complete inhibition of inflammation in EAE by GCV.
Figure 4B:
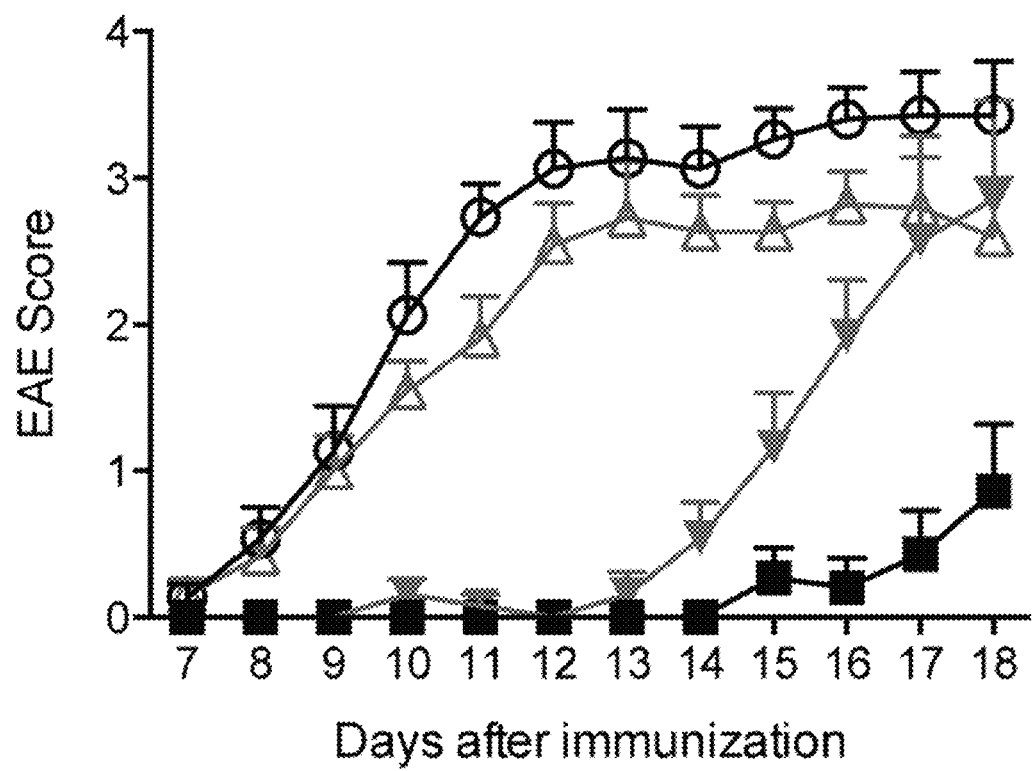
Figure 4C:
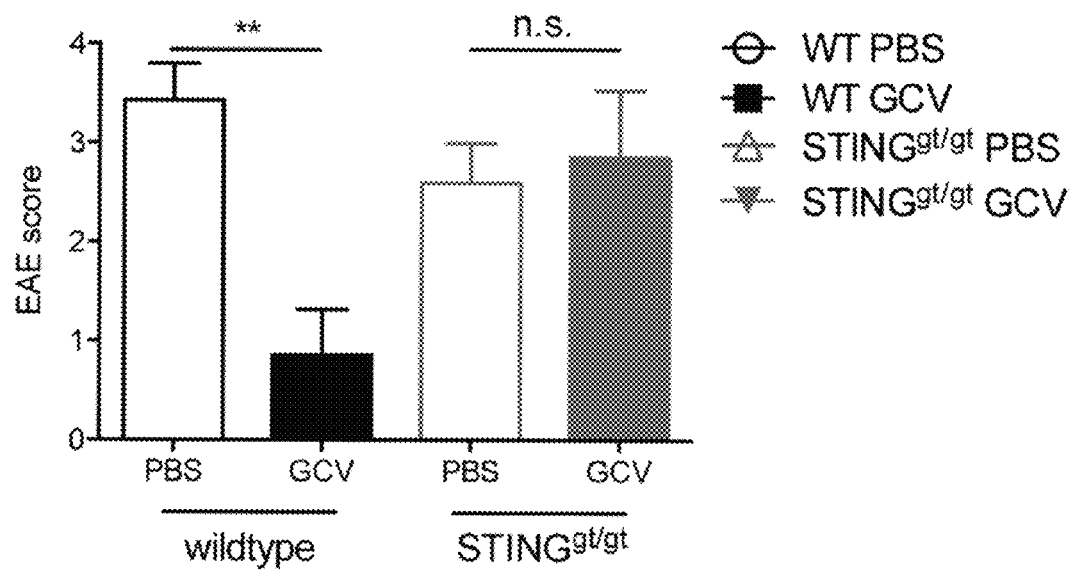
Figure 4D:
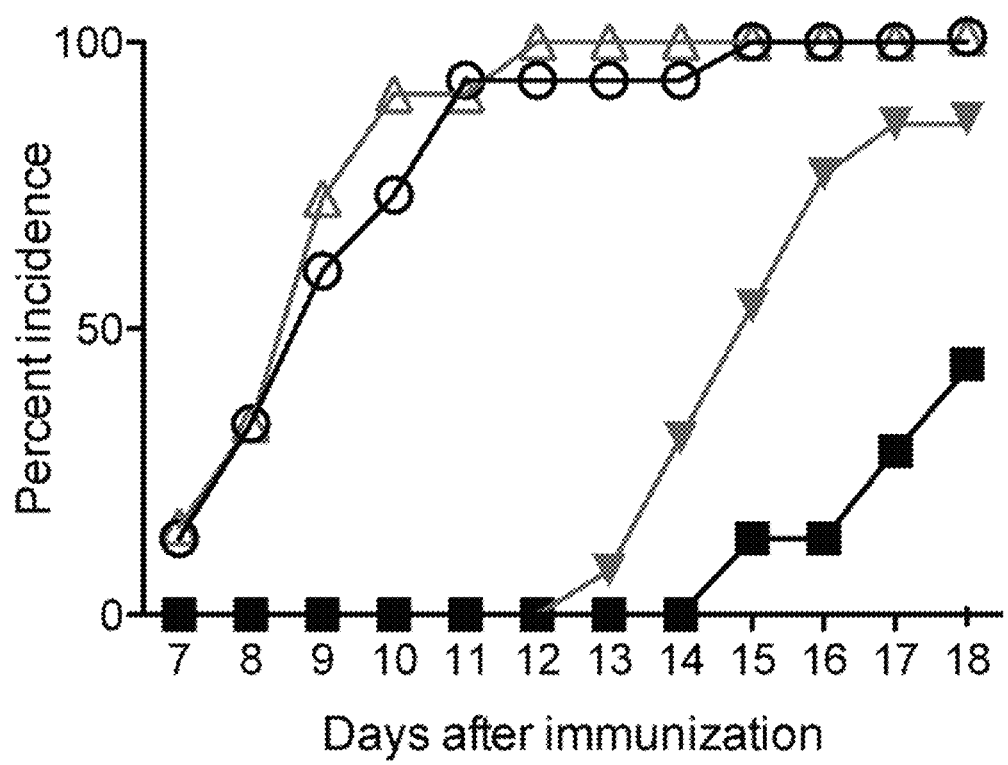
Figure 4E:
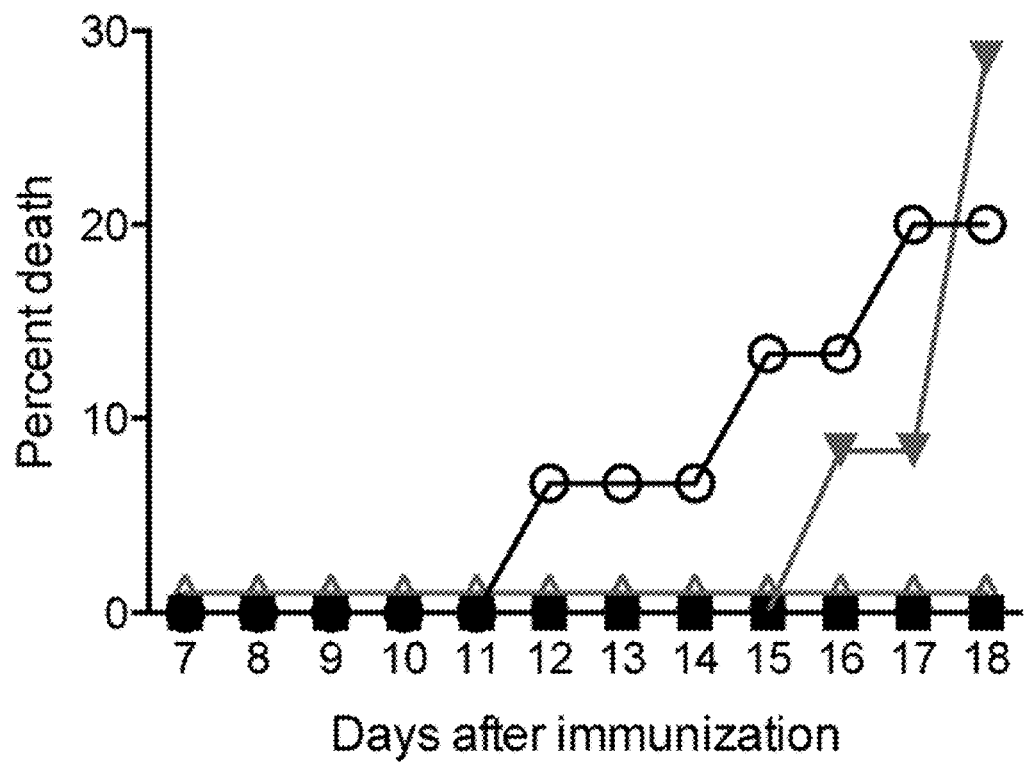
Figure 4F:
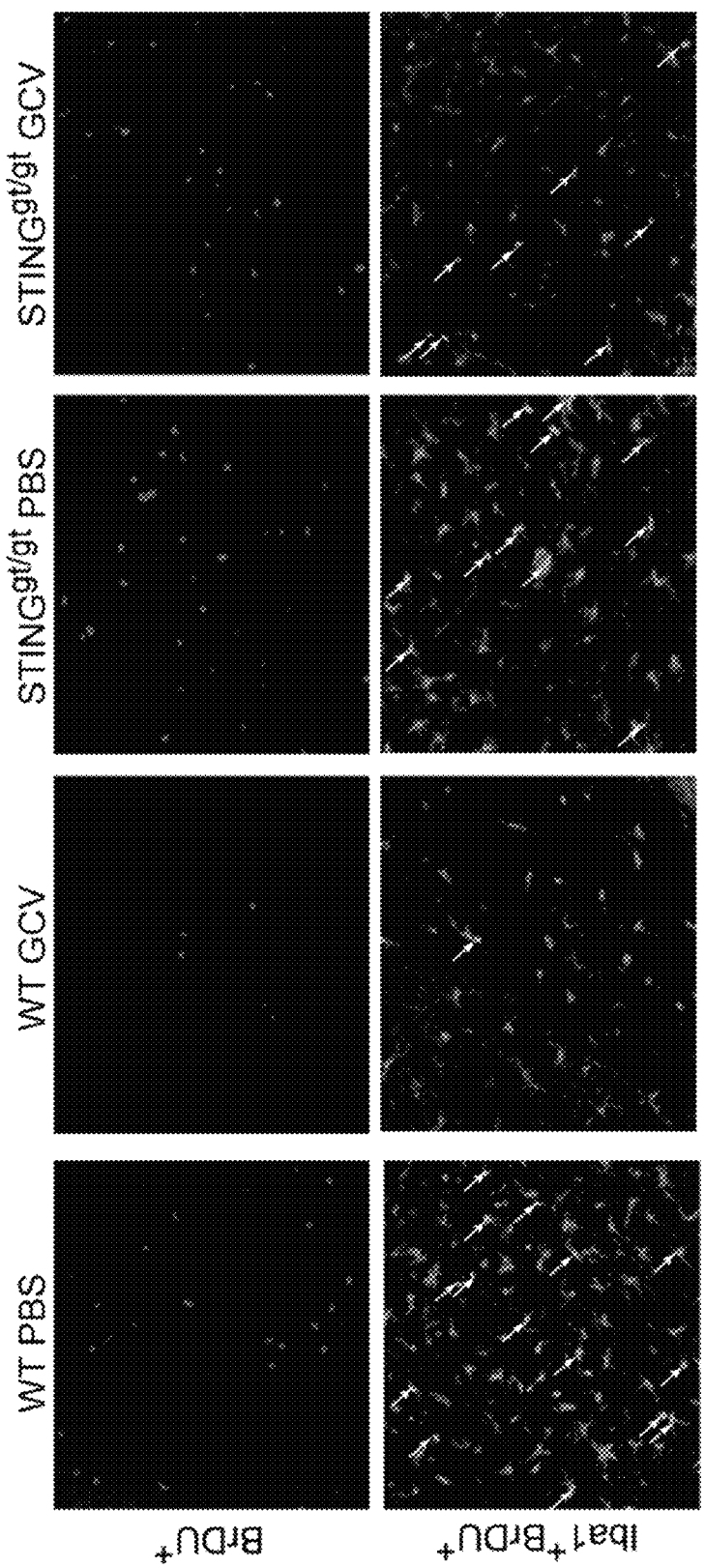
Figure 4G:
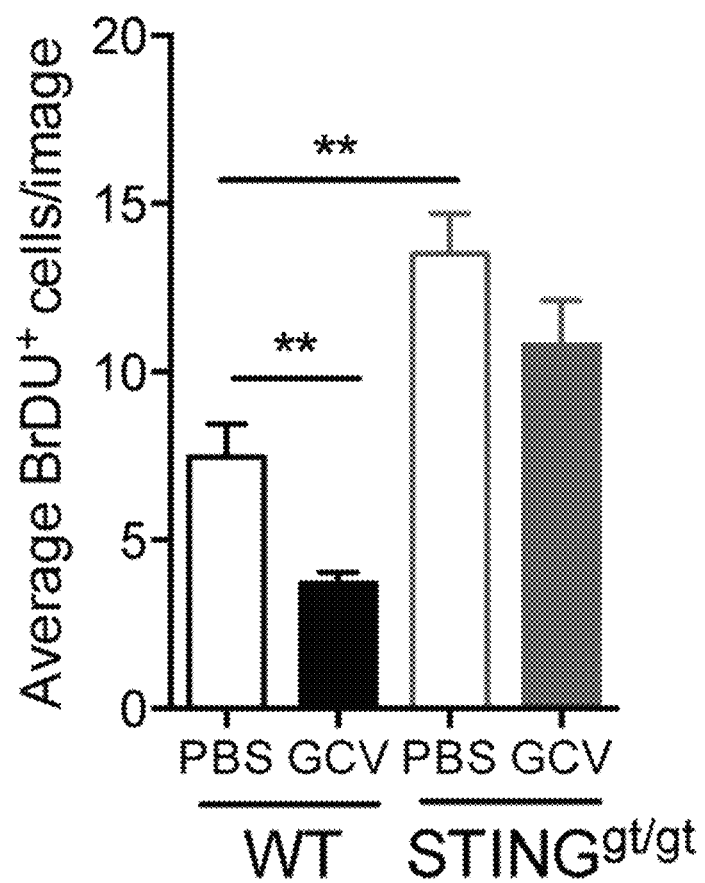
Figure 4H:
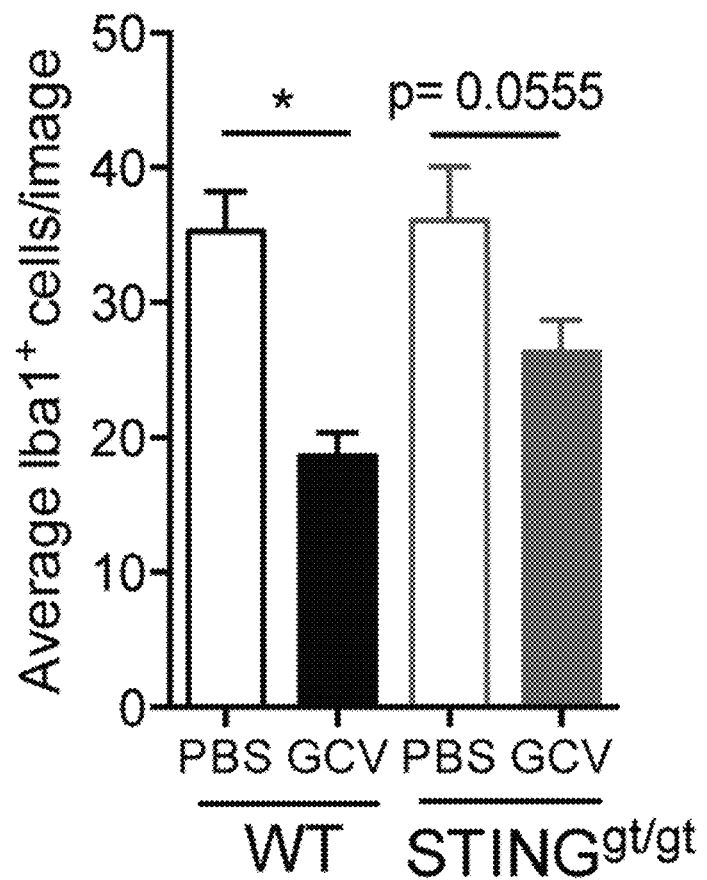
Figure 4I:
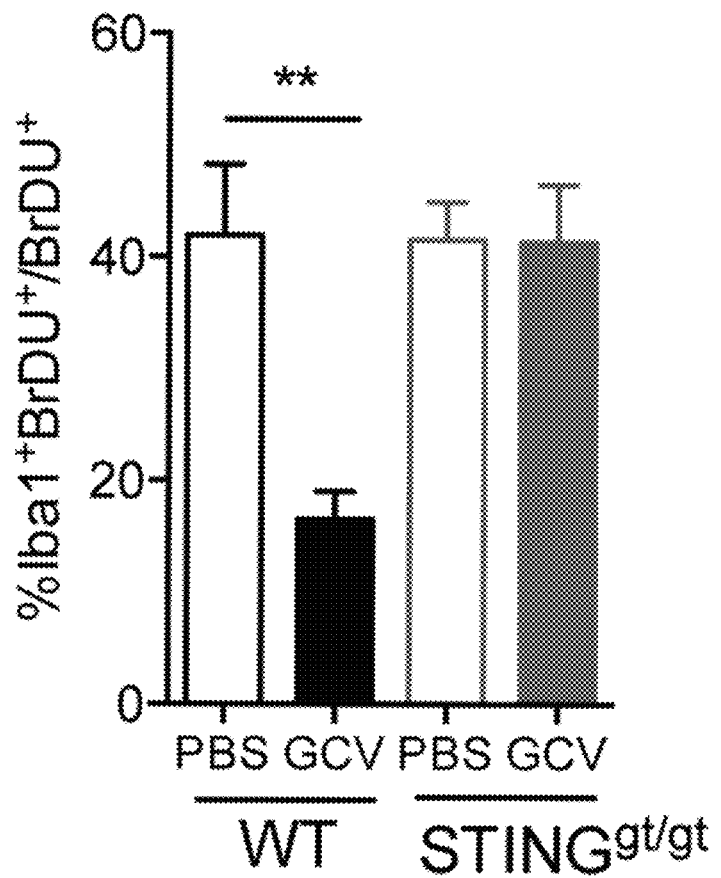
Figure 4J:
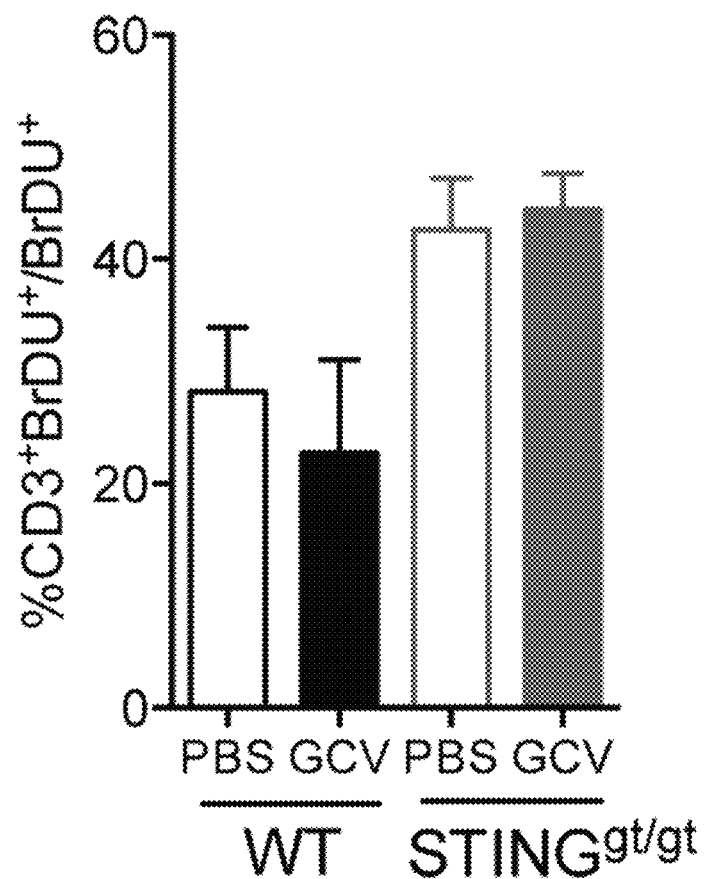

To determine if STING is required for the therapeutic and anti-inflammatory effects of GCV in vivo we induced the autoimmune disease EAE in wildtype and STING$^{gt/gt}$ mice and treated them with GCV (FIG. 4A). As we previously reported (Ding et al., supra), GCV drastically reduces disease severity in wildtype mice (FIGS. 4B, 4C), lowering disease incidence from 100% to 40% (FIG. 4D) and lethality from 20% to 0% (FIG. 4E) at 18 days following disease induction. Whereas mice lacking STING showed a very similar disease course to wildtype mice (FIGS. 4B-4E), GCV only partially ameliorated EAE during the early phase of disease. Remarkably, disease severity and incidence in GCV treated STING$^{gt/gt}$ mice were not significantly different (FIGS. 4B-4D), and lethality was even higher (FIG. 4E), compared to untreated mice at 18 days following disease induction. At this time point, and again consistent with our published data (Ding et al., supra), GCV significantly decreased numbers of BrDU$^+$ proliferating cells (FIGS. 4F, 4G), Iba1$^+$ microglia (FIG. 4H), and Iba1$^+$BrDU$^+$ proliferating microglia (FIGS. 4F, 4I), but did not change CD3$^+$ BrDU$^+$ proliferating T-cells (FIG. 4J) in cerebella of wildtype mice with EAE. In stark contrast, and in agreement with the clinical data above, STING$^{gt/gt}$ mice with EAE showed no reduction in overall cell proliferation (FIGS. 4F, 4G), proliferating microglia (FIGS. 4F, 4I) or T-cells (FIG. 4J) following treatment with GCV. Interestingly, STING$^{gt/gt}$ mice with EAE had twice as many proliferating cells as wildtype mice (FIG. 4G), and GCV showed a trend towards reducing overall Iba1 immunoreactivity (FIG. 4H), suggesting a role for STING in multiple aspects of EAE. In support of our finding, activation of STING by cyclic dinucleotides attenuated EAE in a recently published study (Lemos et al. (2014) J Immunol 192:5571-5578). In summary, GCV therapeutic activity in EAE depends partially on the presence of STING supporting the molecular studies that GCV is an activator of the STING pathway.

Ganciclovir is a widely used antiviral drug and a close analog of Acyclovir, the first successful antiviral drug, described in 1977 to exploit viral thymidine kinase activity and inhibiting viral replication (Elion et al. (1977) Proc Natl Acad Sci USA 74:5716-5720). Our study uncovered a remarkable novel, non-canonical activity of GCV, but not Acyclovir, which involves activation of the innate immune receptor STING and a stereotypical cellular antiviral program. To our knowledge, this dual modality of GCV is unique and may, in part, be responsible for the continued strong success of GCV (and its pro-drug Valganciclovir), in spite of many newer antiviral drugs. Because of its growing relevance not only in anti-viral immune responses but possibly in sensing mitochondrial damage as well (West et al. (2015) Nature 520:553-557), STING has become an attractive target for drug development itself (He et al. (2015) Trends Pharmacol Sci 36:51-64). In addition, mutations in STING are associated with vascular and pulmonary syndrome (Liu et al. (2014) N Engl J Med 371:507-518) and other autoimmune diseases (Sharma et al. (2015) Proc Natl Acad Sci USA 112:E710-717; Jeremiah et al. (2014) J Clin Invest 124:5516-5520), STING-IRF3 stress is associated with alcohol liver disease (Petrasek et al. (2013) Proc Natl Acad Sci USA 110: 16544-16549), and haploinsufficiency in the STING activating kinase Tbk1 is associated with ALS and FTD (Freischmidt et al. (2015) Nat Neurosci 18: 631-636; Pottier et al. (2015) Acta Neuropathol 130:77-92). Our findings that GCV, and GCV dimers in particular, activate the STING pathway and reduce microglial proliferation and neuroinflammation in vivo open the possibility to develop a new class of drugs to treat neurodegenerative and related diseases where neuroinflammation has been implicated.

Materials and Methods

Cell Culture

BV-2 mouse microglia cells were grown in DMEM+10% FBS and THP-1 human monocyte cells were grown in RPMI-40+10% FBS+0.05 mM β-mercaptoethanol at 37° C., 5% $CO_2$. Adherent cells were split using 1×TrypLE (Gibco). For cellular assays, cells were treated with the following concentrations of drugs as indicated in the DMEM without serum: 100-200 μM ganciclovir, 10 ng/ml IFNγ (R&D systems), 100 ng/ml LPS (Sigma-Aldrich), 1-10 μM Fludarabine (Selleckchem), 1 μM Ruxolitinib (Selleckchem), 1 μM TG-101348 (Selleckchem), 1 μM Amlexanox (Tocris bioscience) unless otherwise noted. All experiments were run in triplicates and replicated at least 3 times with cell lines and at least twice with primary microglia. Average data are shown for cell lines and representative data are shown for primary cells. Secreted signaling proteins were measured in supernatants from cultured cells stimulated with GCV and conditioned for 24 hours in the absence of serum using two independent Luminex arrays (Human Immune Monitoring Center, Stanford and Eve technologies, Canada). Nitrite assay was performed on conditioned culture supernatants of cells stimulated with drugs for 24 hours using the Griess Reagent System (Promega) according to manufacturer's instructions. To assess cellular viability, cell confluence was measured using an automated microscope (Cellavista; Roche).

Primary Microglia Culture

Mice were housed and bred according to the Institutional Animal Care and Use Committee guidelines. Primary microglia and astrocytes were isolated from P0-P3 C57BL/6 mouse pups. Cortices from pups were isolated, meninges removed and tissue was dissociated using a 25-gauge needle. Two cortices were plated on each poly-L-lysine coated T-75 flasks in DMEM/F12+10% FBS+1% penicillin/streptomycin. Microglia and astrocyte co-cultures were maintained for 3 weeks, after which microglia were isolated using CD11b magnetic beads (Miltenyi Biotec) according to the manufacturer's instructions. Isolated microglia were allowed to recover for 1-2 days and processed for cellular assays described above.

For tk KO experiments only, microglia were isolated from adult mouse brains using the neural dissociation kit (Miltenyi Biotec) according to manufacturer's protocol followed by CD11b magnetic bead enrichment. Isolated cells were cultured for 3-4 days before the experiment.

siRNA Knockdown

Smartpool siRNAs against mouse targets were bought from Dharmacon and transfected in microglia cells using Viromer Blue from Lipocalyx at a concentration of 50 nM according to manufacturer's instructions. Drugs were added cells after 24 hours of transfection and assays done 24 hours after addition of drugs.

RNA Preparation and Real-Time PCR (RT-PCR)

RNA was isolated from cells using RNeasy mini kit from Qiagen. DNased RNA was converted to cDNA using SuperScript III reverse transcriptase kit (Life technologies). The cDNA was used to quantify specific targets using SYBR green in Roche Lightcycler 480. ΔΔCt values normalized against the experimental control to determine fold change in mRNA for each sample compared to untreated or vehicle treated control. β-actin or Ubc or both were used as housekeeping genes. Primer sequences were obtained from PrimerBank. Fold change is shown compared to the vehicle treated or untreated cells, unless otherwise noted.

EAE Induction and Analysis

EAE was induced in 2-3 month old C57BL/6 wild type (n=15) and STING$^{gt/gt}$ (n=14) female mice as described (Ding et al., supra). Briefly, mice were immunized subcutaneously with 200 µg mouse MOG$_{35-55}$ peptide (Stanford PAN facility) emulsified in CFA (200 µg M. tuberculosis, Difco adjuvants, BD) and injected intravenously with 100 ng pertussis toxin (List Biological Laboratories, Inc.) at 0 hours and 48 hours of immunization. Mice were weighed and scored for clinical signs of EAE daily: 0, no paralysis; 1, loss of tail tone; 2, hind limb weakness or paresis; 3, hind limb paralysis; 4, hind limb paralysis and forelimb paresis; 5, moribund or dead. GCV (100 mg/kg) or phosphate buffered saline (PBS) vehicle control were intra-peritoneally injected daily starting 3 days after immunization till the end of the experiment. BrDU (150 mg/kg) was intraperitoneally injected 1 day before sacrifice. GCV administration in adults and children ranges from a daily oral dose of up to 4 g or multiple daily intravenous doses of 5 mg/kg (Faulds et al., supra). In this study, we used GCV concentrations that are used to treat patients in clinic, adjusted with a factor of 12.3 for human to mouse dose conversion (Food and Drug Administration Center for Drug Evaluation and Research (CDER), Guidance for Industry Estimating the Maximum Safe Starting Dose in Initial Clinical Trials for Therapeutics in Adult Healthy Volunteers in Pharmacology and Toxicology, 2005), and are below the reported median inhibitory concentration.

Tissue Preparation, Histology and Imaging

Mice were anesthetized using Avertin (Tribromoethanol) and perfused by cardiac puncture. Brains were extracted and hemi-brains fixed in 4% paraformaldehyde for 48 hours, cryoprotected in 30% sucrose, then sectioned sagitally (40 µm) using a freezing microtome (Leica). The other hemi-brains were frozen in −80° C. Immunohistochemistry was done on 3-4 free-floating sections per mouse according to standard procedures (Ding et al., supra). Primary antibodies were against BrDU (1:2,000; Abcam), Iba1 (1:1,000; Wako Chemicals USA), and CD3 (1:1,000; BD). Sections were treated in 3 M HCl for 30 minutes at 37° C. for BrDU antigen retrieval. Secondary antibodies were Alexa Fluor 488, 555 and 594 (1:200, Lifetech). Z-stacks of images were taken on confocal microscope (Zeiss LSM700). Double positive cells were counted and images were analyzed using ImageJ.

Statistical Analyses

Statistical tests were done using Prism 6 software. Two groups were compared using unpaired Student's t-test. One-way ANOVA followed by Dunnett's multiple comparison test was used for drug treatment experiments with more than one drug, and all treatments were compared to controls. Two-way ANOVA was used for 2 groups and 2 treatment experiments followed by Sidak's multiple comparisons test unless otherwise noted. *P<0.05, P<0.01, *P<0.001, ****P<0.0001.

Synthesis and Characterization of Ganciclovir Derivatives

All non-protic reactions were run under an inert atmosphere (nitrogen) and all glassware was stored in an oven and/or was flame-dried prior to use under an inert atmosphere of nitrogen. All reactions were performed in an efficient fume hood. Solvents and reagents were purchased from commercial sources and were used without further purification. Flash chromatography was performed on silica gel 60, 230-400 mesh, using a forced flow of eluent at 0.3-0.5 bar pressure. Thin layer chromatography (TLC) was performed using 0.25 mm silica gel 60F plates with fluorescent indicator (Silicycle). Concentration under reduced pressure was performed by rotary evaporation at 35° C. Purified compounds were further dried under high cavuum (0.02-0.10 Torr). Yields refer to purified and spectroscopically pure compounds. $^1$H and $^{13}$C NMR spectra were recorded on a Bruker spectrometer operating at 400 MHz. Chemical shifts are reported in parts per million referenced relative to the peaks of the solvent. Spectra are reported as (ppm), (multiplicity, coupling constants (Hz), and number of protons). Deuterated solvents were used without further purification. NMR spectra were acquired at ambient temperatures (18±2° C.). ESI-LC/MS spectra were obtained using LTQ Mass spectrometer from Thermo scientific using reversed phase symmetry C18 column (3.5 µm, 4.6×17 mm).

Synthesis of Ganciclovir-Thiol Derivative

Figure 11A:
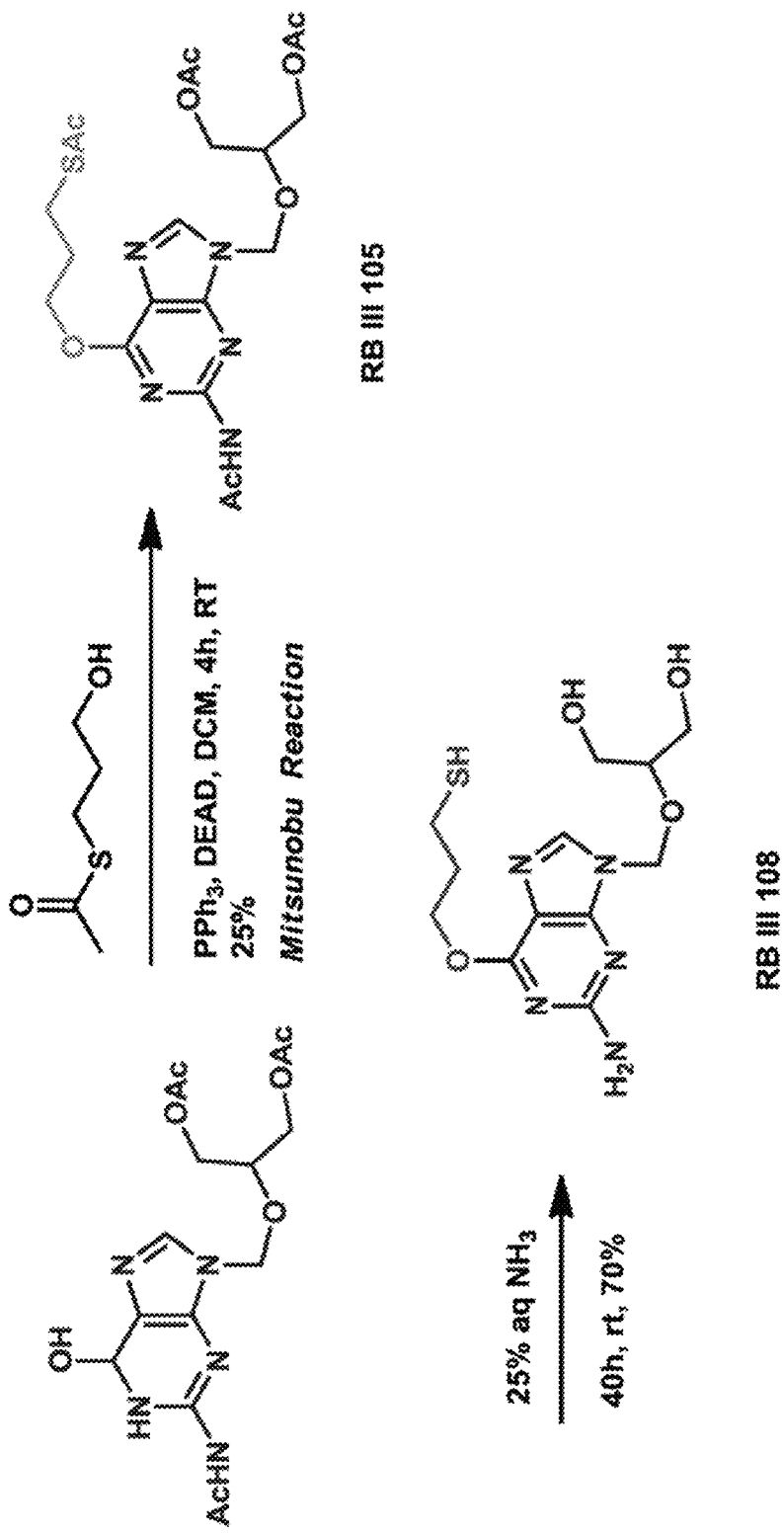
FIGS. 11A-11D show the synthesis of the GCV-thiol derivative and characterization of the reaction product.
Figure 11B:
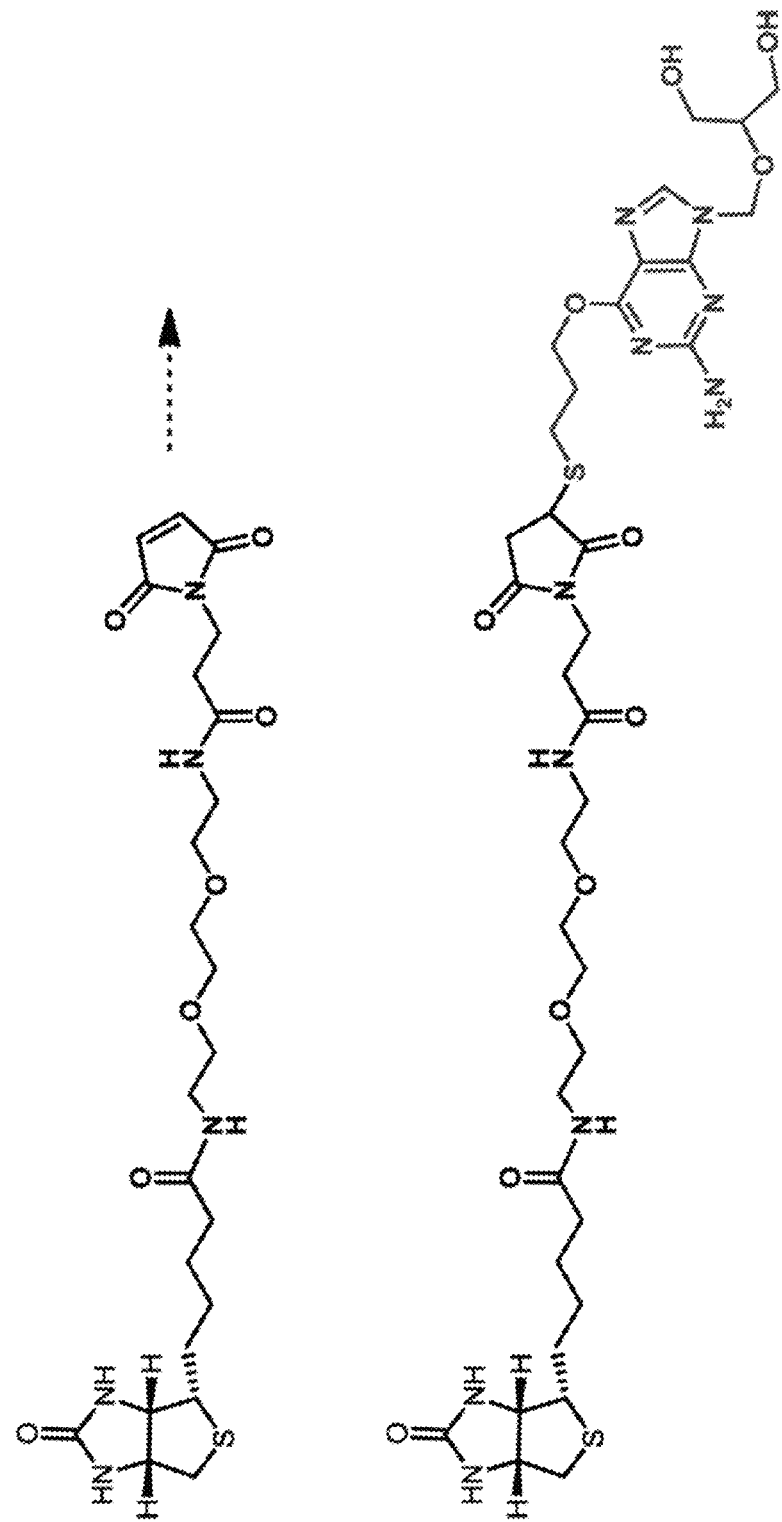
Figure 11C:
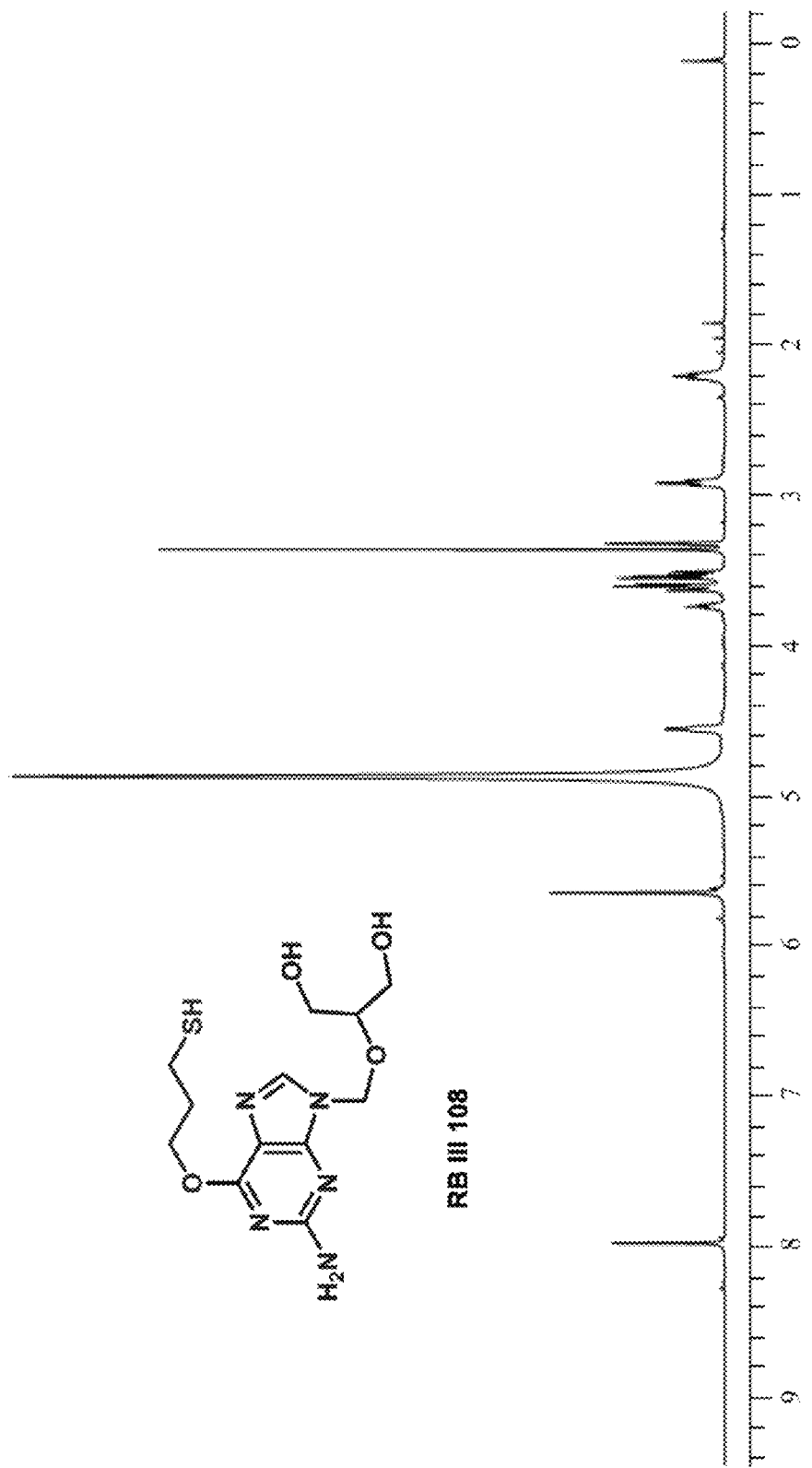
Figure 11D:
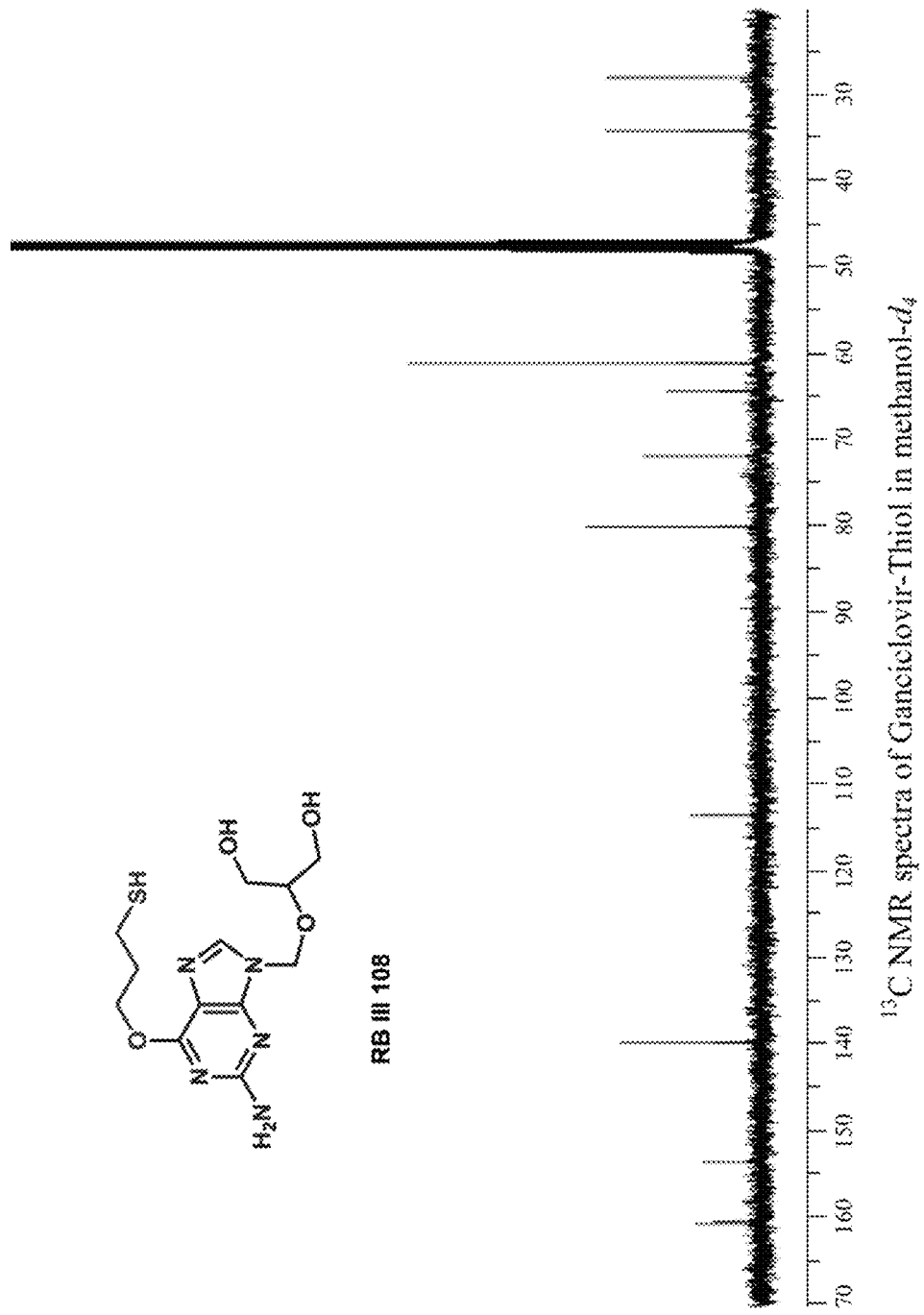
Figure 11E:
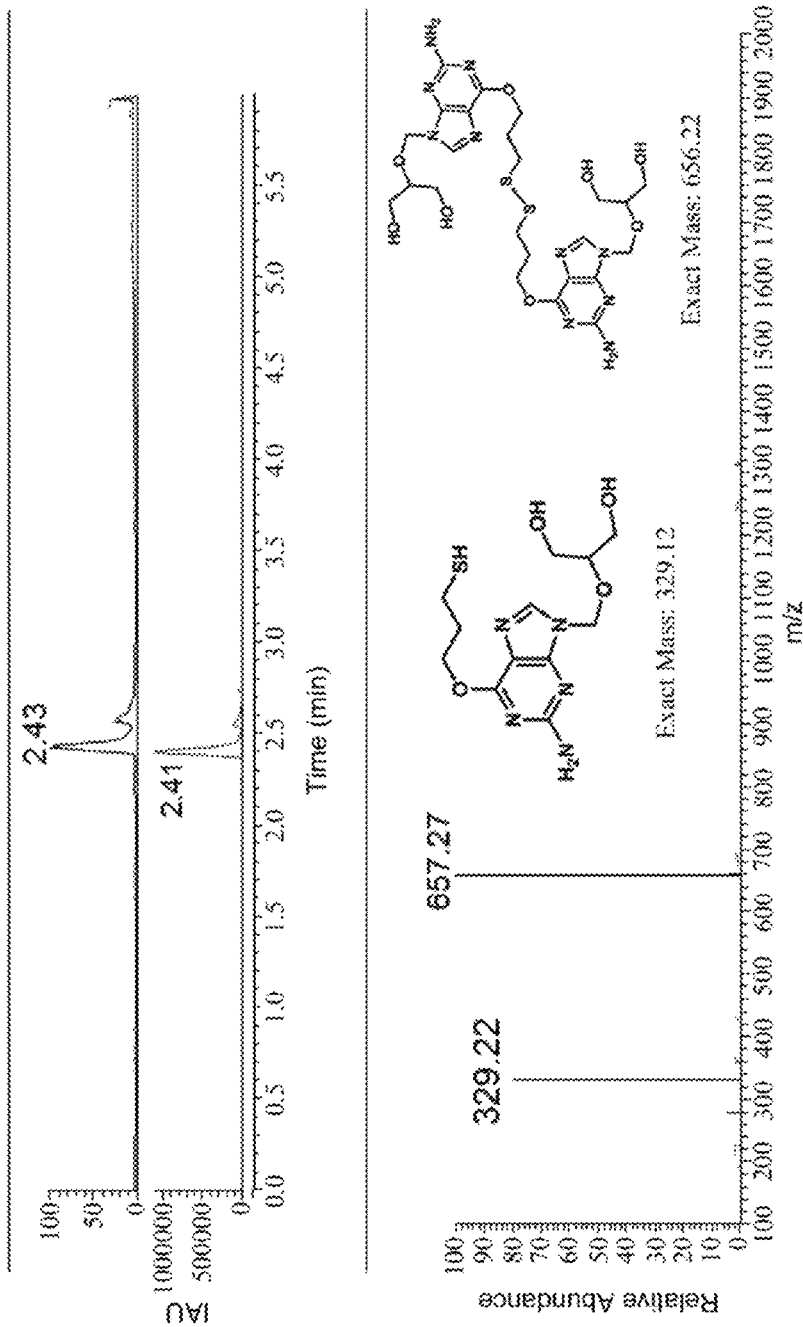

Thiol functionality was installed in the ganciclovir moiety by modifying the six membered aromatic ring of the drug without altering the important amine and two hydroxyl functional groups. The thiol group enabled attachment of biotin by reacting with biotin maleimide (FIG. 11A, Scheme 2). To synthesize the thiol analogue, acetyl protected ganciclovir was reacted with S-(3-hydroxypropyl) ethanethioate under Mitsunobu reaction conditions to provide the acetyl-protected ganciclovir thiol derivative. The acetyl groups were removed by treating RB III 105 with aqueous ammonia to provide the desired ganciclovir-thiol, RB III 108 in good yield (FIG. 11A, Scheme 1). The final product was characterized by $^1$H NMR (FIG. 11B), $^{13}$C NMR (FIG. 11C), and LCMS (FIG. 11D). In mass spectra, peak at 329.22 correspond to the desired mass along with the dimer peak at 657.27.

Figure 12:
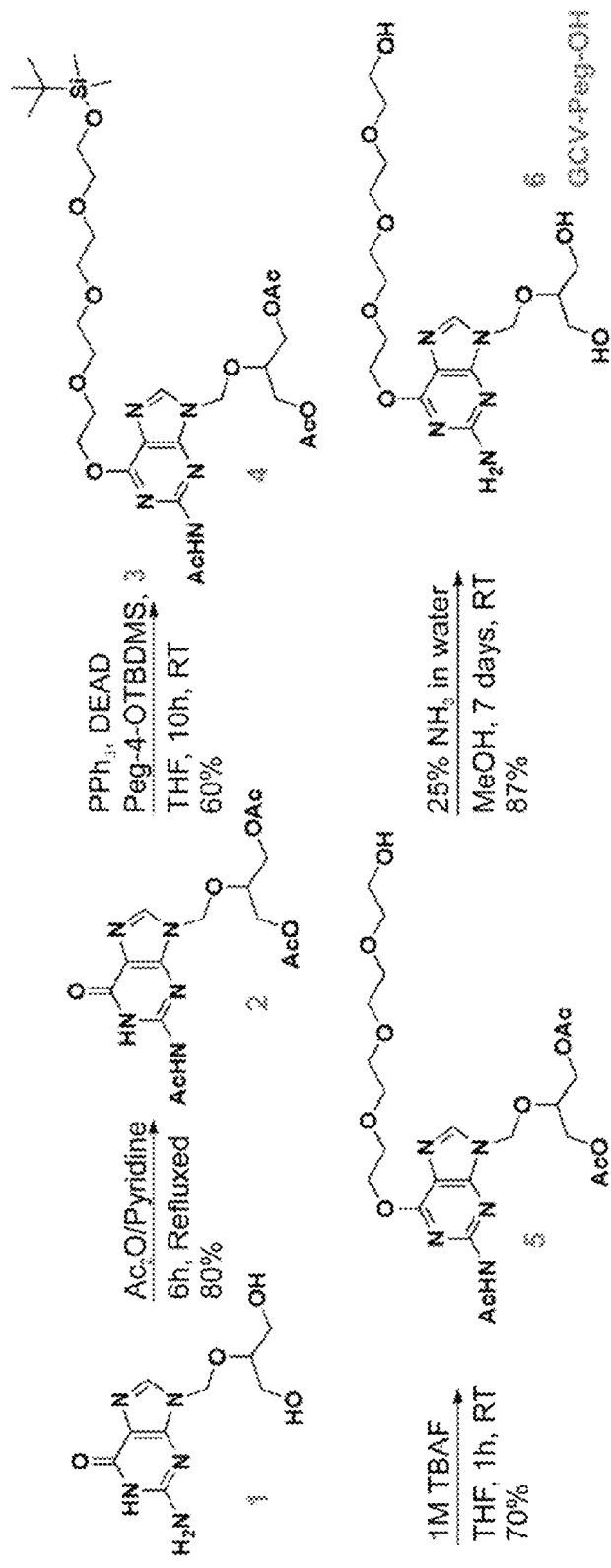
FIG. 12 shows the reaction scheme for the synthesis of the GCV-PEG monomer derivative.
Figure 13:
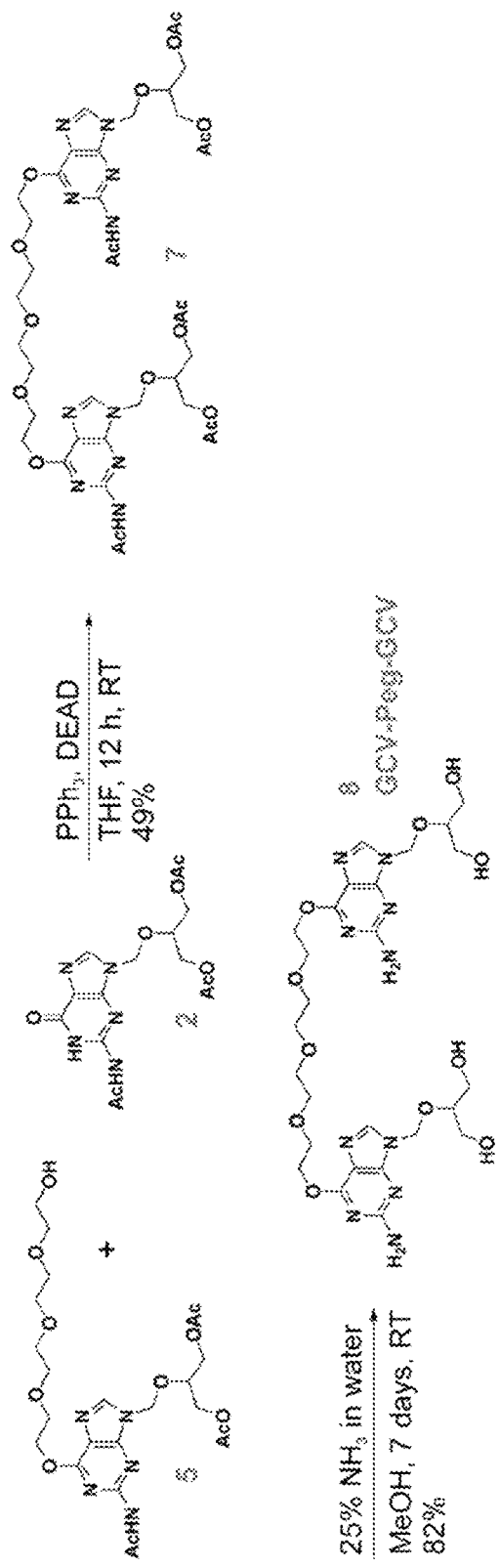
FIG. 13 shows the reaction scheme for the synthesis of the GCV-PEG dimer derivative.
Figure 14:
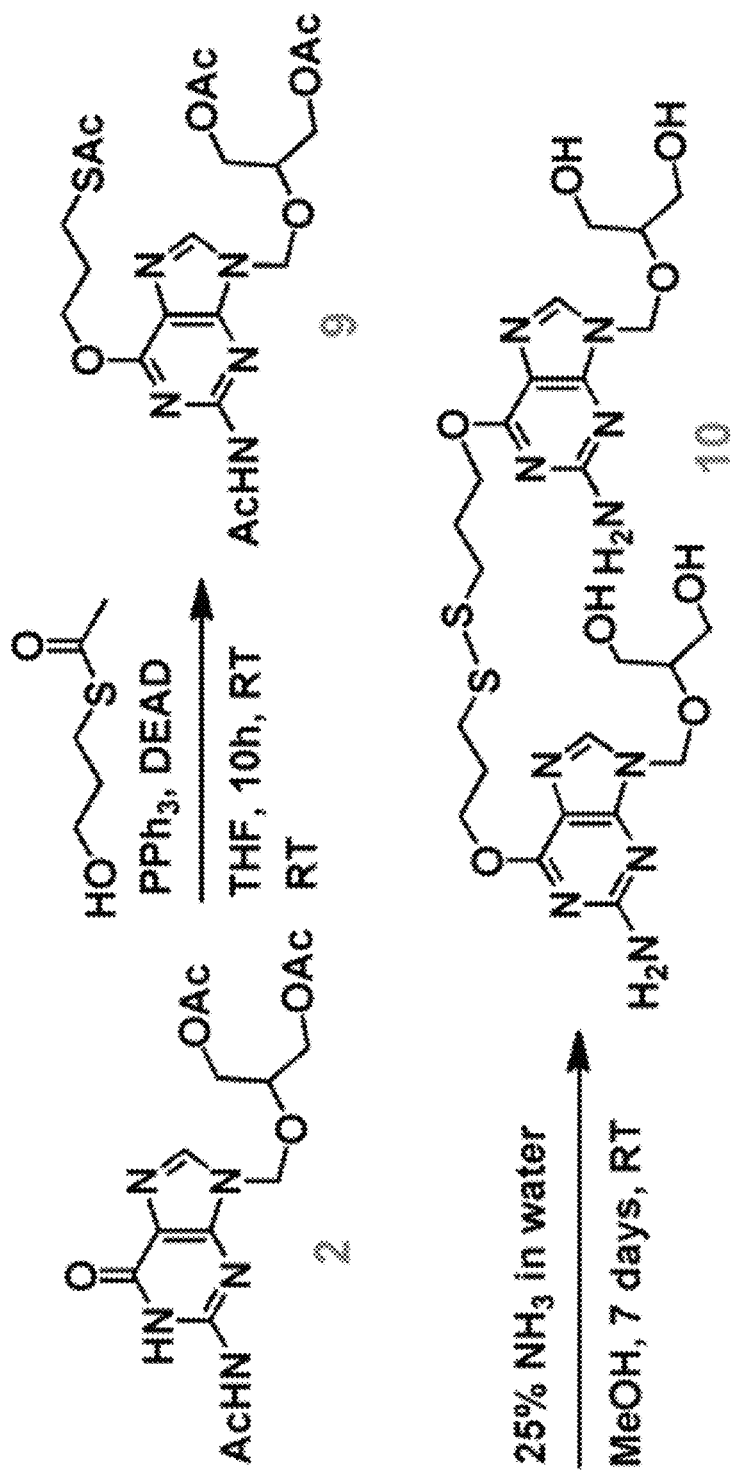
FIG. 14 shows the reaction scheme for the synthesis of the GCV-thiol dimer derivative.

Synthesis of Ganciclovir-PEG Monomer, Ganciclovir-PEG Dimer, and Thiol-Ganciclovir Dimer Derivatives The reaction schemes for synthesis of the GCV-PEG monomer, GCV-PEG dimer, and thiol-GCV dimer are shown in FIGS. 12-14.

Compound 3 was prepared as follows: NaH (60% oil dispersion, 10 mmol) was slowly added to solution of tetraethylene glycol (10 mmol) in dry THF (20 mL) at 25° C. and stirred the suspension for 45 minutes at same temperature. The reaction mixture was cooled to 0° C. with ice-bath and tert-Butyldimethylsilyl chloride (10 mmol) was added dropwise and ice-bath was removed and reaction was continued at 25° C. After 60 minutes, $H_2O$ (5 mL) was added to quenched the reaction and extracted with ethyl acetate (3×50 mL). The combined organic layer was washed with brine and dried over anhydrous sodium sulphate, filtered and evaporated to get oil. The crude oily product was purified by silica gel column chromatography using 2% Methanol/Dichloromethane to provide mono-TBDMS protected tetra-ethylene glycol, 3 (4.8 mmol, yield 48%) as a colorless oil. $^1$H NMR (CDCl$_3$, 400 MHz): δ 3.79 (t, J=4.0 Hz, 2 H), 3.75 (t, J=4.0 Hz, 2H), 3.71-3.67 (m, 8 H), 3.63 (t, J=4.0 Hz, 2 H), 3.57 (t, J=4.0 Hz, 2 H), 2.51 (s, 1 H), 0.91 (s, 9 H), 0.09 (s, 6 H), ESI-LC/MS: Expected [M+H]$^+$ for $C_{14}H_{32}O_5Si$ is 309.20, found m/z: 309.25 [M+H]$^+$.

Compound 2 was prepared as follows. Ganciclovir (1.0 g, 4.0 mmol), acetic anhydride (5.0 ml, 53 mmol), and pyridine (10.0 ml) were heated together, under reflux, for 6 hours. Initially, the reaction mixture was not homogeneous but once reaction completed, all were in the solution. The reaction was cooled, treated with methanol (5.0 ml), stirred for 30 minutes at 25° C., and then concentrated under reduced pressure. The crude gummy product was purified by silica gel column chromatography using 4-6% methanol/dichloromethane to provide tri-acetylated ganciclovir, 2 (1.2 g, 3.14 mmol, yield 80%) as a colorless powdered. $^1$H NMR (CDCl$_3$, 400 MHz): δ 12.02 (s, 1H), 9.49 (s, 1H), 7.84 (s, 1H), 5.55 (s, 2H), 4.19 (t, J=4.0 Hz, 4 H), 4.12 (m, 1H), 2.35 (s, 3H), 2.05 (s, 6H). ESI-LC/MS: Expected [M+H]$^+$ for $C_{15}H_{19}N_5O_7$ is 382.13, found m/z: 382.37 [M+H]$^+$.

Compound 4 was prepared as follows. To a suspension of acetylated ganciclovir, 2 (0.382 g, 1.0 mmol) in dry THF (5.0 mL) were subsequently added under stirring triphenylphosphine (0.393 g, 1.5 mmol) and alcohol, 3 (0.616 g, 2.0 mmol) under nitrogen atmosphere. Initially, reaction mixture was not clear but after 15 min when diethyl azodicarboxylate (DEAD) (0.261 g, 1.5 mmol) in dry THF (2.0 mL) was added drop wise, the reaction mixture turned yellow and started to become clear. The reaction was continued to stir at 25° C. for 10 hours. THF was evaporated under reduced pressure and the crude reaction mixture was extracted with DCM (3×30 mL) from water. The combined organic layer was washed with brine and dried over anhydrous sodium sulphate, filtered and evaporated to get yellowish oil. The crude product loaded on silica gel column and purified by 2-4% Methanol/Dichloromethane. Desired product, 4 was less polar than starting compound 2. The expected product was eluted in 3% MeOH/DCM solvent system as a colorless oil (0.403 g, 0.6 mmol, yield 60%). $^1$H NMR (400 MHz, CDCl$_3$): δ 8.13 (S, 1H), 7.96 (s, 1H), 5.66 (s, 2H), 4.68 (t, J=3.5 Hz, 2H), 4.21-4.14 (m, 2H), 4.11-4.02 (m, 2H), 3.93 (t, J=3.0 Hz, 2H), 3.79-3.72 (m, 5H), 3.69-3.67 (m, 6H), 3.54 (t, J=3.0 Hz, 2H), 2.56 (s, 3H), 1.97 (s, 6H), 0.88 (s, 9H), 0.06 (s, 6H). $^{13}$C NMR (CDCl$_3$, 100 MHz): δ 170.5, 161.0, 153.3, 152.5, 141.9, 117.4, 74.7, 72.6, 71.8, 70.8, 70.7, 70.66, 70.6, 68.9, 66.7, 62.9, 62.6, 25.9, 25.2, 20.6, −5.2. ESI-LC/MS: Expected [M+H]$^+$ for $C_{29}H_{49}N_5O_{11}Si$ is 672.32, found m/z: 672.51 [M+H]$^+$.

Compound 5 was prepared as follows. TBDMS protected ganciclovir, 4 (0.135 g, 0.2 mmol) was dissolved in THF (2 mL) and t added 1 M tetra-butyl ammonium fluoride (TBAF) in THF (5% water) (0.30 ml, 3.0 mmol) and stirred for 1 hour at 25° C. The progress of the reaction was monitored by the thin layer chromatography using 5% Methanol/Dichloromethane. The reaction was completed after 1 hour and quenched with water (100 μL) stirred for 10 minutes and concentrated under reduced pressure. The crude reaction mixture was purified by silica gel column eluting with 3-6% Methanol/Dichloromethane to provide pure colorless sticky liquid (0.078 g, yield 70%). $^1$H NMR (400 MHz, CDCl$_3$): δ 8.37 (s, 1H), 7.97 (s, 1H), 5.68 (s, 2H), 4.67 (t, J=4.0 Hz, 2H), 4.16-4.10 (m, 2H), 4.08-4.0 (m, 2H), 3.90 (t, J=4.0 Hz, 2H), 3.69 (m, 4H), 3.63 (m, 7H), 3.58 (m, 2H), 2.52 (s, 3H), 2.95 (s, 6H). $^{13}$C NMR (CD$_3$OD, 100 MHz): δ 170.5, 160.9, 153.3, 152.7, 141.5, 117.4, 74.8, 72.5, 71.9, 70.7, 70.6, 70.5, 70.3, 69.0, 66.6, 62.9, 61.6, 25.2, 20.6. ESI-LC/MS: Expected [M+H]$^+$ for $C_{23}H_{35}N_5O_{11}$ is 558.55, found m/z: 558.34 [M+H]$^+$.

Compound 6 was prepared as follows. Acetyl protected ganciclovir derivative, 5 (0.082 g, 0.148 mmol) was dissolved in methanol (2 mL) and 25% NH$_3$ in water (2 mL) was added and stirred for 25° C. After 2 and 4 days additional 2 ml of 25% NH$_3$ in water was added and continued stirring. The progress of the reaction was monitored by ESI-LCMS by aliquoting few microliters from the reaction mixture. After 7 days reaction was completed, no starting material was detected by LCMS. The reaction mixture was concentrated and dissolved in 5% methanol in water and purified by reverse-phase HPLC (Waters 2489 system) using a Bridge Prep C18 column (20 mm×250 mm, 5 μm particles, 300 Å pores) with a linear gradient of 5-35% B over 40 min (solvent A was water/0.1% TFA and solvent B was acetonitrile/0.1% TFA. Fractions containing desired product was lyophilized to provide pure compound 6 as a sticky oil (56.0 mg, yield 87%). $^1$H NMR (400 MHz, CD$_3$OD): δ 8.66 (s, 1H), 5.75 (s, 2H), 4.67 (s, 2H), 3.90 (m, 2H), 3.80 (m, 1H), 3.73-3.68 (m, 2H), 3.67-3.58 (m, 10H), 3.96-3.90 (m, 4H). $^{13}$C NMR (CD$_3$OD, 100 MHz):
δ 162.3, 160.9, 153.7, 140.9, 110.1, 82.9, 74.7, 73.9, 71.53, 71.50, 71.3, 70.0, 67.7, 62.6, 62.1. ESI-LC/MS: Expected [M+H]$^+$ for $C_{17}H_{29}N_5O_8$ is 432.44, found m/z: 432.40 [M+H]$^+$. Compound's purity was confirmed by reinjection on Water Acquity UPLC system using BEH C8 column (2.1 mm×100 mm, 1.7 μm) with a linear gradient of 10-90% B over 4 min produce a single peak with retention time 1.34 minutes (solvent A was water/0.1% TFA and solvent B was acetonitrile/0.1% TFA).

Compound 7 was prepared as follows. To a suspension of compound 5 (0.11 g, 0.2 mmol) and acetylated ganciclovir, 2 (0.152 g, 0.4 mmol) in dry THF (6.0 mL) were subsequently added under stirring triphenylphosphine (0.078 g, 0.03 mmol) under nitrogen atmosphere. The reaction mixture was cloudy initially but after 15 min when diethyl azodicarboxylate (DEAD) (0.069 g, 0.4 mmol) in dry THF (1.0 mL) was added drop wise, the reaction mixture turned yellow and became clear. The reaction was continued to stir at 25° C. for 12 hours. THF was evaporated under reduced pressure and the crude reaction mixture was evaporated under reduced pressure to get yellowish colored oil. The crude product loaded on silica gel column and purified by 10-20% Methanol/Ethyl Acetate solvent system to elute unreacted 2 then using 4-6% Methanol/Dichloromethane expected dimeric ganciclovir, 7 was eluted to provide colorless oil (0.09 g, yield 49%). $^1$H NMR (400 MHz, CD$_3$OD): δ 7.97 (s, 1H), 5.65 (s, 2H), 4.66 (t, J=4.0 Hz, 2H), 4.23-4.02 (m, 5H), 3.90 (t, J=4.0 Hz, 2H), 3.67 (m, 2H), 3.62 (m, 2H), 2.68 (bs, 2H), 2.49 (s, 3H), 1.95 (s, 6H). $^{13}$C NMR (CD$_3$OD, 100 MHz): δ 170.7, 160.8, 153.1, 152.5, 141.7, 117.3, 74.8, 71.9, 70.7, 70.5, 68.9, 66.6, 62.9, 29.6, 20.5. Expected [M+H]$^+$ for $C_{38}H_{52}N_{10}O_{17}$ is 921.35, found m/z: 921.44 [M+H]$^+$ Compound 8 was prepared as follows. Acetyl protected ganciclovir dimer, 7 (0.070 g, 0.076 mmol) was dissolved in methanol (2 mL) and 25% NH$_3$ in water (2 mL) was added and stirred for 25° C. After 2 and 4 days, additional 2 ml of 25% NH₃ in water was added and continued stirring. The progress of the reaction was monitored by ESI-LCMS by aliquoting few microliters from the reaction mixture. After 7 days reaction was completed, no starting material was detected by LCMS. The reaction mixture was concentrated and dissolved in 5% MeOH in water and purified by reverse-phase HPLC (Waters 2489 system) using a Bridge™ Prep C18 column (20 mm×250 mm, 5 µm particles, 300 Å pores) with a linear gradient of 5-35% B over 40 minutes (solvent A was water/0.1% TFA and solvent B was acetonitrile/0.1% TFA. Fractions containing desired product was lyophilized to provide pure compound 8 as sticky colorless oil (31.0 mg, yield 62%). $^1$H NMR (400 MHz, CD₃OD): δ 8.48 (s, 1H), 5.71 (s, 2H), 4.60 (s, 2H), 3.87 (m, 2H), 3.79 (m, 1H), 3.73-3.59 (m, 6H), 3.55-3.50 (m, 2H), $^{13}$C NMR (CD₃OD, 100 MHz): δ 162.2, 161.1, 153.9, 140.9, 110.9, 82.6, 74.5, 71.5, 70.1, 67.7, 62.6. Expected [M+H]⁺ for $C_{26}H_{40}N_{10}O_{11}$ is 669.29, found m/z: 669.56 [M+H]⁺. The compound's purity was confirmed by reinjection on Water Acquity UPLC system using BEH C8 column (2.1 mm×100 mm, 1.7 µm) with a linear gradient of 10-90% B over 4 min produce a single peak with retention time 1.59 min (solvent A was water/0.1% TFA and solvent B was acetonitrile/0.1% TFA).

Compound 9 was prepared as follows. To a suspension of acetylated ganciclovir, 2 (0.38 g, 1.0 mmol) in dry THF (10 mL) were subsequently added under stirring triphenylphosphane (0.314 g, 1.2 mmol) and acetyl protected thiopropanol (0.268 g, 2.0 mmol). Reaction was not clear. After 10 min DIAD (0.4 mL, 2 mmol) dissolved in THF (1 mL) was added dropwise and the mixture become clear and then stirred at 25° C. for 10 hours. THF was evaporated under reduced pressure and the crude reaction mixture was extracted with DCM (3×30 mL) from water. The combined organic layer was washed with brine and dried over anhydrous sodium sulphate, filtered and evaporated to get yellowish oil. The crude product was dissolved in a minimum volume of DCM and added dropwise to cold mixture of ether and hexane (20% hexane). The phosphine oxide stays in ether and product crushed out from ether, centrifuged and dissolved in DCM/MeOH, TLC showed little phosphine oxide and product and unreacted ganciclovir. The crude product loaded on silica gel column and purified by 1-2% Methanol/Dichloromethane (0.098 g, yield 20%). $^1$H NMR (CDCl₃, 400 MHz): δ 8.10 (s, 1 H), 7.97 (m, 1 H), 5.65 (s, 2 H), 4.59 (t, 2 H, J=6.2 Hz), 4.12 (m, 5 H), 3.07 (t, 2 H, J=7.1 Hz), 2.58 (s, 3 H), 2.34 (s, 3 H), 2.17 (m, 2 H), 1.98 (m, 6 H). $^{13}$C NMR (101 MHz, CDCl₃): δ 195.6, 170.5, 161.0, 153.3, 152.6, 141.5, 132.0, 128.6, 74.8, 71.9 66.1, 63.0, 28.9, 25.7, 25.7, 20.6. ESI-LC/MS: Expected [M+H]⁺ for $C_{20}H_{27}N_5O_8S$ is 498.16, found m/z: 498.08 [M+H]⁺.

Compound 10 was prepared as follows. Acetyl protected thiol ganciclovir, 9 (0.10 g, 0.2 mmol) was dissolved in methanol (5 mL) and 25% NH3 in water (5 mL) was added and stirred for 25° C. After 2 and 4 days, additional 2 ml of 25% NH₃ in water was added and continued stirring. The progress of the reaction was monitored by ESI-LCMS by aliquoting few microliters from the reaction mixture. After 7 days reaction was completed, no starting material was detected by LCMS. The reaction mixture was concentrated and dissolved in minimum volume of MeOH and dropwise added to the cold ether, centrifuged to provide pure product as a gummy liquid (0.025, 76%). 1H NMR (400 MHz, CD3OD): δ 7.98 (s, 1 H), 5.65 (s, 2 H), 4.56 (m, 2 H), 3.74 (m, 1 H), 3.62 (m, 2 H), 3.54 (m, 2 H), 2.92 (m, 2 H), 2.21 (m, 2 H). $^{13}$C NMR (CD3OD, 100 MHz): δ 160.9, 160.6, 153.8, 140.0, 113.6, 80.3, 72.1, 64.5, 61.3, 34.4, 28.2. Expected [M+H]+ for $C_{24}H_{36}N_{10}O_8S_2$ is 657.22, found m/z: 657.27 [M+H]+. The compound's purity was confirmed by reinjection on Water Acquity UPLC system using BEH C8 column (2.1 mm×100 mm, 1.7 µm) with a linear gradient of 10-90% B over 4 min produce a single peak with retention time 1.81 minutes (solvent A was water/0.1% TFA and solvent B was acetonitrile/0.1% TFA).

While the preferred embodiments of the invention have been illustrated and described, it will be appreciated that various changes can be made therein without departing from the spirit and scope of the invention.

TABLE 1

Secreted factors analyzed by Luminex array in BV-2 supernatants from cells treated with indicated concentrations of GCV for 24 hours. The detectable factors were not significantly changed with GCV treatment, n.d. = not detectable.

| Protein | Control | 100 µM GCV | 200 µM GCV |
|---|---|---|---|
| MCSF (pg/ml) | 16.79 ± 3.06 | 23.76 ± 3.77 | 25.48 ± 8.28 |
| TGFβ (pg/ml) | 3.76 ± 0.16 | 6.04 ± 0.58 | 5.36 ± 3.30 |
| MIP2 (pg/ml) | 11.75 ± 2.71 | 14.77 ± 1.50 | 13.02 ± 4.25 |
| VEGF (pg/ml) | 1.55 ± 0.38 | 1.65 ± 0.51 | 1.56 ± 0.27 |
| IL12p70 (pg/ml) | 0.29 ± 0.06 | 0.34 ± 0.05 | 0.16 ± 0.11 |
| MIP1β (ng/ml) | 266.62 ± 459.25 | 537.14 ± 449.94 | 4.13 ± 3.36 |
| IL17A (pg/ml) | 3.14 ± 0.33 | 3.5 ± 0.12 | 2.54 ± 1.28 |
| CCL2 (pg/ml) | 26.35 ± 0.82 | 28.8 ± 1.08 | 28.25 ± 2.19 |
| IL22 (pg/ml) | n.d. | n.d. | 3.09 ± 2.25 |
| CCL11 | n.d. | n.d. | n.d. |
| GCSF | n.d. | n.d. | n.d. |
| GM-CSF | n.d. | n.d. | n.d. |
| GROA | n.d. | n.d. | n.d. |
| IFNα | n.d. | n.d. | n.d. |
| IFNγ | n.d. | n.d. | n.d. |
| IL10 | n.d. | n.d. | n.d. |
| IL13 | n.d. | n.d. | n.d. |
| IL15 | n.d. | n.d. | n.d. |
| IL1α | n.d. | n.d. | n.d. |
| IL1β | n.d. | n.d. | n.d. |
| IL2 | n.d. | n.d. | n.d. |
| IL23 | n.d. | n.d. | n.d. |
| IL27 | n.d. | n.d. | n.d. |
| IL28 | n.d. | n.d. | n.d. |
| IL3 | n.d. | n.d. | n.d. |
| IL31 | n.d. | n.d. | n.d. |
| IL5 | n.d. | n.d. | n.d. |
| IL6 | n.d. | n.d. | n.d. |
| IL9 | n.d. | n.d. | n.d. |
| LIF | n.d. | n.d. | n.d. |
| LIX | n.d. | n.d. | n.d. |
| MCP3 | n.d. | n.d. | n.d. |
| MIP1α | n.d. | n.d. | n.d. |

What is claimed is:
1. A compound having the formula:

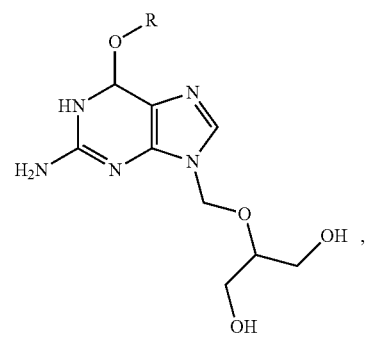

or a pharmaceutically acceptable salt thereof, wherein R is a propanethiol, 2-[(2-Amino-6-{2-[2-(2-ethoxyethoxy)ethoxy]ethoxy}-6,9-dihydro-1H-purin-9-yl)methoxy]-1,3-propanediol, or 2-({2-Amino-6[3-(propyldithio)propoxy]-6, 9-dihydro-1H-purin-9-yl}methoxy)-1,3-propanediol.

2. The compound of claim 1 having the formula:

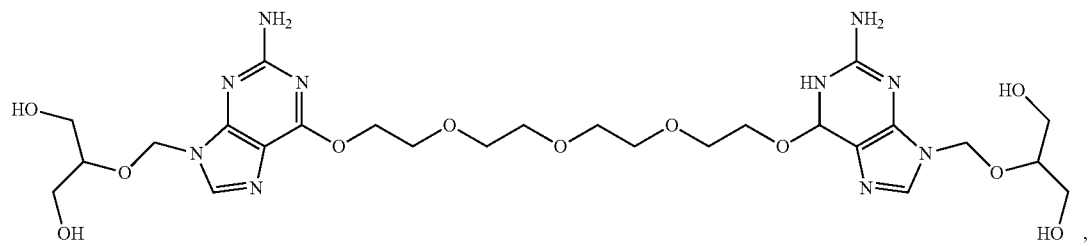 [SMILES: NC1=Nc2c(ncn2COC(CO)CO)C(OCCOCCOCCOCCOc2nc(N)nc3c2ncn3COC(CO)CO)N1]

or a pharmaceutically acceptable salt thereof.

3. The compound of claim 1 having the formula:

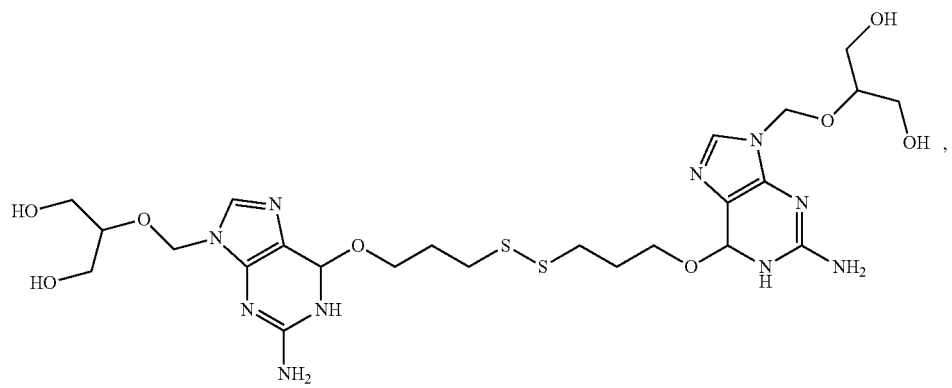 [SMILES: NC1=Nc2c(ncn2COC(CO)CO)C(OCCCSSCCCOC2NC(N)=Nc3c2ncn3COC(CO)CO)N1]

or a pharmaceutically acceptable salt thereof.

4. A pharmaceutical composition comprising the compound of claim 1 and a pharmaceutically acceptable excipient.

5. The pharmaceutical composition of claim 4, further comprising an anti-inflammatory agent, analgesic agent, or immunosuppressive agent.

6. A method for treating a subject for an inflammatory disorder, the method comprising administering to the subject a therapeutically effective amount of the compound of claim 1.

7. The method of claim 6, wherein treatment decreases neuroinflammation or systemic inflammation.

8. The method of claim 6, wherein treatment decreases the inflammatory response of microglia.

9. The method of claim 6, wherein treatment decreases microglial nitric oxide production.

10. The method of claim 6, wherein treatment induces a type I interferon response.

11. The method of claim 6, wherein multiple cycles of treatment are administered to the subject.

12. The method of claim 11, wherein the compound is administered intermittently.

13. The method of claim 11, wherein the compound is administered according to a daily dosing regimen.

14. The method of claim 6, wherein the compound is administered orally or intravenously.

15. The method of claim 6, wherein the compound is administered locally at the site of inflammation.

16. The method of claim 6, wherein the subject is human.

17. A method of decreasing neuroinflammation in a subject, the method comprising contacting microglia with the compound of claim 1.

18. A method of activating stimulator of interferon genes (STING) in a subject, the method comprising administering an effective amount of the compound of claim 1 to the subject.

19. A method of activating a type I interferon response in a subject, the method comprising administering an effective amount of the compound of claim 1 to the subject.

20. The method of claim 19, wherein IFN-β and CXCL10 are induced.

21. A kit comprising the composition of claim 4 and instructions for treating an inflammatory disorder.

22. The kit of claim 21, further comprising means for delivering said composition to a subject.

23. A kit comprising the compound of claim 1 and instructions for treating an inflammatory disorder.

24. A kit comprising the compound of claim 2 and instructions for treating an inflammatory disorder.

25. A kit comprising the compound of claim 3 and instructions for treating an inflammatory disorder.

* * * * *